(12) United States Patent
Heinrichs et al.

(10) Patent No.: US 8,729,013 B2
(45) Date of Patent: May 20, 2014

(54) METHODS OF INHIBITING STAPHYLOBACTIN-MEDIATED IRON UPTAKE IN S. AUREUS

(75) Inventors: David E. Heinrichs, London (CA); Suzanne Dale, Webster, NY (US)

(73) Assignee: The University of Western Ontario, London, Ontario (CA)

( * ) Notice: Subject to any disclaimer, the term of this patent is extended or adjusted under 35 U.S.C. 154(b) by 0 days.

(21) Appl. No.: 13/464,609

(22) Filed: May 4, 2012

(65) Prior Publication Data
US 2012/0322849 A1 Dec. 20, 2012

Related U.S. Application Data

(63) Continuation-in-part of application No. 12/588,067, filed on Oct. 2, 2009, now abandoned, which is a continuation-in-part of application No. 11/711,146, filed on Feb. 26, 2007, now abandoned, which is a continuation-in-part of application No. PCT/IB2005/003576, filed on Aug. 26, 2005.

(60) Provisional application No. 60/604,769, filed on Aug. 26, 2004.

(51) Int. Cl.
*A01N 37/00* (2006.01)
*C12N 15/11* (2006.01)

(52) U.S. Cl.
USPC .......................... 514/2.7; 514/44 A; 536/24.5

(58) Field of Classification Search
None
See application file for complete search history.

(56) References Cited

U.S. PATENT DOCUMENTS

| | | | |
|---|---|---|---|
| 5,554,507 A | 9/1996 | Grossman et al. | |
| 6,190,866 B1 * | 2/2001 | Nielsen et al. | 435/6.13 |
| 6,299,880 B1 | 10/2001 | Hodgson et al. | |
| 6,432,412 B1 | 8/2002 | Emery et al. | |
| 6,447,786 B1 | 9/2002 | Novick et al. | |
| 6,559,176 B1 | 5/2003 | Bassier et al. | |

FOREIGN PATENT DOCUMENTS

| | | |
|---|---|---|
| EP | 0694309 | 1/1996 |
| EP | 0749321 | 12/1996 |
| EP | 0917471 | 5/1999 |
| WO | 89/02077 | 3/1989 |
| WO | 90/11349 | 10/1990 |
| WO | 99/01473 | 1/1999 |
| WO | 99/26968 | 6/1999 |
| WO | 99/47662 | 9/1999 |
| WO | 00/71568 | 11/2000 |
| WO | 01/14421 | 3/2001 |
| WO | 01/60852 | 8/2001 |
| WO | 01/98499 | 12/2001 |
| WO | 02/34773 | 5/2002 |
| WO | 02/094868 | 11/2002 |
| WO | 2004/013166 | 2/2004 |

OTHER PUBLICATIONS

Cabrera et al (Appl. Environ. Microbiol. 2001, 67(2):1001).*
Nekhotiaeva et al (Molecular Therapy vol. 10, No. 4, Oct. 2004).*
Sebulsky et al (Journal of Bacteriology, Aug. 2000, p. 4394-4400 vol. 182, No. 16).*
Dale et al., Identification & Characterization of Genes Involved in Production of a Siderophore, Infection and Immunity, 72 (1):29-37 (2004).
Cabrera et al., (2001) Molecular Characterization of the Iron-Hydroxamate Uptake System, Appl. Environ. Microbiol. 67:1001-3.
Dale et al., (2004) Involvement of SirABC in Iron-Siderophore Import in *Staphylococcus aureus*, J. Bacteriol, 186:8356-62.
Sebulsky et al., Identification and Characterization of a Membrane Permease Involved n. IronHydroxamate Transport in *Staphylococcus aureus* (2000) J. Bacteriol. 182:4394-4400.
Heinrichs et al., Identification and Characterization of SirA, an Iron-Regulated Protein from *Staphylococcus aureus* (1999) J. Bacteriol. 181:1436-1443.
Speziali et al., Requirement of *Staphylococcus aureus* ATP-Binding Cassette-ATPase FhuC for Iron-Restricted Growth and Evidence that it functions with more than one iron transporter, J. of Bacteriology, 188(6):2048-2066 (2006).
Brown et al., Iron Acquisition by Gram-positive Bacterial Pathogens, Microbes and Infection, 4:1149-1156 (2002).
Brown et al., Immunization with Components of Two Iron Uptake ABC Transporters Protects Mice Against Systemic *Streptococcus pneumoniae* Infection, Infection and Immunity, 69(11):6702-6706 (2001).
Wizeman et al., Use of a Whole Genome Approach to Identify Vaccine Molecules Affording Protection against *Streptococcus pneumoniae* Infection, Infection and Immunity, 69(3):1593-1598 (2001).
Frank et al., Battling Bacterial Resistance—Shooting for the Genes, www.genomenewsnetwork.org/articles, (2000).
Morrissey et al., Molecular Cloning and Analysis of a putative Sireophore ABC Transporter from *Staphylococcus Aureus*, Infect. Immun. 68(11):6281-8 (2000).
Ji et al., Validation of Antibacterial Mechanism of Action using Regulated Antisense RNA Expression in *Staphylococcus aureus*, FEMS Microbiol Lett., 231(2):177-84 (2004).
Yin et al., Identification of Antimicrobial Targets Using a Comprehensive Genomic Approach, Pharmacogenomics, 5(1):101-13 (2004).
Sherman, Shutting Down Genes in Cancer, Bacteria and Viruses, S&TR p. 10-11 ((2004).
Dale et al., Identification of Stephylobactin Biosynthesis in *Ralstonia solanacearum*, America Society for Microbiology General Meeting, Apr. 2004.
Van Asbeck et al., European Journal of Clinical Microbiology, 2(5); (1983).
Rosen et al., Archives of Biochemistry and Biophysics, 208(2) (1981).
Diarra et al., Journal of Dairy Sciences (United States), 85(9) (2002).

* cited by examiner

*Primary Examiner* — Richard Schnizer
(74) *Attorney, Agent, or Firm* — Cesari and McKenna, LLP

(57) ABSTRACT

Methods of inhibiting *S. aureus* are provided. The methods include inhibition of polypeptides involved in the transport of the siderophore, staphylobactin.

9 Claims, 15 Drawing Sheets

Figure 6A

```
1    aaaaaattta attcatacta aatcgtgata atgattctca ttgtcataca tcacgaagga
61   ggctaattag tcaatgaata aagtaattaa aatgcttgtt gttacgcttg ctttcctact
121  tgttttagca ggatgtagtg ggaattcaaa taaacaatca tctgataaca aagataagga
181  aacaacttca attaaacatg caatgggtac aactgaaatt aaagggaaac caaagcgtgt
241  tgttacgcta tatcaaggtg ccactgacgt cgctgtatct ttaggtgtta aacctgtagg
301  tgctgtagaa tcatggacac aaaaaccgaa attcgaatac ataaaaaatg atttaaaaga
361  tactaagatt gtaggtcaag aacctgcacc taacttagag gaaatctcta aattaaaacc
421  ggacttaatt gtcgcgtcaa aagttagaaa tgaaaaagtt tacgatcaat tatctaaaat
481  cgcaccaaca gtttctactg atacagtttt caaattcaaa gatacaacta agttaatggg
541  gaaagcttta gggaaagaaa aagaagctga agatttactt aaaaagtacg atgataaagt
601  agctgcattc caaaaagatg caaaagcaaa gtataaagat gcatggccat tgaaagcttc
661  agttgttaac ttccgtgctg atcatacaag aatttatgct ggtggatatg ctggtgaaat
721  cttaaatgat ttaggattca aacgtaataa agacttacaa aaacaagttg ataatggtaa
781  agatattatc caacttacat ctaaagaaag cattccatta atgaacgctg atcatatttt
841  tgtagtaaaa tcagatccaa atgcgaaaga tgctgcatta gttaaaaaga ctgaaagcga
901  atggacttca agtaaagagt ggaaaaattt agacgcagtt aaaaacaacc aagtatctga
961  tgatttagat gaaatcactt ggaacttagc tggcggatat aaatcttcat taaaacttat
1021 tgacgattta tatgaaaagt taaatattga aaacaatca aaataattaa ggagttttac
1081 gatgctactt aaaccaaaat accaaatcgt tattgctggt ttatgtcttg caatagtagc
1141 tatcttaagt ttaatgattg gaaatacgct tgtgtcacca ggtacggtga tacaggcgtt
1201 attcaacttt gatagtgaaa acgattaca tgatgttgtc actggtgcac gggcgtcgag
1261 aacaatcatt gcgttattga ctggtgctgc ccttgctgtc tcaggtttgt tgatgcaagc
1321 acttacacga aacccaatag cctcaccagg gcttttcggt gtcaatgcag gcgcagtatt
1381 ttttgtcatt tttagtatta catttatcca aattcaatct tttaaaatga ttgtagttat
1441 tgcattttg ggggctattg ttgttactgt attagttgtt gcactaggta tgtttagaca
1501 aacactattc tcacctcacc gtgtcatttt ggcaggtgct gcgattgcga tgctatttac
1561 agccttact caaggcatac ttattatgaa cgaaacagac ttacaaggcc tattattttg
1621 gttaagtggc tccgtttcat tacgtaatat ttgggatatc ccatggatta ttccgcttgt
1681 attgatactt attttaattg catttagcat ggctgcacac atcaacatct tgatgacaag
1741 tgacgacatt gcaaccggcc tcggtcaaaa cataaaatta atcaaatgga tgattattat
1801 gctcatcagt atgttagccg gtatttcggt agccgtagct ggatcaatcg tctttgtggg
1861 tcttatcgta ccgaatatta gcaaacgatt attaccacca aactataagt atttaattcc
1921 ttttactgca ttagctggag caatcctaat gatcatttca gacattgttg ctcgtataat
1981 aattaagcca ctagagttgc ctatcggtgt cgttaccgct gtcattggcg ctattgtctt
2041 aatctatatt atgaagaaag gacgtcaacg cttatgaccg aaaagattaa taaaaaagac
2101 aattaccatc tcatcttcgc gttaatcttt ttagccatcg tttcagtggt aagtatgatg
2161 attggttcaa gctttatacc attacaacgc gtactgatgt acttataaa tccaaatgac
2221 agtatggatc aattcacttt agaagtatta cgcttacctc gcattacact tgcgatttta
2281 gcaggtgccg cactaggaat gagtggttta atgttgcaaa atgtattaaa aatccaatt
2341 gcctcacctg atattatcgg tatcacaggt ggtgctagct taagtgctgt tgtctttatt
2401 gcattttca gccatttaac aatacattta cttccactat ttgcagtatt aggtggcgca
2461 gttgcaatga tgatactatt agtgtttcaa acgaaaggac aaatacgccc gacaacactc
2521 ataatcatcg gtatttcgat gcaaacgttg tttattgcgc ttgtccaagg attactcatt
2581 acaacgaagc aattatctgc tgccaaagct tatacatggc tagtcggaag tctttacggt
2641 gctacgttta aagatacaat catttgggt atggttattt tagctgttgt gccgttgtta
2701 tttcttgtta taccaaaaat gaaaatatct atacttgatg accctgtagc gattggctta
2761 ggcttacatg tacaacgtat gaaactaatc caattaatca cttctactat actcgtatct
2821 atggcaatca gttagtagg taacattggg tttgtcggtt taatcgcacc acatatcgcg
2881 aaaacaatcg ttcgcggaag ttatgctaaa aagttactaa tgtcagcaat gattggtgcc
2941 atatcaattg ttattgcaga cttaattggg cgtaccttat tcttgcctaa agaagtgcca
3001 gcaggtgtat ttattgctgc ttttggtgcc ccattcttca tatacttatt attaaccgtg
3061 aaaaagttat aacgatatta ttaaaacaaa atgacctcac aacgaagtta gctaaatgat
3121 tcagttaact aaccgttgcg aggttttttt atacatatag ttgttgttat tgttaacaag
```
(SEQ ID NO: 1)

Figure 6B

```
cttgttaacaataacaacaactatatgtataaaaaacctcgcaacggttagttaactgaatcatttagct
aacttcgttgtgaggtcattttgttttaataatatcgttataacttttcacggttaataataagtatatg
aagaatggggcaccaaaagcagcaataaatacacctgctggcacttctttaggcaagaataaggtacgccc
aattaagtctgcaataacaattgatatggcaccaatcattgctgacattagtaacttttagcataacttc
cgcgaacgattgttttcgcgatatgtggtgcgattaaaccgacaaacccaatgttacctactaaactgatt
gccatagatacgagtatagtagaagtgattaattggattagtttcatacgttgtacatgtaagcctaagcc
aatcgctacagggtcatcaagtatagatattttcattttggtataacaagaaataacaacggcacaacag
ctaaaataaccatacccaaaatgattgtatctttaaacgtagcaccgtaaagacttccgactagccatgta
taagctttggcagcagataattgcttcgttgtaatgagtaatccttggacaagcgcaataaacaacgtttg
catcgaaataccgatgattatgagtgttgtcggcgtatttgtcctttcgtttgaaacactaatagtatca
tcattgcaactgcgccacctaatactgcaaatagtggaagtaaatgtattgttaaatggctgaaaaatgca
ataaagacaacagcacttaagctagcaccacctgtgataccgataatatcaggtgaggcaattggattttt
taatacattttgcaacattaaaccactcattcctagtgcggcacctgctaaaatcgcaagtgtaatgcgag
gtaagcgtaatacttctaaagtgaattgatccatactgtcatttggatttataaagtacatcagtacgcgt
tgtaatggtataaagcttgaaccaatcatcatacttaccactgaaacgatggctaaaaagattaacgcgaa
gatgagatggtaattgtcttttttattaatcttttcggtcataagcgttgacgtcctttcttcataatata
gattaagacaatagcgccaatgacagcggtaacgacaccgataggcaactctagtggcttaattattatac
gagcaacaatgtctgaaatgatcattaggattgctccagctaatgcagtaaaaggaattaaatacttatag
tttggtggtaataatcgtttgctaatattcggtacgataagacccacaaagacgattgatccagctacggc
taccgaaataccggctaacatactgatgagcataataatcatccatttgattaattttatgttttgaccga
ggccggttgcaatgtcgtcacttgtcatcaagatgttgatgtgtgcagccatgctaaatgcaattaaaata
agtatcaatacaagcggaataatccatgggatatcccaaatattacgtaatgaaacggagccacttaacca
aaataataggccttgtaagtctgtttcgttcataataagtatgccttgagtaaaggctgtaaatagcatcg
caatcgcagcacctgccaaaatgacacggtgaggtgagaatagtgtttgtctaaacatacctagtgcaaca
actaatacagtaacaacaatagcccccaaaaatgcaataactacaatcattttaaaagattgaatttggat
aaatgtaatactaaaaatgacaaaaaatactgcgcctgcattgacaccgaaaagccctggtgaggctattg
ggtttcgtgtaagtgcttgcatcaacaaacctgagacagcaagggcagcaccagtcaataacgcaatgatt
gttctcgacgcccgtgcaccagtgacaacatcatgtaaatcgttttcactatcaaagttgaataacgcctg
tatcaccgtacctggtgacacaagcgtatttccaatcattaaacttaagatagctactattgcaagacata
aaccagcaataacgatttggtattttggtttaagtagcatcgtaaaactccttaattattttgattgtttt
tcaatatttaacttttcatataaatcgtcaataagtttaatgaagatttatatccgccagctaagttcca
agtgatttcatctaaatcatcagatacttggttgttttaactgcgtctaaattttccactctttacttg
aagtccattcgctttcagtctttttaactaatgcagcatcttcgcatttggatctgattttactacaaaa
atatgatcagcgttcattaatggaatgctttctttagatgtaagttggataatatctttaccattatcaac
ttgttttttgtaagtctttattacgtttgaatcctaaatcatttaagatttccagcatatccaccagcat
aaattcttgtatgatcagcacggaagttaacaactgaagctttcaatggccatgcatctttatactttgct
tttgcatcttttggaatgcagctactttatcatcgtacttttaagtaaatcttcagcttctttttcttt
ccctaaagctttccccattaacttagttgtatctttgaatttgaaactgtatcagtagaaactgttggtg
cgattttagataattgatcgtaaacttttcatttctaacttttgacgcgacaattaagtccggttttaat
ttagagatttcctctaagttaggtgcaggttcttgacctacaatcttagtatcttttaaatcatttttat
gtattcgaatttcggttttgtgtccatgattctacagcacctacaggtttaacacctaaagatacagcga
cgtcagtggcaccttgatatagcgtaacaacacgctttggtttcctttaatttcagttgtacccattgca
tgtttaattgaagttgtttccttatctttgttatcagatgattgtttatttgaattcccactacatcctgc
taaaacaagtaggaaagcaagcgtaacaacaagcattttaattactttattcattgactaattagcctcct
tcgtgatgtatgacaatgagaatcattatcacgatttagtatgaattaaatttttt (SEQ ID NO: 2)
```

```
1   atgaataaag taattaaaat gcttgttgtt acgcttgctt cctacttgt tttagcagga
61  tgtagtggga attcaaataa acaatcatct gataacaaag ataaggaaac aacttcaatt
121 aaacatgcaa tgggtacaac tgaaattaaa gggaaaccaa agcgtgttgt tacgctatat
181 caaggtgcca ctgacgtcgc tgtatcttta ggtgttaaac ctgtaggtgc tgtagaatca
241 tggacacaaa aaccgaaatt cgaatacata aaaaatgatt taaaagatac taagattgta
301 ggtcaagaac ctgcacctaa cttagaggaa atctctaaat taaaaccgga cttaattgtc
361 gcgtcaaaag ttagaaatga aaaagtttac gatcaattat ctaaaatcgc accaacagtt
421 tctactgata cagttttcaa attcaaagat acaactaagt taatggggaa agctttaggg
481 aaagaaaaag aagctgaaga tttacttaaa aagtacgatg ataaagtagc tgcattccaa
541 aaagatgcaa aagcaaagta taaagatgca tggccattga agcttcagt tgttaacttc
601 cgtgctgatc atacaagaat ttatgctggt ggatatgctg gtgaaatctt aaatgattta
661 ggattcaaac gtaataaaga cttacaaaaa caagttgata atggtaaaga tattatccaa
721 cttacatcta aagaaagcat tccattaatg aacgctgatc atatttttgt agtaaaatca
781 gatccaaatg cgaaagatgc tgcattagtt aaaaagactg aaagcgaatg gacttcaagt
841 aaagagtgga aaaatttaga cgcagttaaa aacaaccaag tatctgatga tttagatgaa
901 atcacttgga acttagctgg cggatataaa tcttcattaa aacttattga cgatttatat
961 gaaaagttaa atattgaaaa acaatcaaaa taa (SEQ ID NO: 3)
```

B.

```
ttattttgattgttttcaatatttaacttttcatataaatcgtcaataagttttaatgaagatttatatc
cgccagctaagttccaagtgatttcatctaaatcatcagatacttggttgtttttaactgcgtctaaattt
ttccactcttttacttgaagtccattcgctttcagtctttttaactaatgcagcatctttcgcatttggatc
tgattttactacaaaaatatgatcagcgttcattaatggaatgctttctttagatgtaagttggataatat
ctttaccattatcaacttgttttgtaagtctttattacgtttgaatcctaaatcatttaagatttcacca
gcatatccaccagcataaattcttgtatgatcagcacggaagttaacaactgaagctttcaatggccatgc
atctttatactttgcttttgcatctttttggaatgcagctactttatcatcgtacttttaagtaaatctt
cagcttcttttttctttccctaaagctttccccattaacttagttgtatctttgaattttgaaaactgtatca
gtagaaactgttggtgcgattttagataattgatcgtaaacttttcatttctaacttttgacgcgacaat
taagtccggttttaatttagagatttcctctaagttaggtgcaggttcttgacctacaatcttagtatctt
ttaaatcatttttttatgtattcgaatttcggttttttgtgtccatgattctacagcacctacaggtttaaca
cctaaagatacagcgacgtcagtggcaccttgatatagcgtaacaacacgctttggtttccctttaatttc
agttgtacccattgcatgtttaattgaagttgtttccttatctttgttatcagatgattgtttatttgaat
tcccactacatcctgctaaaacaagtaggaaagcaagcgtaacaacaagcattttaattactttattcat
(SEQ ID NO: 4)
```

C.

```
MNKVIKMLVVTLAFLLVLAGCSGNSNKQSSDNKDKETTSIKHAMGTTEIKGKPKRVVTL
YQGATDVAVSLGVKPVGAVESWTQKPKFEYIKNDLKDTKIVGQEPAPNLEEISKLKPDL
IVASKVRNEKVYDQLSKIAPTVSTDTVFKFKDTTKLMGKALGKEKEAEDLLKKYDDKVA
AFQKDAKAKYKDAWPLKASVVNFRADHTRIYAGGYAGEILNDLGFKRNKDLQKQVDNGK
DIIQLTSKESIPLMNADHIFVVKSDPNAKDAALVKKTESEWTSSKEWKNLDAVKNNQVS
DDLDEITWNLAGGYKSSLKLIDDLYEKLNIEKQSK (SEQ ID NO: 5)
```

```
1   atgctactta aaccaaaata ccaaatcgtt attgctggtt tatgtcttgc aatagtagct
61  atcttaagtt taatgattgg aaatacgctt gtgtcaccag gtacggtgat acaggcgtta
121 ttcaactttg atagtgaaaa cgatttacat gatgttgtca ctggtgcacg ggcgtcgaga
181 acaatcattg cgttattgac tggtgctgcc cttgctgtct caggtttgtt gatgcaagca
241 cttacacgaa acccaatagc ctcaccaggg cttttcggtg tcaatgcagg cgcagtattt
301 tttgtcattt ttagtattac atttatccaa attcaatctt ttaaaatgat tgtagttatt
361 gcattttttgg gggctattgt tgttactgta ttagttgttg cactaggtat gtttagacaa
421 acactattct cacctcaccg tgtcattttg gcaggtctg cgattgcgat gctatttaca
481 gcctttactc aaggcatact tattatgaac gaaacagact acaaggcct attattttgg
541 ttaagtggct ccgtttcatt acgtaatatt tgggatatcc catggattat tccgcttgta
601 ttgatactta ttttaattgc atttagcatg gctgcacaca tcaacatctt gatgacaagt
661 gacgacattg caaccggcct cggtcaaaac ataaaattaa tcaaatggat gattattatg
721 ctcatcagta tgttagccgg tatttcggta gccgtagctg gatcaatcgt ctttgtgggt
781 cttatcgtac cgaatattag caaacgatta ttaccaccaa actataagta tttaattcct
841 tttactgcat tagctggagc aatcctaatg atcatttcag acattgttgc tcgtataata
901 attaagccac tagagttgcc tatcggtgtc gttaccgctg tcattggcgc tattgtctta
961 atctatatta tgaagaaagg acgtcaacgc ttatga (SEQ ID NO: 6)
```

B.

```
tcataagcgttgacgtcctttcttcataatatagattaagacaatagcgccaatgacagcggtaacgacac
cgataggcaactctagtggcttaattattatacgagcaacaatgtctgaaatgatcattaggattgctcca
gctaatgcagtaaaaggaattaaatacttatagtttggtggtaataatcgtttgctaatattcggtacgat
aagacccacaaagacgattgatccagctacggctaccgaaataccggctaacatactgatgagcataataa
tcatccatttgattaattttatgttttgaccgaggccggttgcaatgtcgtcacttgtcatcaagatgttg
atgtgtgcagccatgctaaatgcaattaaaataagtatcaatacaagcggaataatccatgggatatccca
aatattacgtaatgaaacggagccacttaaccaaaataataggccttgtaagtctgtttcgttcataataa
gtatgccttgagtaaaggctgtaaatagcatcgcaatcgcagcacctgccaaaatgacacggtgaggtgag
aatagtgtttgtctaaacatacctagtgcaacaactaatacagtaacaacaatagccccccaaaaatgcaat
aactacaatcattttaaaagattgaatttggataaatgtaatactaaaaatgacaaaaaatactgcgcctg
cattgacaccgaaaagccctggtgaggctattgggtttcgtgtaagtgcttgcatcaacaaacctgagaca
gcaagggcagcaccagtcaataacgcaatgattgttctcgacgcccgtgcaccagtgacaacatcatgtaa
atcgttttcactatcaaagttgaataacgcctgtatcaccgtacctggtgacacaagcgtatttccaatca
ttaaacttaagatagctactattgcaagacataaaccagcaataacgatttggtattttggtttaagtagc
at (SEQ ID NO: 7)
```

C.

```
MLLKPKYQIVIAGLCLAIVAILSLMIGNTLVSPGTVIQALFNFDSENDLHDVVTGARAS
RTIIALLTGAALAVSGLLMQALTRNPIASPGLFGVNAGAVFFVIFSITFIQIQSFKMIV
VIAFLGAIVVTVLVVALGMFRQTLFSPHRVILAGAAIAMLFTAFTQGILIMNETDLQGL
LFWLSGSVSLRNIWDIPWIIPLVLILILIAFSMAAHINILMTSDDIATGLGQNIKLIKW
MIIMLISMLAGISVAVAGSIVFVGLIVPNISKRLLPPNYKYLIPFTALAGAILMIISDI
VARIIKPLELPIGVVTAVIGAIVLIYIMKKGRQRL (SEQ ID NO: 8)
```

```
1   atgaccgaaa agattaataa aaaagacaat taccatctca tcttcgcgtt aatcttttta
61  gccatcgttt cagtggtaag tatgatgatt ggttcaagct ttataccatt acaacgcgta
121 ctgatgtact ttataaatcc aaatgacagt atggatcaat tcactttaga agtattacgc
181 ttacctcgca ttacacttgc gattttagca ggtgccgcac taggaatgag tggtttaatg
241 ttgcaaaatg tattaaaaaa tccaattgcc tcacctgata ttatcggtat cacaggtggt
301 gctagcttaa gtgctgttgt ctttattgca ttttcagcc atttaacaat acatttactt
361 ccactatttg cagtattagg tggcgcagtt gcaatgatga tactattagt gtttcaaacg
421 aaaggacaaa tacgcccgac aacactcata atcatcggta tttcgatgca aacgttgttt
481 attgcgcttg tccaaggatt actcattaca acgaagcaat tatctgctgc caaagcttat
541 acatggctag tcggaagtct ttacggtgct acgtttaaag atacaatcat tttgggtatg
601 gttattttag ctgttgtgcc gttgttattt cttgttatac aaaaatgaa aatatctata
661 cttgatgacc ctgtagcgat tggcttaggc ttacatgtac aacgtatgaa actaatccaa
721 ttaatcactt ctactatact cgtatctatg gcaatcagtt tagtaggtaa cattgggttt
781 gtcggtttaa tcgcaccaca tatcgcgaaa acaatcgttc gcggaagtta tgctaaaaag
841 ttactaatgt cagcaatgat tggtgccata tcaattgtta ttgcagactt aattgggcgt
901 accttattct tgcctaaaga agtgccagca ggtgtattta ttgctgcttt tggtgcccca
961 ttcttcatat acttattatt aaccgtgaaa aagttataa (SEQ ID NO: 9)
```

B.

```
ttataacttttttcacggttaataataagtatatgaagaatggggcaccaaaagcagcaataaatacacctg
ctggcacttctttaggcaagaataaggtacgcccaattaagtctgcaataacaattgatatggcaccaatc
attgctgacattagtaactttttagcataacttccgcgaacgattgttttcgcgatatgtggtgcgattaa
accgacaaacccaatgttacctactaaactgattgccatagatacgagtatagtagaagtgattaattgga
ttagtttcatacgttgtacatgtaagcctaagccaatcgctacagggtcatcaagtatagatattttcatt
tttggtataacaagaaataacaacggcacaacagctaaaataaccatacccaaaatgattgtatctttaaa
cgtagcaccgtaaagacttccgactagccatgtataagctttggcagcagataattgcttcgttgtaatga
gtaatccttggacaagcgcaataaacaacgtttgcatcgaaataccgatgattatgagtgttgtcgggcgt
atttgtcctttcgtttgaaacactaatagtatcatcattgcaactgcgccacctaatactgcaaatagtgg
aagtaaatgtattgttaaatggctgaaaaatgcaataaagacaacagcacttaagctagcaccacctgtga
taccgataatatcaggtgaggcaattggattttttaatacattttgcaacattaaaccactcattcctagt
gcggcacctgctaaaatcgcaagtgtaatgcgaggtaagcgtaatacttctaaagtgaattgatccatact
gtcatttggatttataaagtacatcagtacgcgttgtaatggtataaagcttgaaccaatcatcatactta
ccactgaaacgatggctaaaaagattaacgcgaagatgagatggtaattgtctttttattaatcttttcg
gtcat (SEQ ID NO: 10)
```

C.

```
MTEKINKKDNYHLIFALIFLAIVSVVSMMIGSSFIPLQRVLMYFINPNDSMDQFTLEVL
RLPRITLAILAGAALGMSGLMLQNVLKNPIASPDIIGITGGASLSAVVFIAFFSHLTIH
LLPLFAVLGGAVAMMILLVFQTKGQIRPTTLIIIGISMQTLFIALVQGLLITTKQLSAA
KAYTWLVGSLYGATFKDTIILGMVILAVVPLLFLVIPKMKISILDDPVAIGLGLHVQRM
KLIQLITSTILVSMAISLVGNIGFVGLIAPHIAKTIVRGSYAKKLLMSAMIGAISIVIA
DLIGRTLFLPKEVPAGVFIAAFGAPFFIYLLLTVKKL (SEQ ID NO: 11)
```

Figure 10
A.

```
   1 tttggatcca caagtttcaa aagcaaagcg attaattaaa caaatcgata aagatgcatt
  61 cctcgtaatt catgatgtaa gagatgtcta tggtaatggc tttcttgcag atgaataaat
 121 aaatggtatg agcacacata cttaaataga agtccacgga caagttttttg aactatgaag
 181 acttatctgt gggcgttttt tattttataa agtaatata caagacatga caaatcgagc
 241 tatccaattt aaaaagtaat gttagtcaat aagattgaaa aatgttataa tgatgttcat
 301 gataatcatt atcaattggg atgtctttga aaattgataa tttaaaaata gaattatttt
 361 tttataaaca gaaagaattt tattgaaagt agggaaatta tgaatcgttt gcatggacaa
 421 caagttaaaa ttggttacgg ggataacacg attataaata aattagatgt tgaaatacca
 481 gatggcaaag tgacgtcaat cattggtcct aacggctgcg ggaaatctac tttgctaaag
 541 gcattgtcac gtttattggc agttaaagaa ggcgaagtat ttttagatgg tgaaaatatt
 601 catacacaat ctacgaaaga gattgcaaaa aaaatagcca ttttacctca atcacctgaa
 661 gtagcagatg gcttaactgt tggggaatta gtttcatatg gtcgttttcc acatcaaaaa
 721 ggatttggta gattaactgc tgaggataag aaagaaattg attgggcaat ggaagttaca
 781 ggaactgata cattccgaca ccgttcaatc aatgatttaa gtggtggtca aagacaacgt
 841 gtttggattg caatggcatt agcacaaaga actgatatta tctttttaga cgaaccaaca
 901 acatatttag atatctgtca tcaattagaa atactagaat tagttcagaa gctaaatcag
 961 gaacaaggtt gtacaattgt catggttctt catgatatca accaagcgat tcgtttctca
1021 gatcatctta ttgcgatgaa agaaggggat atcatcgcta caggttcaac agaagacgta
1081 ttaacacagg aaatattaga aaagttttt aatattgatg ttgttttaag taaagatcct
1141 aaaactggaa aacctttact ggtaacttat gacttatgtc gcagagctta ttcttaatta
1201 agtaagttaa tatgataaaa aggacaatta acatgacaaa tagagagaac ccaacgccat
1261 tgaagttttt atcctatatt ataggtttaa gtatgatact actaatcaca ctatttattt
1321 ctacattaat aggtgacgcc aaaattcaag cctctacaat tatagaggct attttaatt
1381 ataatcctag caatcaacag caaaacatca tcaatgagat taggattccc agaaatatag
1441 cagcagtaat tgtaggtatg gcgcttgcag tttctggtgc gattatacaa ggtgttactc
1501 gtaatggtct tgctgatccg gcgctcatag gtttaaattc aggtgcttca tttgctttag
1561 cattaacata tgcagtttta ccaaacactt cattttttaat attgatgttt gctggatttt
1621 taggtgctat tctaggaggt gctattgtat taatgatagg ccgatctaga cgtgatggat
1681 ttaatccgat gcgtattatt ttagcgggtg cagcagtaag tgctatgtta acagcgctaa
1741 gtcaaggtat tgcattagct tttagactaa atcaaacagt aacattttgg actgctggag
1801 gcgtttcagg cacaacatgg tcacacctta gtgggcaat tccattaatt ggtattgcgt
1861 tattcattat attaacaatt agtaaacaac ttaccatttt aaatcttggt gaatcattag
1921 ctaaaggttt aggtcaaaat gtaacaatga tcagaggcat atgtttaatt attgctatga
1981 ttctagcagg tattgcagtt gctatcgctg acaagttgc atttgtaggt ttgatggtac
2041 ctcatatagc aagatttta attggaactg attatgctaa aattctacca ttaacagcct
2101 tgttaggtgg gatactcgtg cttgttgccg atgtgatagc acgatattta ggagaagcgc
2161 ctgttggtgc aatcatttca tttatcggtg ttccttactt tttatattta gttaaaaaag
2221 gaggacgctc aatatgatta gttcaaataa taacgcaga caattgatag cactggctgt
2281 ttttagcatt ctactatttc taggttgtac ttggagtatt acctcaggtg aatacaacat
2341 acctgttgaa agattttca aactttaat tggacaaggt gatgccattg atgagttaat
2401 cttattagat ttcaggttac ctcggatgat gattactatt ttggctggcg cagcgcttag
2461 tattagtggt gcaatagtgc aaagtgtcac aaaaaatcca atagctgaac caggtatatt
2521 aggtattaac gcaggtggcg gatttgcaat cgcattattt attgcaattg gtaaaattaa
2581 tgctgacaac tttgtttatg tactgccgtt aataagtata ctaggtggta tcaccactgc
2641 attgattatt tttattttca gttttaataa aaatgaaggt gttacacctg cgagtatggt
2701 attaataggt gtaggtttac aaacagcatt atatggtggc tcaattacaa ttatgtcaaa
2761 atttgatgat aagcaatctg atttcatcgc tgcttggttt gcaggtaata tttggggtga
2821 cgaatggcca tttgtcattg catttttacc gtgggtgttg attattattc cttacttact
2881 atttaaatcg aatacactaa atattattca tacgggtgat aatattgcac gaggtctagg
2941 tgtaaggtta agcagagaac gtttaatatt attctttatc gcagtgatgt tatcatctgc
```

Figure 10 A (cont'd)

```
3001 tgctgtagca gtagcaggtt caatttcgtt tatcggatta atgggtccgc atattgccaa
3061 acgtatcgtt ggaccacgtc accagttgtt tttaccaatt gccattttag taggggcatg
3121 tttacttgtt atagctgata caattggcaa aattgtatta caaccaggtg gggttccagc
3181 aggtattgtc gtagcaatta ttggtgcacc gtatttctta tatttaatgt acaaaacgaa
3241 aaatgtatag tgtcaatgga cacaacttat tgctatgaaa ggcactttat tataaggctt
3301 ttcatagcat tttttattta atgagccact caagactatt tattttttca ataatgaacc
3361 attaagttat caagaggatc ttatcaaaaa tatatttgat aacggtatca ggttaattct
3421 ttatgatagc gcattcattt attctgtttt atactatgac tgataatacc aaggaggtac
3481 aacatgatga aaaagttaat caataaaaaa gaaacatttt taactgatat gcttgaagga
3541 ttgttaattg cgcacccaga gttagatctg attgctaata cagttattgt aaaaaaagct
3601 aagaaagaac atggtgtagc aatagtctct ggaggtggaa gcggacatga acctgcgcat
3661 gccggttttg ttgcagaagg tatgctagat gcagcggttt gtggcgaagt atttacatcg
3721 gatccaaa (SEQ ID NO: 12)
```

B.
```
tttggatccgatgtaaatacttcgccacaaaccgctgcatctagcatacccttctgcaacaaaaccggcatgcgcagg
ttcatgtccgcttccacctccagagactattgctacaccatgttctttcttagcttttttttacaataactgtattag
caatcagatctaactctgggtgcgcaattaacaatccttcaagcatatcagttaaaaatgtttctttttttattgatt
aacttttttcatcatgttgtacctccttggtattatcagtcatagtataaaacagaataaatgaatgcgctatcataa
agaattaacctgataccgttatcaaatatattttttgataagatcctcttgataacttaatggttcattattgaaaaa
ataaatagtcttgagtggctcattaaataaaaaatgctatgaaaagccttataataaagtgccttcatagcaataa
gttgtgtccattgacactatacatttttcgttttgtacattaaatataagaaatacggtgcaccaataattgctacg
acaatacctgctggaaccccacctggttgtaatacaattttgccaattgtatcagctataacaagtaaacatgcccc
tactaaaatggcaattggtaaaaacaactggtgacgtggtccaacgatacgtttggcaatatgcggaccccattaatc
cgataaacgaaattgaacctgctactgctacagcagcagatgataacatcactgcgataaagaataatattaaacgt
tctctgcttaaccttacacctagacctcgtgcaatattatcacccgtatgaataatatttagtgtattcgatttaaa
tagtaagtaaggaataataatcaacacccacggtaaaaatgcaatgacaaatggccattcgtcaccccaaatattac
ctgcaaaccaagcagcgatgaaatcagattgcttatcatcaaattttgacataattgtaattgagccaccatataat
gctgtttgtaaacctacacctattaataccatactcgcaggtgtaacaccttcatttttattaaaactgaaaataaa
aataatcaatgcagtggtgataccacctagtatacttattaacggcagtacataaacaaagttgtcagcattaattt
taccaattgcaataaataatgcgattgcaaatccgccacctgcgttaatacctaatatacctggttcagctattgga
ttttttgtgacactttgcactattgcaccactaatactaagcgctgcgccagccaaaatagtaatcatcatccgagg
taacctgaaatctaataagattaactcatcaatggcatcaccttgtccaattaaagttttgaaaaatctttcaacag
gtatgttgtattcacctgaggtaatactccaagtacaacctagaaatagtagaatgctaaaaacagccagtgctatc
aattgtctgcgtttattatttgaactaatcatattgagcgtcctccttttttaactaaatataaaagtaaggaaca
ccgataaatgaaatgattgcaccaacaggcgcttctcctaaatatcgtgctatcacatcggcaacaagcacgagtat
cccacctaacaaggctgttaatggtagaattttagcataatcagttccaattaaaaatcttgctatatgaggtacca
tcaaacctacaaatgcaacttgtccagcgatagcaactgcaatacctgctagaatcatagcaataattaaacatatg
cctctgatcattgttacattttgacctaaaccttttagctaatgattcaccaagatttaaaatggtaagttgtttact
aattgttaatataatgaataacgcaataccaattaatggaattgcccacttaaggtgtgaccatgttgtgcctgaaa
cgcctccagcagtccaaaatgttactgtttgatttagtctaaaagctaatgcaataccttgacttagcgctgttaac
atagcacttactgctgcacccgctaaaataatacgcatcggattaaatccatcacgtctagatcggcctatcattaa
tacaatagcacctcctagaatagcacctaaaaatccagcaaacatcaatattaaaaatgaagtgtttggtaaaactg
catatgttaatgctaaagcaaatgaagcacctgaatttaaacctatgagcgccggatcagcaagaccattacgagta
acaccttgtataatcgcaccagaaactgcaagcgccataccacaattactgctgctatatttctgggaatcctaat
ctcattgatgatgttttgctgttcgtaggattataattaaaaatagcctctataattgtagaggcttgaattt
tggcgtcacctattaatgtagaaataaatagtgtgattagtagtatcatacttaaacctataatataggataaaaac
ttcaatggcgttgggttctctctatttgtcatgttaattgtccttttttatcatattaacttacttaattaagaataa
gctctgcgacataagtcataagttaccagtaaaggttttccagttttaggatctttacttaaaacaacatcaatatt
aaaaactttttctaatatttcctgtgttaatacgtcttctgttgaacctgtagcgatgatatccccttcttttcatcg
caataagatgatctgagaaacgaatcgcttggttgatatcatgaagaaccatgacaattgtacaaccttgttcctga
tttagcttctgaactaattctagtatttctaattgatgacagatatctaaatatgttgttggttcgtctaaaagat
aatatcagttctttgtgctaatgccattgcaatccaaacacgttgtctttgaccaccacttaaatcattgattgaac
```

Figure 10 B (cont'd)

```
ggtgtcggaatgtatcagttcctgtaacttccattgcccaatcaatttctttcttatcctcagcagttaatctacca
aatccttttgatgtggaaaacgaccatatgaaactaattccccaacagttaagccatctgctacttcaggtgattg
aggtaaaatggctatttttttgcaatctctttcgtagattgtgtatgaatattttcaccatctaaaaatacttcgc
cttctttaactgccaataaacgtgacaatgcctttagcaaagtagatttcccgcagccgttaggaccaatgattgac
gtcactttgccatctggtatttcaacatctaatttatttataatcgtgttatccccgtaaccaatttttaacttgttg
tccatgcaaacgattcataatttccctactttcaataaaattctttctgtttataaaaaataatttctattttaaa
ttatcaattttcaaagacatcccaattgataatgattatcatgaacatcattataacattttcaatcttattgact
aacattacttttaaattggatagctcgatttgtcatgtcttgtatattacttttataaaataaaaaacgcccacag
ataagtcttcatagttcaaaaacttgtccgtggacttctatttaagtatgtgtgctcataccatttatttattcatc
tgcaagaaagccattaccatagacatctcttacatcatgaattacgaggaatgcatctttatcgatttgtttaatta
atcgctttgcttttgaaacttgtggatccaaa (SEQ ID NO: 13)
```

Figure 11

A.
```
1   atgaatcgtt tgcatggaca acaagttaaa attggttacg gggataacac gattataaat
61  aaattagatg ttgaaatacc agatggcaaa gtgacgtcaa tcattggtcc taacggctgc
121 gggaaatcta ctttgctaaa ggcattgtca cgtttattgg cagttaaaga aggcgaagta
181 tttttagatg gtgaaaatat tcatacacaa tctacgaaag agattgcaaa aaaaatagcc
241 attttacctc aatcacctga agtagcagat ggcttaactg ttgggggaatt agtttcatat
301 ggtcgttttc cacatcaaaa aggatttggt agattaactg ctgaggataa gaaagaaatt
361 gattgggcaa tggaagttac aggaactgat acattccgac accgttcaat caatgattta
421 agtggtggtc aaagacaacg tgtttggatt gcaatggcat tagcacaaag aactgatatt
481 atctttttag acgaaccaac aacatattta gatatctgtc atcaattaga aatactagaa
541 ttagttcaga agctaaatca ggaacaaggt tgtacaattg tcatggttct tcatgatatc
601 aaccaagcga ttcgtttctc agatcatctt attgcgatga agaaggggga tatcatcgct
661 acaggttcaa cagaagacgt attaacacag gaatattag aaaaagtttt taatattgat
721 gttgttttaa gtaaagatcc taaaactgga aaacctttac tggtaactta tgacttatgt
781 cgcagagctt attcttaa (SEQ ID NO: 14)
```

B.
```
ttaagaataagctctgcgacataagtcataagttaccagtaaaggttttccagttttaggatctttactta
aaacaacatcaatattaaaaactttttctaatatttcctgtgttaatacgtcttctgttgaacctgtagcg
atgatatccccttctttcatcgcaataagatgatctgagaaacgaatcgcttggttgatatcatgaagaac
catgacaattgtacaaccttgttcctgatttagcttctgaactaattctagtatttctaattgatgacaga
tatctaaatatgttgttggttcgtctaaaaagataatatcagttctttgtgctaatgccattgcaatccaa
acacgttgtctttgaccaccacttaaatcattgattgaacggtgtcggaatgtatcagttcctgtaacttc
cattgcccaatcaatttctttcttatcctcagcagttaatctaccaaatcctttttgatgtggaaaacgac
catatgaaactaattccccaacagttaagccatctgctacttcaggtgattgaggtaaaatggctatttt
tttgcaatctctttcgtagattgtgtatgaatattttcaccatctaaaaatacttcgccttctttaactgc
caataaacgtgacaatgcctttagcaaagtagatttcccgcagccgttaggaccaatgattgacgtcactt
tgccatctggtatttcaacatctaatttatttataatcgtgttatccccgtaaccaatttttaacttgttgt
ccatgcaaacgattcat (SEQ ID NO: 15)
```

C.
```
MNRLHGQQVKIGYGDNTIINKLDVEIPDGKVTSIIGPNGCGKSTLLKALSRLLAVKEGE
VFLDGENIHTQSTKEIAKKIAILPQSPEVADGLTVGELVSYGRFPHQKGFGRLTAEDKK
EIDWAMEVTGTDTFRHRSINDLSGGQRQRVWIAMALAQRTDIIFLDEPTTYLDICHQLE
ILELVQKLNQEQGCTIVMVLHDINQAIRFSDHLIAMKEGDIIATGSTEDVLTQEILEKV
FNIDVVLSKDPKTGKPLLVTYDLCRRAYS (SEQ ID NO: 16)
```

Figure 12

A.
TAACCAATTTTAACTTGTTGTCCATGCAAACGATTCATAATTTCCCTACTTTCAATAAA
ATTCTTTCTGTTTATAAAAAATAATTTCTATTTTTAAATTATCAATTTTC
(length: 109 bp) [SEQ ID NO: 34]

B.
TTTCAACATCTAATTTATTTATAATCGTGTTATCCCCGTAACCAATTTTAACTTGTTGT
CCATGCAAACGATTCATAATTTCCCTACTTTCAATAAAATTCTTTCTGTTTATAAAAAA
TAATTTCTATTTTTAAATTATCAATTTTC (length: 147 bp) [SEQ ID NO: 35]

C.
AAAGTAGATTTCCCGCAGCCGTTAGGACCAATGATTGACGTCACTTTGCCATCTGGTAT
TTCAACATCTAATTTATTTATAATCGTGTTATCCCCGTAACCAATTTTAACTTGTTGTC
CATGCAAACGATTCATAATTTCCCTACTTTCAATAAAATTCTTTCTGTTTATAAAAAAT
AATTTCTATTTTTAAATTATCAATTTTC (length: 205 bp) [SEQ ID NO: 36]

D.
TACTTCGCCTTCTTTAACTGCCAATAAACGTGACAATGCCTTTAGCAAAGTAGATTTCC
CGCAGCCGTTAGGACCAATGATTGACGTCACTTTGCCATCTGGTATTTCAACATCTAAT
TTATTTATAATCGTGTTATCCCCGTAACCAATTTTAACTTGTTGTCCATGCAAACGATT
CATAATTTCCCTACTTTCAATAAAATTCTTTCTGTTTATAAAAAATAATTTCTATTTTT
AAATTATCAATTTTC (length: 251 bp) [SEQ ID NO: 37]

METHODS OF INHIBITING STAPHYLOBACTIN-MEDIATED IRON UPTAKE IN S. AUREUS

CROSS-REFERENCE TO RELATED APPLICATIONS

This application is a continuation-in-part to U.S. application Ser. No. 12/588,067 filed on Oct. 2, 2009, which is a continuation-in-part to U.S. application Ser. No. 11/711,146 filed on Feb. 26, 2007, which claims priority to PCT/IB2005/003576 filed on Aug. 26, 2005, which claims priority to U.S. Provisional Application No. 60/604,769 filed on Aug. 26, 2004, the contents of each of which are hereby incorporated by reference in their entirety.

BACKGROUND

*Staphylococcus aureus* (*S. aureus*) is a prevalent human pathogen that causes a wide range of infections ranging from minor skin lesions, impetigo and food poisoning to more serious diseases such as sepsis, endocarditis, osteomyelitis, pneumonia, bacteremia, and toxic shock syndrome (Archer (1998) *Clin. Infect. Dis.* 26:1179-1181). Initially, penicillin could be used to treat even the worst *S. aureus* infections. However, the emergence of penicillin-resistant strains of *S. aureus* has reduced the effectiveness of penicillin in treating *S. aureus* infections and most strains of *S. aureus* encountered in hospital infections today do not respond to penicillin. Penicillin-resistant strains of *S. aureus* produce a lactamase, which converts penicillin to pencillinoic acid, and thereby destroys antibiotic activity. Furthermore, the lactamase gene often is propagated episomally, typically on a plasmid, and often is only one of several genes on an episomal element that, together, confer multidrug resistance.

Methicillins, introduced in the 1960s, largely overcame the problem of penicillin resistance in *S. aureus*. These compounds conserve the portions of penicillin responsible for antibiotic activity and modify or alter other portions that make penicillin a good substrate for inactivating lactamases. However, methicillin resistance has emerged in *S. aureus*, along with resistance to many other antibiotics effective against this organism, including vancomycin, aminoglycosides, tetracycline, chloramphenicol, macrolides and lincosamides. In fact, methicillin-resistant strains of *S. aureus* generally are multiply drug resistant. Methicillian-resistant *S. aureus* (MRSA) has become one of the most important nosocomial pathogens worldwide and poses serious infection control problems. Drug resistance of *S. aureus* infections poses significant treatment difficulties, which are likely to get much worse unless new therapeutic agents are developed. There is thus an urgent unmet medical need for new and effective therapeutic agents to treat *S. aureus* infections.

SUMMARY

Methods of inhibiting *Staphylococcus aureus* (*S. aureus*) are provided herein. In particular, it has been found that inhibition of one or more staphylobactin transport polypeptides, referred to herein as Sir polypeptides and a FhuC ATPase, inhibits *S. aureus*.

In another aspect, the present invention features novel antibiotics, including antibodies, antisense RNAs, and siRNAs that inhibit iron uptake in *S. aureus*.

A further aspect of the invention features screening assays for identifying agents that inhibit iron uptake in *S. aureus*. In one embodiment, the assay can identify agents that inhibit the interaction between SirA, SirB, SirC, staphylobactin, and/or FhuC.

In another embodiment, the assay identifies agents that inhibit the expression of Sir polypeptides and/or nucleic acids in *S. aureus*. In yet another embodiment, the assay is a phenotypic assay that scores the growth of *S. aureus* in iron-limited or -depleted media in the presence of a test compound to the absence of the test compound.

Further features and advantages of the instant disclosed inventions will now be discussed in conjunction with the following Detailed Description and Claims.

BRIEF DESCRIPTION OF THE DRAWINGS

FIG. 6 shows (A) the nucleic acid sequence of the SirABC operon corresponding to GenBank accession number AF079518 (SEQ ID NO: 1), and (B) the reverse complement thereof (SEQ ID NO: 2).

FIG. 7 shows (A) the nucleic acid (SEQ ID NO: 3), (B) the reverse complement of SEQ ID NO: 3 (SEQ ID NO: 4), and (C) the amino acid sequence of SirA (SEQ ID NO: 5).

FIG. 8 shows (A) the nucleic acid (SEQ ID NO: 6), (B) the reverse complement of SEQ ID NO: 6 (SEQ ID NO: 7), and (C) the amino acid sequence of SirB (SEQ ID NO: 8).

FIG. 9 shows (A) the nucleic acid (SEQ ID NO: 9), (B) the reverse complement of SEQ ID NO: 9 (SEQ ID NO: 10), and (C) the amino acid sequence of SirC (SEQ ID NO: 11).

FIG. 10 shows (A) nucleic acid of the FhuCBG operon corresponding to GenBank accession number AF251216 (SEQ ID NO: 12) and (B) the reverse complement thereof (SEQ ID NO: 13).

FIG. 11 shows (A) the nucleic acid (SEQ ID NO: 14), (B) the reverse complement of SEQ ID NO: 14 (SEQ ID NO: 15), and (C) the amino acid sequence of FhuC (SEQ ID NO: 16).

FIG. 12 illustrates nucleic acid sequences of inhibitory FhuC siRNAs (A-D).

DETAILED DESCRIPTION

1. General

Figure 1:
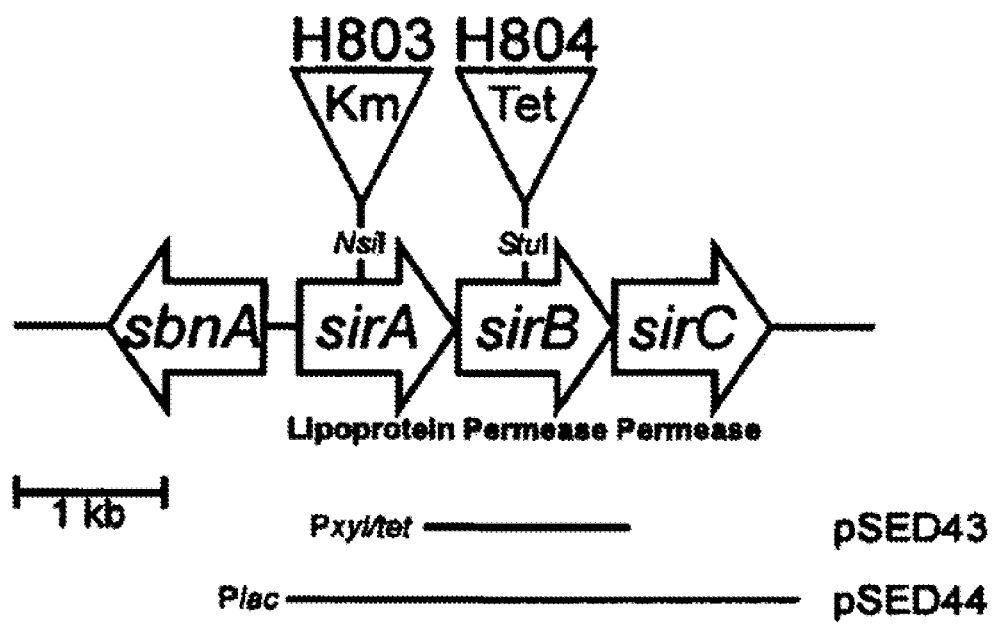
FIG. 1 shows the genetic organization of the sbn-sirABC locus. The three open reading frames of the sir operon as well as the first gene of the sbn operon (sbnA) are indicated. The positions of the insertion sites used to disrupt the sirA and sirB coding regions, generating strains H803 and H804, respectively, in the *S. aureus* Newman background are shown. Plasmids pSED43 and pSED44, used for complementation of sirB::tet and sirA::Km mutations, respectively, are shown.

The present invention is based at least in part on the discovery of the role of the *Staphylococcus aureus* (*S. aureus*) sirABC complex in the transport of the iron-siderophore, staphylobactin, as well as the identification of fhuC, as encoding an ATPase required for staphylobactin uptake via the SirABC transporter. Described herein are novel methods and antibiotics that inhibit *S. aureus*, including inhibition of iron uptake in *S. aureus*, and methods for screening compounds to identify additional inhibitors of the SirABC iron-siderophore transport system.

2. Definitions

For convenience, the meaning of certain terms and phrases employed in the specification, examples, and appended claims are provided below. Unless defined otherwise, all technical and scientific terms used herein have the same meaning as commonly understood by one of ordinary skill in the art to which this invention belongs.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. Agents may be identified by screening assays described herein below. Such agents may be inhibitors or antagonists of SirABC mediated iron transport in *Staphylococcus aureus*. The activity of such agents may render it suitable as a "therapeutic agent" which is a biologically, physiologically, or pharmacologically active substance (or substances) that acts locally or systemically in a subject.

The terms "antagonist" or "inhibitor" refer to an agent that reduces or inhibits at least one bioactivity of a protein. An antagonist may be a compound which reduces or inhibits the interaction between a protein and another molecule, e.g., a target peptide or enzyme substrate. An antagonist may also be a compound that reduces or inhibits expression of a gene or which reduces or inhibits the amount of expressed protein present.

As used herein the term "antibody" refers to an immunoglobulin and any antigen-binding portion of an immunoglobulin (e.g, IgG, IgD, IgA, IgM and IgE) i.e., a polypeptide that contains an antigen binding site, which specifically binds ("immunoreacts with") an antigen. Antibodies can comprise at least one heavy (H) chain and at least one light (L) chain inter-connected by at least one disulfide bond. The term "$V_H$" refers to a heavy chain variable region of an antibody. The term "$V_L$" refers to a light chain variable region of an antibody. In exemplary embodiments, the term "antibody" specifically covers monoclonal and polyclonal antibodies. A "polyclonal antibody" refers to an antibody which has been derived from the sera of animals immunized with an antigen or antigens. A "monoclonal antibody" refers to an antibody produced by a single clone of hybridoma cells. Techniques for generating monoclonal antibodies include, but are not limited to, the hybridoma technique (see Kohler & Milstein (1975) *Nature* 256:495-497); the trioma technique; the human B-cell hybridoma technique (see Kozbor et al. (1983) *Immunol. Today* 4:72), the EBV hybridoma technique (see Cole et al., 1985 In: *Monoclonal Antibodies and Cancer Therapy*, Alan R. Liss, Inc., pp. 77-96) and phage display.

Polyclonal or monoclonal antibodies can be further manipulated or modified to generate chimeric or humanized antibodies. "Chimeric antibodies" are encoded by immunoglobulin genes that have been genetically engineered so that the light and heavy chain genes are composed of immunoglobulin gene segments belonging to different species. For example, substantial portions of the variable (V) segments of the genes from a mouse monoclonal antibody, e.g., obtained as described herein, may be joined to substantial portions of human constant (C) segments. Such a chimeric antibody is likely to be less antigenic to a human than a mouse monoclonal antibody.

As used herein, the term "humanized antibody" (HuAb) refers to a chimeric antibody with a framework region substantially identical (i.e., at least 85%) to a human framework, having CDRs from a non-human antibody, and in which any constant region has at least about 85-90%, and preferably about 95% polypeptide sequence identity to a human immunoglobulin constant region. See, for example, PCT Publication WO 90/07861 and European Patent No. 0451216. All parts of such a HuAb, except possibly the CDRs, are substantially identical to corresponding parts of one or more native human immunoglobulin sequences. The term "framework region" as used herein, refers to those portions of immunoglobulin light and heavy chain variable regions that are relatively conserved (i.e., other than the CDRs) among different immunoglobulins in a single species, as defined by Kabat et al. (1987) *Sequences of Proteins of Immunologic Interest*, 4$^{th}$ Ed., US Dept. Health and Human Services. Human constant region DNA sequences can be isolated in accordance with well known procedures from a variety of human cells, but preferably from immortalized B cells. The variable regions or CDRs for producing humanized antibodies may be derived from monoclonal antibodies capable of binding to the antigen, and will be produced in any convenient mammalian source, including mice, rats, rabbits, or other vertebrates.

The term "antibody" also encompasses antibody fragments. Examples of antibody fragments include Fab, Fab', Fab'-SH, F(ab')$_2$, and Fv fragments; diabodies and any antibody fragment that has a primary structure consisting of one uninterrupted sequence of contiguous amino acid residues, including without limitation: single-chain Fv (scFv) molecules, single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g, CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s). Suitable leucine zipper sequences include the jun and fos leucine zippers taught by Kostelney et al., (1992) *J. Immunol.*, 148: 1547-1553 and the GCN4 leucine zipper described in U.S. Pat. No. 6,468,532. Fab and F(ab')$_2$ fragments lack the Fc fragment of intact antibody and are typically produced by proteolytic cleavage, using enzymes such as papain (to produce Fab fragments) or pepsin (to produce F(ab')$_2$ fragments).

An antibody "specifically binds" to an antigen or an epitope of an antigen if the antibody binds preferably to the antigen over most other antigens. For example, the antibody may have less than about 50%, 20%, 10%, 5%, 1% or 0.1% cross-reactivity toward one or more other epitopes.

An "effective amount" is an amount sufficient to produce a beneficial or desired clinical result upon treatment. An effective amount can be administered to a patient in one or more doses. In terms of treatment, an effective amount is an amount that is sufficient to decrease an infection in a patient. Several factors are typically taken into account when determining an appropriate dosage to achieve an effective amount. These factors include age, sex and weight of the patient, the condition being treated, the severity of the condition and the form and effective concentration of the agent administered.

"Equivalent" when used to describe nucleic acids or nucleotide sequences refers to nucleotide sequences encoding functionally equivalent polypeptides. Equivalent nucleotide sequences will include sequences that differ by one or more nucleotide substitution, addition or deletion, such as an allelic variant; and will, therefore, include sequences that differ due to the degeneracy of the genetic code. For example, nucleic acid variants may include those produced by nucleotide substitutions, deletions, or additions. The substitutions, deletions, or additions may involve one or more nucleotides. The variants may be altered in coding regions, non-coding regions, or both. Alterations in the coding regions may produce conservative or non-conservative amino acid substitutions, deletions or additions.

As used herein, the term "ferric hydroxamate uptake system" or "fhu system" refers to a group of genes that encode an ABC transporter. The fhu system is encoded by five genes. FhuC, fhuB, and fhu G are present in an operon (fhuCBG operon) and encode components of an ATP-binding cassette (ABC) transporter. FhuD1 and fhuD2 are separately encoded and encode lipoproteins that bind ferric hydroxamate complexes with high affinity. Exemplary nucleotide and amino acid sequences for the fhuCBG operon may be found in GenBank, Accession Nos. AF251216, AAF98153, AAF98154, and AAF98155; for fhuD1, Accession No. AF325854 and AAK92085; and for fhuD2 AF325855 and AAK92086. The terms "FhuC", "FhuB", "FhuG", "FhuD1", and "FhuD2" encompass fragments or portions thereof and biologically active fragments or portions thereof.

"Homology" or alternatively "identity" refers to sequence similarity between two peptides or between two nucleic acid molecules. Homology may be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. The term "percent identical" refers to sequence identity between two amino acid sequences or between two nucleotide sequences. Identity may be determined by comparing a position in each sequence which may be aligned for purposes of comparison. When an equivalent position in the compared sequences is occupied by the same base or amino acid, then the molecules are identical at that position; when the equivalent site is occupied by the same or a similar amino acid residue (e.g., similar in steric and/or electronic nature), then the molecules may be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and may be used with, e.g., default settings. ENTREZ is available through the National Center for Biotechnology Information, National Library of Medicine, National Institutes of Health, Bethesda, Md. In one embodiment, the percent identity of two sequences may be determined by the GCG program with a gap weight of 1, e.g., each amino acid gap is weighted as if it were a single amino acid or nucleotide mismatch between the two sequences. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See *Meth. Mol. Biol.* 70: 173-187 (1997). Also, the GAP program using the Needleman and Wunsch alignment method may be utilized to align sequences. An alternative search strategy uses MPSRCH software, which runs on a MASPAR computer. MPSRCH uses a Smith-Waterman algorithm to score sequences on a massively parallel computer. This approach improves the ability to pick up distantly related matches, and is especially tolerant of small gaps and nucleotide sequence errors. Nucleic acid-encoded amino acid sequences may be used to search both protein and DNA databases. Databases with individual sequences are described in *Methods in Enzymology*, ed. Doolittle, supra. Databases include Genbank, EMBL, and DNA Database of Japan (DDBJ).

As used herein, the term "infection" refers to an invasion and the multiplication of microorganisms such as *S. aureus* in body tissues, which may be clinically unapparent or result in local cellular injury due to competitive metabolism, toxins, intracellular replication or antigen antibody response. The infection may remain localized, subclinical and temporary if the body's defensive mechanisms are effective. A local infection may persist and spread by extension to become an acute, subacute or chronic clinical infection or disease state. A local infection may also become systemic when the microorganisms gain access to the lymphatic or vascular system. An infection of *S. aureus* may result in a disease or condition, including but not limited to a furuncle, chronic furunculosis, impetigo, acute osteomyelitis, pneumonia, endocarditis, scalded skin syndrome, toxic shock syndrome, and food poisoning.

The term "inhibit" refers to any decrease, reduction or complete inhibition of biological activity, nucleic acid expression, or protein expression.

"Label" and "detectable label" refer to a molecule capable of detection including, but not limited to radioactive isotopes, fluorophores, chemiluminescent moieties, enzymes, enzyme substrates, enzyme cofactors, enzyme inhibitors, dyes, metal ions, ligands (e.g., biotin or haptens) and the like. "Fluorophore" refers to a substance or a portion thereof which is capable of exhibiting fluorescence in the detectable range. Particular examples of labels which may be used under the invention include fluorescein, rhodamine, dansyl, umbelliferone, Texas red, luminol, NADPH, alpha- or beta-galactosidase and horseradish peroxidase.

As used herein with respect to genes, the term "mutant" refers to a gene which encodes a mutant protein. As used herein with respect to proteins, the term "mutant" means a protein which does not perform its usual or normal physiological role. S. aureus polypeptide mutants may be produced by amino acid substitutions, deletions or additions. The substitutions, deletions, or additions may involve one or more residues. Especially preferred among these are substitutions, additions and deletions which alter the properties and activities of a S. aureus protein of the present invention.

The terms "polynucleotide" and "nucleic acid" are used interchangeably. They refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term "recombinant" polynucleotide means a polynucleotide of genomic, cDNA, semisynthetic, or synthetic origin which either does not occur in nature or is linked to another polynucleotide in a normatural arrangement. An "oligonucleotide" refers to a single stranded polynucleotide having less than about 100 nucleotides, less than about, e.g., 75, 50, 25, or 10 nucleotides.

The terms "polypeptide", "peptide" and "protein" (if single chain) are used interchangeably herein to refer to polymers of amino acids. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

As used herein, the term "sirABC operon" refers to a group of bacterial genes comprising sirA, sirB, and sirC that share a common promoter. This operon has been found to be important to the iron-restricted growth of S. aureus. Exemplary nucleotide and amino acid sequences of sirABC operon may be found in GenBank Accession No. AY251022 and GenBank Accession No. AF079518. SirA was previously identified as a lipoprotein (Heinrichs et al. (1999) J. Bacterial. 181:1436-1443) and its expression is strictly controlled by the activity of the Fur protein in S. aureus. SirB and SirC encode the transmembrane domains of an ABC-transporter. In particular, mutation of sirA or sirB increases resistance of S. aureus to streptonigrin and results in compromised growth in iron-restricted media. Such mutants are also compromised in the ability to recognize and transport the staphylobactin siderophore into the cell. The terms "SirA", "SirB" and "SirC" encompass fragments or portions thereof and biologically active fragments or portions thereof.

The term "SirABC iron-siderophore transport system" refers the SirABC transporter that is comprised of SirA, SirB, SirC, and FhuC polypeptides.

The terms "Sir protein" or "Sir polypeptide" refer to SirA, SirB and/or SirC proteins. The terms "sir nucleotide", "sir nucleic acid", or "sir gene" refer to sirA, sirB and/or sirC nucleic acids.

The term "Sir deficient strain" refers to a bacterial strain that does not express at least one Sir protein. The term "FhuC deficient strain" refers to a bacterial strain that does not express FhuC.

The term "staphylobactin" refers to the iron-siderophore that is transported into cell by the SirABC iron-siderophore transport system.

The term "small molecule" refers to a compound, which has a molecular weight of less than about 5 kD, less than about 2.5 kD, less than about 1.5 kD, or less than about 0.9 kD. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides or polypeptides.

The term "substantially homologous" when used in connection with amino acid sequences, refers to sequences which are substantially identical to or similar in sequence with each other, giving rise to a homology of conformation and thus to retention, to a useful degree, of one or more biological (including immunological) activities. The term is not intended to imply a common evolution of the sequences.

A "subject" refers to a male or female mammal, including humans.

A "vector" is a self-replicating nucleic acid molecule that transfers an inserted nucleic acid molecule into and/or between host cells. The term includes vectors that function primarily for insertion of a nucleic acid molecule into a cell, replication of vectors that function primarily for the replication of nucleic acid, and expression vectors that function for transcription and/or translation of the DNA or RNA. Also included are vectors that provide more than one of the above functions. As used herein, "expression vectors" are defined as polynucleotides which, when introduced into an appropriate host cell, can be transcribed and translated into a polypeptide(s). An "expression system" usually connotes a suitable host cell comprised of an expression vector that can function to yield a desired expression product.

3. sirA, sirB, sirC, and fhuC Nucleic Acids

The present invention relates to nucleic acid molecules which encode S. aureus SirA, SirB, SirC, and FhuC polypeptides, the full complement thereof, or mutants thereof. FIGS.

6-11 show the nucleic acid sequences that encode SirA, SirB, SirC, and FhuC and the full complement thereof.

Nucleic acids of the present invention may also comprise, consist of or consist essentially of any of the Sir or FhuC nucleotide sequences or the complement thereof as described herein. Yet other nucleic acids comprise, consist of or consist essentially of a nucleotide sequence that has at least about 70%, 80%, 90%, 95%, 98% or 99% identity or homology with a Sir or FhuC gene or the complement thereof described herein. Substantially homologous sequences may be identified using stringent hybridization conditions.

Isolated nucleic acids which differ from the nucleic acids of the invention due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the polypeptides of the invention will exist. One skilled in the art will appreciate that these variations in one or more nucleotides (from less than 1% up to about 3 or 5% or possibly more of the nucleotides) of the nucleic acids encoding a particular protein of the invention may exist among a given species due to natural allelic variation. Any and all such nucleotide variations and resulting amino acid polymorphisms are within the scope of this invention.

Nucleic acids encoding proteins which have amino acid sequences evolutionarily related to a polypeptide disclosed herein are provided, wherein "evolutionarily related to", refers to proteins having different amino acid sequences which have arisen naturally (e.g. by allelic variance or by differential splicing), as well as mutational variants of the proteins of the invention which are derived, for example, by combinatorial mutagenesis.

Fragments of the polynucleotides of the invention encoding a biologically active portion of the subject polypeptides are also provided. As used herein, a fragment of a nucleic acid encoding an active portion of a polypeptide disclosed herein refers to a nucleotide sequence having fewer nucleotides than the nucleotide sequence encoding the full length amino acid sequence of a polypeptide of the invention, and which encodes a given polypeptide that retains at least a portion of a biological activity of the full-length Sir or FhuC protein as defined herein, or alternatively, which is functional as a modulator of the biological activity of the full-length protein. For example, such fragments include a polypeptide containing a domain of the full-length protein from which the polypeptide is derived that mediates the interaction of the protein with another molecule (e.g., polypeptide, DNA, RNA, etc.).

Nucleic acids provided herein may also contain linker sequences, modified restriction endonuclease sites and other sequences useful for molecular cloning, expression or purification of such recombinant polypeptides.

A nucleic acid encoding a Sir or FhuC polypeptide provided herein may be obtained from mRNA or genomic DNA from any organism in accordance with protocols described herein, as well as those generally known to those skilled in the art. A cDNA encoding a polypeptide of the invention, for example, may be obtained by isolating total mRNA from an organism, for example, a bacteria, virus, mammal, etc. Double stranded cDNAs may then be prepared from the total mRNA, and subsequently inserted into a suitable plasmid or bacteriophage vector using any one of a number of known techniques. A gene encoding a polypeptide of the invention may also be cloned using established polymerase chain reaction techniques in accordance with the nucleotide sequence information provided by the invention. In one aspect, methods for amplification of a nucleic acid of the invention, or a fragment thereof may comprise: (a) providing a pair of single stranded oligonucleotides, each of which is at least eight nucleotides in length, complementary to sequences of a nucleic acid of the invention, and wherein the sequences to which the oligonucleotides are complementary are at least ten nucleotides apart; and (b) contacting the oligonucleotides with a sample comprising a nucleic acid comprising the nucleic acid of the invention under conditions which permit amplification of the region located between the pair of oligonucleotides, thereby amplifying the nucleic acid.

The present invention also features recombinant vectors, which include the isolated sir or fhuC nucleic acids, and to host cells containing the recombinant vectors, as well as to methods of making such vectors and host cells and for using them for production of S. aureus polypeptides by recombinant techniques.

Appropriate vectors may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The vector may contain a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred vectors comprise cis-acting control regions to the polynucleotide of interest. Appropriate trans-acting factors may be supplied by the host, supplied by a complementing vector or supplied by the vector itself upon introduction into the host.

In certain embodiments, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating site at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline, kanamycin, or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE9, pQE10 available from Qiagen; pBS vectors, Phagescript vectors, Bluescript vectors, pNH8A, pNH16a, pNH18A, pNH46A available from Stratagene; pET series of vectors available from Novagen; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3, T5 and T7 promoters, the gpt promoter, the lambda PR and PL promoters, the trp promoter and the xyl/tet chimeric promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals (for example, Davis, et al., *Basic Methods In Molecular Biology* (1986)).

Transcription of DNA encoding the polypeptides of the present invention by higher eukaryotes may be increased by inserting an enhancer sequence into the vector. Enhancers are cis-acting elements of DNA, usually about from 10 to 300 nucleotides that act to increase transcriptional activity of a promoter in a given host cell-type. Examples of enhancers include the SV40 enhancer, which is located on the late side of the replication origin at nucleotides 100 to 270, the cytomegalovirus early promoter enhancer, the polyoma enhancer on the late side of the replication origin, and adenovirus enhancers.

For secretion of the translated polypeptide into the lumen of the endoplasmic reticulum, into the periplasmic space or into the extracellular environment, appropriate secretion signals may be incorporated into the expressed polypeptide, for example, the amino acid sequence KDEL. The signals may be endogenous to the polypeptide or they may be heterologous signals. Alternatively, as demonstrated in Example 3, sirA lacking a signal peptide may be cloned into an *E. coli* expression vector to produce large quantities of soluble SirA.

Coding sequences for a polypeptide of interest may be incorporated as a part of a fusion gene including a nucleotide sequence encoding a different polypeptide. The present invention contemplates an isolated nucleic acid comprising a nucleic acid of the invention and at least one heterologous sequence encoding a heterologous peptide linked in frame to the nucleotide sequence of the nucleic acid of the invention so as to encode a fusion protein comprising the heterologous polypeptide. The heterologous polypeptide may be fused to (a) the C-terminus of the polypeptide encoded by the nucleic acid of the invention, (b) the N-terminus of the polypeptide, or (c) the C-terminus and the N-terminus of the polypeptide. In certain instances, the heterologous sequence encodes a polypeptide permitting the detection, isolation, solubilization and/or stabilization of the polypeptide to which it is fused. In still other embodiments, the heterologous sequence encodes a polypeptide selected from the group consisting of a polyHis tag, myc, HA, GST, protein A, protein G, calmodulin-binding peptide, thioredoxin, maltose-binding protein, poly arginine, poly His-Asp, FLAG, a portion of an immunoglobulin protein, and a transcytosis peptide.

Fusion expression systems can be useful when it is desirable to produce an immunogenic fragment of a polypeptide of the invention. For example, the VP6 capsid protein of rotavirus may be used as an immunologic carrier protein for portions of polypeptide, either in the monomeric form or in the form of a viral particle. The nucleic acid sequences corresponding to the portion of a polypeptide of the invention to which antibodies are to be raised may be incorporated into a fusion gene construct which includes coding sequences for a late vaccinia virus structural protein to produce a set of recombinant viruses expressing fusion proteins comprising a portion of the protein as part of the virion. The Hepatitis B surface antigen may also be utilized in this role as well. Similarly, chimeric constructs coding for fusion proteins containing a portion of a polypeptide of the invention and the poliovirus capsid protein may be created to enhance immunogenicity (see, for example, EP Publication NO: 0259149; and Evans et al., (1989) *Nature* 339:385; Huang et al., (1988) *J. Virol.* 62:3855; and Schlienger et al., (1992) *J. Virol.* 66:2).

Fusion proteins may facilitate the expression and/or purification of proteins. For example, a polypeptide of the invention may be generated as a glutathione-S-transferase (GST) fusion protein. Such GST fusion proteins may be used to simplify purification of a polypeptide of the invention, such as through the use of glutathione-derivatized matrices (see, for example, *Current Protocols in Molecular Biology*, eds. Ausubel et al., (N.Y.: John Wiley & Sons, 1991)). In another embodiment, a fusion gene coding for a purification leader sequence, such as a poly-(H is)/enterokinase cleavage site sequence at the N-terminus of the desired portion of the recombinant protein, may allow purification of the expressed fusion protein by affinity chromatography using a $Ni^{2+}$ metal resin. The purification leader sequence may then be subsequently removed by treatment with enterokinase to provide the purified protein (e.g., see Hochuli et al., (1987) *J. Chromatography* 411: 177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which may subsequently be annealed to generate a chimeric gene sequence (see, for example, *Current Protocols in Molecular Biology*, eds. Ausubel et al., John Wiley & Sons: 1992).

In other embodiments, nucleic acids of the invention may be immobilized onto a solid surface, including, plates, microtiter plates, slides, beads, particles, spheres, films, strands, precipitates, gels, sheets, tubing, containers, capillaries, pads, slices, etc. The nucleic acids of the invention may be immobilized onto a chip as part of an array. The array may comprise one or more polynucleotides of the invention as described herein. In one embodiment, the chip comprises one or more polynucleotides of the invention as part of an array of polynucleotide sequences.

Another aspect relates to the use of nucleic acids of the invention in "antisense therapy". As used herein, antisense therapy refers to administration or in situ generation of oligonucleotide probes or their derivatives which specifically hybridize or otherwise bind under cellular conditions with the cellular mRNA and/or genomic DNA encoding one of the polypeptides of the invention so as to inhibit expression of that polypeptide, e.g., by inhibiting transcription and/or translation, and thereby inhibit S. aureus. The binding may be by conventional base pair complementarity, or, for example, in the case of binding to DNA duplexes, through specific interactions in the major groove of the double helix. In general, antisense therapy refers to the range of techniques generally employed in the art, and includes any therapy which relies on specific binding to oligonucleotide sequences.

The oligonucleotide may be conjugated to another molecule, e.g., a peptide, hybridization triggered cross-linking agent transport agent, hybridization-triggered cleavage agent, etc. An antisense molecule can be a "peptide nucleic acid" (PNA). PNA refers to an antisense molecule or antigene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

An antisense construct of the present invention may be delivered, for example, as an expression plasmid which, when transcribed in the cell, produces RNA which is complementary to at least a unique portion of the mRNA which encodes a polypeptide of the invention. Alternatively, the antisense construct may be an oligonucleotide probe which is generated ex vivo and which, when introduced into the cell causes inhibition of expression by hybridizing with the mRNA and/or genomic sequences encoding a polypeptide of the invention. Such oligonucleotide probes may be modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al., (1988) *Biotechniques* 6:958-976; and Stein et al., (1988) *Cancer Res* 48:2659-2668.

In a further aspect, double stranded small interfering RNAs (siRNAs), and methods for administering the same are provided. siRNAs decrease or block gene expression. While not wishing to be bound by theory, it is generally thought that siRNAs inhibit gene expression by mediating sequence specific mRNA degradation. RNA interference (RNAi) is the process of sequence-specific, post-transcriptional gene silencing, particularly in animals and plants, initiated by double-stranded RNA (dsRNA) that is homologous in sequence to the silenced gene (Elbashir et al. Nature 2001; 411(6836): 494-8). Accordingly, it is understood that siRNAs and long dsRNAs having substantial sequence identity to all or a portion of a polynucleotide of the present invention may be used to inhibit the expression of a nucleic acid of the invention.

Alternatively, siRNAs that decrease or block the expression of Sir or FhuC polypeptides described herein may be determined by testing a plurality of siRNA constructs against the target gene. Such siRNAs against a target gene may be chemically synthesized. The nucleotide sequences of the individual RNA strands are selected such that the strand has a region of complementarity to the target gene to be inhibited (i.e., the complementary RNA strand comprises a nucleotide sequence that is complementary to a region of an mRNA transcript that is formed during expression of the target gene, or its processing products, or a region of a (+) strand virus). The step of synthesizing the RNA strand may involve solid-phase synthesis, wherein individual nucleotides are joined end to end through the formation of internucleotide 3'-5' phosphodiester bonds in consecutive synthesis cycles.

Provided herein are siRNA molecules comprising a nucleotide sequence consisting essentially of a sequence of a Sir or FhuC nucleic acid as described herein. An siRNA molecule may comprise two strands, each strand comprising a nucleotide sequence that is at least essentially complementary to each other, one of which corresponds essentially to a sequence of a target gene. The sequence that corresponds essentially to a sequence of a target gene is referred to as the "sense target sequence" and the sequence that is essentially complementary thereto is referred to as the "antisense target sequence" of the siRNA. The sense and antisense target sequences may be from about 15 to about 30 consecutive nucleotides long; from about 19 to about 25 consecutive nucleotides; from about 19 to 23 consecutive nucleotides or about 19, 20, 21, 22 or 23 nucleotides long. The length of the sense and antisense sequences is determined so that an siRNA having sense and antisense target sequences of that length is capable of inhibiting expression of a target gene, preferably without significantly inducing a host interferon response.

In one embodiment of the present invention, siRNA molecules that inhibit FhuC expression are provided. Such siRNA molecules correspond to a portion of the FhuC gene or FhuC mRNA and function to inhibit transcription or translation of the gene. Suitable FhuC-inhibiting siRNA molecules, for example, correspond with a region within about the first 400 nucleotides of the FhuC gene/mRNA, or within the untranslated leader sequence prior to the gene/mRNA sequence as shown in SEQ ID NO: 12 or 13 (e.g. nucleotides 1 to about 390). Specific examples of suitable antisense FhuC-inhibiting siRNA molecules are shown in FIG. 12. Other examples include siRNA molecules comprising the sequences illustrated in FIG. 12, i.e. molecules which include additional sequence from the FhuC gene/mRNA, as well as shorter siRNA molecules comprising at least about 15 to about 30 nucleotides derived from the first 400 nucleotides of the FhuC gene/mRNA, such as 15-30 nucleotide regions of the sequences illustrated in FIG. 12. Thus, suitable siRNA molecules comprise at least about 15 nucleotides, preferably at least about 50 nucleotides, such as, for example, at least 100 nucleotides—200 nucleotides.

In addition, siRNA target sequences may be predicted using any of the aligorithms provided on the world wide web at the mmcmanus with the extension web.mit.edu/mmcmanus/www/home1.2files/siRNAs.

The sense target sequence may be essentially or substantially identical to the coding or a non-coding portion, or combination thereof, of a target nucleic acid. For example, the sense target sequence may be essentially complementary to the 5' or 3' untranslated region, promoter, intron or exon of a target nucleic acid or complement thereof. It can also be essentially complementary to a region encompassing the border between two such gene regions.

The nucleotide base composition of the sense target sequence can be about 50% adenines (As) and thymidines (Ts) and 50% cytidines (Cs) and guanosines (Gs). Alternatively, the base composition can be at least 50% Cs/Gs, e.g., about 60%, 70% or 80% of Cs/Gs. Accordingly, the choice of sense target sequence may be based on nucleotide base composition. Regarding the accessibility of target nucleic acids by siRNAs, such can be determined, e.g., as described in Lee et al. (2002) *Nature Biotech.* 19:500. This approach involves the use of oligonucleotides that are complementary to the target nucleic acids as probes to determine substrate accessibility, e.g., in cell extracts. After forming a duplex with the oligonucleotide probe, the substrate becomes susceptible to RNase H. Therefore, the degree of RNase H sensitivity to a given probe as determined, e.g., by PCR, reflects the accessibility of the chosen site, and may be of predictive value for how well a corresponding siRNA would perform in inhibiting transcription from this target gene. One may also use algorithms identifying primers for polymerase chain reaction (PCR) assays or for identifying antisense oligonucleotides for identifying first target sequences.

The sense and antisense target sequences are preferably sufficiently complementary, such that an siRNA comprising both sequences is able to inhibit expression of the target gene, i.e., to mediate RNA interference. For example, the sequences may be sufficiently complementary to permit hybridization under the desired conditions, e.g., in a cell. Accordingly, the sense and antisense target sequences may be at least about 95%, 97%, 98%, 99% or 100% identical and may, e.g., differ in at most 5, 4, 3, 2, 1 or 0 nucleotides.

Sense and antisense target sequences are also preferably sequences that are not likely to significantly interact with sequences other than the target nucleic acid or complement thereof. This can be confirmed by, e.g., comparing the chosen sequence to the other sequences in the genome of the target cell. Sequence comparisons can be performed according to methods known in the art, e.g., using the BLAST algorithm, further described herein. Of course, small scale experiments can also be performed to confirm that a particular first target sequence is capable of specifically inhibiting expression of a target nucleic acid and essentially not that of other genes.

siRNAs may also comprise sequences in addition to the sense and antisense sequences. For example, an siRNA may be an RNA duplex consisting of two strands of RNA, in which at least one strand has a 3' overhang. The other strand can be blunt-ended or have an overhang. In the embodiment in which the RNA molecule is double stranded and both strands comprise an overhang, the length of the overhangs may be the same or different for each strand. In a particular embodiment, an siRNA comprises sense and antisense sequences, each of which are on one RNA strand, consisting of about 19-25 nucleotides which are paired and which have overhangs of from about 1 to about 3, particularly about 2, nucleotides on both 3' ends of the RNA. In order to further enhance the stability of the RNA of the present invention, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly may also enhance the nuclease resistance of the overhang at least in tissue culture medium. RNA strands of siRNAs may have a 5' phosphate and a 3' hydroxyl group.

In one embodiment, an siRNA molecule comprises two strands of RNA forming a duplex. In another embodiment, an siRNA molecule consists of one RNA strand forming a hairpin loop, wherein the sense and antisense target sequences hybridize and the sequence between the two target sequences is a spacer sequence that essentially forms the loop of the hairpin structure. The spacer sequence may be any combination of nucleotides and any length provided that two complementary oligonucleotides linked by a spacer having this sequence can form a hairpin structure, wherein at least part of the spacer forms the loop at the closed end of the hairpin. For example, the spacer sequence can be from about 3 to about 30 nucleotides; from about 3 to about 20 nucleotides; from about 5 to about 15 nucleotides; from about 5 to about 10 nucleotides; or from about 3 to about 9 nucleotides. The sequence can be any sequence, provided that it does not interfere with the formation of a hairpin structure. In particular, the spacer sequence is preferably not a sequence having any significant homology to the first or the second target sequence, since this might interfere with the formation of a hairpin structure. The spacer sequence is also preferably not similar to other sequences, e.g., genomic sequences of the cell into which the nucleic acid will be introduced, since this may result in undesirable effects in the cell.

A person of skill in the art will understand that when referring to a nucleic acid, e.g., an RNA, the RNA may comprise or consist of naturally occurring nucleotides or of nucleotide derivatives that provide, e.g., more stability to the nucleic acid. Any derivative is permitted provided that the nucleic acid is capable of functioning in the desired fashion. For example, an siRNA may comprise nucleotide derivatives provided that the siRNA is still capable of inhibiting expression of the target gene.

For example, siRNAs may include one or more modified base and/or a backbone modified for stability or for other reasons. For example, the phosphodiester linkages of natural RNA may be modified to include at least one of a nitrogen or sulphur heteroatom. Moreover, siRNA comprising unusual bases, such as inosine, or modified bases, such as tritylated bases, to name just two examples, can be used in the invention. It will be appreciated that a great variety of modifications have been made to RNA that serve many useful purposes known to those of skill in the art. The term siRNA as it is employed herein embraces such chemically, enzymatically or metabolically modified forms of siRNA, provided that it is derived from an endogenous template.

There is no limitation on the manner in which an siRNA may be synthesized. Thus, it may synthesized in vitro or in vivo, using manual and/or automated procedures. In vitro synthesis may be chemical or enzymatic, for example using cloned RNA polymerase (e.g., T3, T7, SP6) for transcription of a DNA (or cDNA) template, or a mixture of both. SiRNAs may also be prepared by synthesizing each of the two strands, e.g., chemically, and hybridizing the two strands to form a duplex. In vivo, the siRNA may be synthesized using recombinant techniques well known in the art (see e.g., Sambrook, et al., Molecular Cloning: A Laboratory Manual, Second Edition (1989); DNA Cloning, Volumes I and II (D. N Glover ed. 1985); Oligonucleotide Synthesis (M. J. Gait ed, 1984); Nucleic Acid Hybridisation (B. D. Hames & S. J. Higgins eds. 1984); Transcription and Translation (B. D. Hames & S. J. Higgins eds. 1984); Animal Cell Culture (R. I. Freshney ed. 1986); Immobilised Cells and Enzymes (IRL Press, 1986); B. Perbal, A Practical Guide to Molecular Cloning (1984); the series, Methods in Enzymology (Academic Press, Inc.); Gene Transfer Vectors for Mammalian Cells (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), Immunochemical Methods in Cell and Molecular Biology (Academic Press, London), Scopes, (1987), Protein Purification: Principles and Practice, Second Edition (Springer-Verlag, N.Y.), and Handbook of Experimental Immunology, Volumes I-IV (D. M. Weir and C. C. Blackwell eds 1986). For example, bacterial cells can be transformed with an expression vector which comprises the DNA template from which the siRNA is to be derived.

If synthesized outside the cell, the siRNA may be purified prior to introduction into the cell. Purification may be by extraction with a solvent (such as phenol/chloroform) or resin, precipitation (for example in ethanol), electrophoresis, chromatography, or a combination thereof. However, purification may result in loss of siRNA and may therefore be minimal or not carried out at all. The siRNA may be dried for storage or dissolved in an aqueous solution, which may contain buffers or salts to promote annealing, and/or stabilization of the RNA strands.

The double-stranded structure may be formed by a single self-complementary RNA strand or two separate complementary RNA strands.

It is known that mammalian cells can respond to extracellular siRNA and therefore may have a transport mechanism for dsRNA (Asher et al. (1969) Nature 223 715-717). Thus, siRNA may be administered extracellularly into a cavity, interstitial space, into the circulation of a mammal, or introduced orally. Methods for oral introduction include direct mixing of the RNA with food of the mammal, as well as engineered approaches in which a species that is used as food is engineered to express the RNA, then fed to the mammal to be affected. For example, food bacteria, such as Lactococcus lactis, may be transformed to produce the dsRNA (see WO93/17117, WO97/14806). Vascular or extravascular circulation, the blood or lymph systems and the cerebrospinal fluid are sites where the RNA may be injected.

RNA may be introduced into the cell intracellularly. Physical methods of introducing nucleic acids may also be used in this respect. siRNA may be administered using the microinjection techniques described in Zernicka-Goetz et al. (1997) Development 124, 1133-1137 and Wianny et al. (1998) Chromosoma 107, 430-439.

Other physical methods of introducing nucleic acids intracellularly include bombardment by particles covered by the siRNA, for example gene gun technology in which the siRNA is immobilized on gold particles and fired directly at the site of wounding. Thus, the invention provides the use of an siRNA in a gene gun for inhibiting the expression of a target gene. Further, there is provided a composition suitable for gene gun therapy comprising an siRNA and gold particles. An alternative physical method includes electroporation of cell membranes in the presence of the siRNA. This method permits RNAi on a large scale. Other methods known in the art for introducing nucleic acids to cells may be used, such as lipid-mediated carrier transport, chemical-mediated transport, such as calcium phosphate, and the like. siRNA may be introduced along with components that perform one or more of the following activities: enhance RNA uptake by the cell, promote annealing of the duplex strands, stabilize the annealed strands, or otherwise increase inhibition of the target gene.

Any known gene therapy technique can be used to administer the RNA. A viral construct packaged into a viral particle would accomplish both efficient introduction of an expression construct into the cell and transcription of siRNA encoded by the expression construct. Thus, siRNA can also be produced inside a cell. Vectors, e.g., expression vectors that comprise a nucleic acid encoding one or the two strands of an siRNA molecule may be used for that purpose. The nucleic acid may further comprise an antisense sequence that is essentially complementary to the sense target sequence. The nucleic acid may further comprise a spacer sequence between the sense and the antisense target sequence. The nucleic acid may further comprise a promoter for directing expression of the sense and antisense sequences in a cell, e.g., an RNA Polymerase II or III promoter and a transcriptional termination signal. The sequences may be operably linked.

In one embodiment a nucleic acid comprises an RNA coding region (e.g., sense or antisense target sequence) operably linked to an RNA polymerase III promoter. The RNA coding region can be immediately followed by a pol III terminator sequence, which directs termination of RNA synthesis by pol III. The pol III terminator sequences generally have 4 or more consecutive thymidine ("T") residues. In a preferred embodiment, a cluster of 5 consecutive T residues is used as the terminator by which pol III transcription is stopped at the second or third T of the DNA template, and thus only 2 to 3 uridine ("U") residues are added to the 3' end of the coding sequence. A variety of pol III promoters can be used with the invention, including, for example, the promoter fragments derived from H1 RNA genes or U6 snRNA genes of human or mouse origin or from any other species. In addition, pol III promoters can be modified/engineered to incorporate other desirable properties such as the ability to be induced by small chemical molecules, either ubiquitously or in a tissue-specific manner. For example, in one embodiment the promoter may be activated by tetracycline. In another embodiment the promoter may be activated by IPTG (lad system).

siRNAs can be produced in cells by transforming cells with two nucleic acids, e.g., vectors, each nucleic acid comprising an expressing cassette, each expression cassette comprising a promoter, an RNA coding sequence (one being a sense target sequence and the other being an antisense target sequence) and a termination signal. Alternatively, a single nucleic acid may comprise these two expression cassettes. In yet another embodiment, a nucleic acid encodes a single stranded RNA comprising a sense target sequence linked to a spacer linked to an antisense target sequence. The nucleic acids may be present in a vector, such as an expression vector, e.g., a eukaryotic expression vector that allows expression of the sense and antisense target sequences in cells into which it is introduced.

Vectors for producing siRNAs are described, e.g., in Paul et al. (2002) Nature Biotechnology 29:505; Xia et al. (2002) Nature Biotechnology 20:1006; Zeng et al. (2002) Mol. Cell 9:1327; Thijn et al. (2002) Science 296:550; BMC Biotechnol. 2002 Aug. 28; 2(1):15; Lee et al. (2002) Nature Biotechnology 19: 500; McManus et al. (2002) RNA 8:842; Miyagishi et al. (2002) Nature Biotechnology 19:497; Sui et al. (2002) PNAS 99:5515; Yu et al. (2002) PNAS 99:6047; Shi et al. (2003) Trends Genet. 19(1):9; Gaudilliere et al. (2002) J. Biol. Chem. 277(48):46442; US2002/0182223; US 2003/0027783; WO 01/36646 and WO 03/006477. Vectors are also available commercially. For example, the pSilencer is available from Gene Therapy Systems, Inc. and pSUPER RNAi system is available from Oligoengine.

Also provided herein are compositions comprising one or more siRNA or nucleic acid encoding an RNA coding region of an siRNA. Compositions may be pharmaceutical compositions and comprise a pharmaceutically acceptable carrier. Compositions may also be provided in a device for administering the composition in a cell or in a subject. For example a composition may be present in a syringe or on a stent. A composition may also comprise agents facilitating the entry of the siRNA or nucleic acid into a cell.

In general, the oligonucleotides may be synthesized using protocols known in the art, for example, as described in Caruthers et al., *Methods in Enzymology* (1992) 211:3-19; Thompson et al., International PCT Publication No. WO 99/54459; Wincott et al., *Nucl. Acids Res.* (1995) 23:2677-2684; Wincott et al., *Methods Mol. Bio.*, (1997) 74:59; Brennan et al., *Biotechnol. Bioeng.* (1998) 61:33-45; and Brennan, U.S. Pat. No. 6,001,311; each of which is hereby incorporated by reference in its entirety herein. In general, the synthesis of oligonucleotides involves conventional nucleic acid protecting and coupling groups, such as dimethoxytrityl at the 5'-end, and phosphoramidites at the 3'-end. In a non-limiting example, small scale syntheses are conducted on a Expedite 8909 RNA synthesizer sold by Applied Biosystems, Inc. (Weiterstadt, Germany), using ribonucleoside phosphoramidites sold by ChemGenes Corporation (Ashland Technology Center, 200 Horner Avenue, Ashland, Mass. 01721, USA). Alternatively, syntheses can be performed on a 96-well plate synthesizer, such as the instrument produced by Protogene (Palo Alto, Calif., USA), or by methods such as those described in Usman et al., *J. Am. Chem. Soc.* (1987) 109: 7845; Scaringe et al., *Nucl. Acids Res.* (1990) 18:5433; Wincott et al., *Nucl. Acids Res.* (1990) 23:2677-2684; and Wincott et al., *Methods Mol. Bio.* (1997) 74:59, each of which is hereby incorporated by reference in its entirety.

The nucleic acid molecules of the present invention may be synthesized separately and dsRNAs may be formed post-synthetically, for example, by ligation (Moore et al., *Science* (1992) 256:9923; Draper et al., International PCT publication No. WO 93/23569; Shabarova et al., *Nucl. Acids Res.* (1991) 19:4247; Bellon et al., *Nucleosides & Nucleotides* (1997) 16:951; and Bellon et al., *Bioconjugate Chem.* (1997) 8:204; or by hybridization following synthesis and/or deprotection. The nucleic acid molecules can be purified by gel electrophoresis using conventional methods or can be purified by high pressure liquid chromatography (HPLC; see Wincott et al., supra, the totality of which is hereby incorporated herein by reference) and re-suspended in water.

In another embodiment, the level of a particular mRNA or polypeptide in a cell is reduced by introduction of a ribozyme into the cell or nucleic acid encoding such. Ribozyme molecules designed to catalytically cleave mRNA transcripts can also be introduced into, or expressed, in cells to inhibit expression of gene Y (see, e.g., Sarver et al., 1990, *Science* 247:1222-1225 and U.S. Pat. No. 5,093,246). One commonly used ribozyme motif is the hammerhead, for which the substrate sequence requirements are minimal. Design of the hammerhead ribozyme is disclosed in Usman et al., *Current Opin. Struct. Biol.* (1996) 6:527-533. Usman also discusses the therapeutic uses of ribozymes. Ribozymes can also be prepared and used as described in Long et al., *FASEB J.* (1993) 7:25; Symons, *Ann. Rev. Biochem.* (1992) 61:641; Perrotta et al., *Biochem.* (1992) 31:16-17; Ojwang et al., *Proc. Natl. Acad. Sci.* (*USA*) (1992) 89:10802-10806; and U.S. Pat. No. 5,254,678. Ribozyme cleavage of HIV-I RNA is described in U.S. Pat. No. 5,144,019; methods of cleaving RNA using ribozymes is described in U.S. Pat. No. 5,116,742; and methods for increasing the specificity of ribozymes are described in U.S. Pat. No. 5,225,337 and Koizumi et al., *Nucleic Acid Res.* (1989) 17:7059-7071. Preparation and use of ribozyme fragments in a hammerhead structure are also described by Koizumi et al., *Nucleic Acids Res.* (1989) 17:7059-7071. Preparation and use of ribozyme fragments in a hairpin structure are described by Chowrira and Burke, *Nucleic Acids Res.* (1992) 20:2835. Ribozymes can also be made by rolling transcription as described in Daubendiek and Kool, *Nat. Biotechnol.* (1997) 15(3):273-277.

Gene expression can be reduced by targeting deoxyribonucleotide sequences complementary to the regulatory region of the target gene (i.e., the gene promoter and/or enhancers) to form triple helical structures that prevent transcription of the gene in target cells in the body. (See generally, Helene (1991) *Anticancer Drug Des.*, 6(6):569-84; Helene et al. (1992) *Ann. N.Y. Acad. Sci.*, 660:27-36; and Maher (1992) *Bioassays* 14(12):807-15).

In a further embodiment, RNA aptamers can be introduced into or expressed in a cell. RNA aptamers are specific RNA ligands for proteins, such as for Tat and Rev RNA (Good et al. (1997) *Gene Therapy* 4: 45-54) that can specifically inhibit their translation.

4. SirA, SirB, SirC, and FhuC Polypeptides

SirA, SirB, SirC, and FhuC polypeptides described herein include naturally purified products, products of chemical synthetic procedures, and products produced by recombinant techniques from a prokaryotic or eukaryotic host cell, including, for example, bacterial, yeast, higher plant, insect and mammalian cells. Knowledge of these polypeptides is useful in the provision of methods to inhibit the polypeptides, by inhibiting either polypeptide expression or polypeptide activity, and thereby inhibit *S. aureus*. In certain embodiments, the polypeptides disclosed herein inhibit the function of Sir polypeptides and FhuC.

Polypeptides may also comprise, consist of or consist essentially of an amino acid sequence encoded by a nucleotide sequence as shown in FIGS. 6-11. Exemplary polypeptide sequences for SirA, SirB, SirC, and FhuC are shown in FIGS. 7-9 and 11, respectively. Yet other polypeptides comprise, consist of or consist essentially of an amino acid sequence that has at least about 70%, 80%, 90%, 95%, 98% or 99% identity or homology with the Sir or FhuC polypeptides described herein. For example, polypeptides that differ from a sequence in a naturally occurring protein in about 1, 2, 3, 4, 5 or more amino acids are also contemplated. The differences may be substitutions, e.g., conservative substitutions, deletions or additions. The differences are preferably in regions that are not significantly conserved among different species. Such regions can be identified by aligning the amino acid sequences from various species. These amino acids can be substituted, e.g., with those found in another species. Other amino acids that may be substituted, inserted or deleted at these or other locations can be identified by mutagenesis studies coupled with biological assays.

Other proteins that are encompassed herein are those that comprise modified amino acids. Exemplary proteins are derivative proteins that may be one modified by glycosylation, pegylation, phosphorylation or any similar process that retains at least one biological function of the protein from which it was derived.

Proteins may also comprise one or more non-naturally occurring amino acids. For example, nonclassical amino acids or chemical amino acid analogs can be introduced as a substitution or addition into proteins. Non-classical amino acids include, but are not limited to, the D-isomers of the common amino acids, 2,4-diaminobutyric acid, alpha-amino isobutyric acid, 4-aminobutyric acid, Abu, 2-amino butyric acid, gamma-Abu, epsilon-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, beta-alanine, fluoro-amino acids, designer amino acids such as beta-methyl amino acids, Calpha-methyl amino acids, Nalpha-methyl amino acids, and amino acid analogs in general. Furthermore, the amino acid can be D (dextrorotary) or L (levorotary).

In certain embodiments, a Sir or FhuC polypeptide described herein may be a fusion protein containing a domain which increases its solubility and/or facilitates its purification, identification, detection, and/or structural characterization. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, a polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

The S. aureus polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, lectin chromatography and high performance liquid chromatography ("HPLC") is employed for purification. Proteins may be used as a substantially pure preparation, e.g., wherein at least about 90% of the protein in the preparation are the desired protein. Compositions comprising at least about 50%, 60%, 70%, or 80% of the desired protein may also be used.

In certain embodiments, polypeptides of the invention may be synthesized chemically, ribosomally in a cell free system, or ribosomally within a cell. Chemical synthesis of polypeptides of the invention may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and Muir et al., Curr. Opin. Biotech. (1993): vol. 4, p 420; Miller et al., Science (1989): vol. 246, p 1149; Wlodawer et al., Science (1989): vol. 245, p 616; Huang et al., Biochemistry (1991): vol. 30, p 7402; Schnolzer, et al., Int. J. Pept. Prot. Res. (1992): vol. 40, p 180-193; Rajarathnam et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; Wallace et al., J. Biol. Chem. (1992): vol. 267, p 3852; Abrahmsen et al., Biochemistry (1991): vol. 30, p 4151; Chang, et al., Proc. Natl. Acad. Sci. USA (1994) 91: 12544-12548; Schnlzer et al., Science (1992): vol., 3256, p 221; and Akaji et al., Chem. Pharm. Bull. (Tokyo) (1985) 33: 184).

In certain embodiments, it may be advantageous to provide naturally-occurring or experimentally-derived homologs of a polypeptide of the invention. Such homologs may function in a limited capacity as a modulator to promote or inhibit a subset of the biological activities of the naturally-occurring form of the polypeptide. Thus, specific biological effects may be elicited by treatment with a homolog of limited function, and with fewer side effects relative to treatment with agonists or antagonists which are directed to all of the biological activities of a polypeptide of the invention. For instance, antagonistic homologs may be generated which interfere with the ability of the wild-type polypeptide of the invention to associate with certain proteins, but which do not substantially interfere with the formation of complexes between the native polypeptide and other cellular proteins.

Polypeptides may be derived from the full-length polypeptides of the invention. Isolated peptidyl portions of those polypeptides may be obtained by screening polypeptides recombinantly produced from the corresponding fragment of the nucleic acid encoding such polypeptides. In addition, fragments may be chemically synthesized using techniques known in the art such as conventional Merrifield solid phase f-Moc or t-Boc chemistry. For example, proteins may be arbitrarily divided into fragments of desired length with no overlap of the fragments, or may be divided into overlapping fragments of a desired length. The fragments may be produced (recombinantly or by chemical synthesis) and tested to identify those peptidyl fragments having a desired property, for example, the capability of functioning as a modulator of the polypeptides of the invention. In an illustrative embodiment, peptidyl portions of a protein of the invention may be tested for binding activity, as well as inhibitory ability, by expression as, for example, thioredoxin fusion proteins, each of which contains a discrete fragment of a protein of the invention (see, for example, U.S. Pat. Nos. 5,270,181 and 5,292,646; and PCT publication WO94/02502).

In another embodiment, truncated polypeptides may be prepared. Truncated polypeptides have from 1 to 20 or more amino acid residues removed from either or both the N- and C-termini. Such truncated polypeptides may prove more amenable to expression, purification or characterization than the full-length polypeptide. For example, truncated polypeptides may prove more amenable than the full-length polypeptide to crystallization, to yielding high quality diffracting crystals or to yielding an HSQC spectrum with high intensity peaks and minimally overlapping peaks. In addition, the use of truncated polypeptides may also identify stable and active domains of the full-length polypeptide that may be more amenable to characterization.

It is also possible to modify the structure of the polypeptides of the invention for such purposes as enhancing therapeutic or prophylactic efficacy, or stability (e.g., ex vivo shelf life, resistance to proteolytic degradation in vivo, etc.). Such modified polypeptides, when designed to retain at least one activity of the naturally-occurring form of the protein, are considered "functional equivalents" of the polypeptides described in more detail herein. Such modified polypeptides may be produced, for instance, by amino acid substitution, deletion, or addition, which substitutions may consist in whole or part by conservative amino acid substitutions.

For instance, it is reasonable to expect that an isolated conservative amino acid substitution, such as replacement of a leucine with an isoleucine or valine, an aspartate with a glutamate, a threonine with a serine, will not have a major affect on the biological activity of the resulting molecule. Whether a change in the amino acid sequence of a polypeptide results in a functional homolog may be readily determined by assessing the ability of the variant polypeptide to produce a response similar to that of the wild-type protein. Polypeptides in which more than one replacement has taken place may readily be tested in the same manner.

Methods of generating sets of combinatorial mutants of polypeptides of the invention are provided, as well as truncation mutants, and is especially useful for identifying potential variant sequences (e.g., homologs). The purpose of screening such combinatorial libraries is to generate, for example, homologs which may modulate the activity of a polypeptide of the invention, or alternatively, which possess novel activities altogether. Combinatorially-derived homologs may be generated which have a selective potency relative to a naturally-occurring protein. Such homologs may be used in the development of therapeutics.

Likewise, mutagenesis may give rise to homologs which have intracellular half-lives dramatically different than the corresponding wild-type protein. For example, the altered protein may be rendered either more stable or less stable to proteolytic degradation or other cellular process which result in destruction of, or otherwise inactivation of the protein. Such homologs, and the genes which encode them, may be utilized to alter protein expression by modulating the half-life of the protein. As above, such proteins may be used for the development of therapeutics or treatment.

In similar fashion, protein homologs may be generated by the present combinatorial approach to act as antagonists, in that they are able to interfere with the activity of the corresponding wild-type protein.

In a representative embodiment of this method, the amino acid sequences for a population of protein homologs are aligned, preferably to promote the highest homology possible. Such a population of variants may include, for example, homologs from one or more species, or homologs from the same species but which differ due to mutation. Amino acids which appear at each position of the aligned sequences are selected to create a degenerate set of combinatorial sequences. In certain embodiments, the combinatorial library is produced by way of a degenerate library of genes encoding a library of polypeptides which each include at least a portion of potential protein sequences. For instance, a mixture of synthetic oligonucleotides may be enzymatically ligated into gene sequences such that the degenerate set of potential nucleotide sequences are expressible as individual polypeptides, or alternatively, as a set of larger fusion proteins (e.g. for phage display).

There are many ways by which the library of potential homologs may be generated from a degenerate oligonucleotide sequence. Chemical synthesis of a degenerate gene sequence may be carried out in an automatic DNA synthesizer, and the synthetic genes may then be ligated into an appropriate vector for expression. One purpose of a degenerate set of genes is to provide, in one mixture, all of the sequences encoding the desired set of potential protein sequences. The synthesis of degenerate oligonucleotides is well known in the art (see for example, Narang (1983) *Tetrahedron* 39:3; Itakura et al. (1981) *Recombinant DNA, Proc. 3rd Cleveland Sympos. Macromolecules*, ed. AG Walton, Amsterdam: Elsevier pp. 273-289; Itakura et al. (1984) *Annu. Rev. Biochem.* 53:323; Itakura et al. (1984) *Science* 198:1056; Ike et al., (1983) *Nucleic Acid Res.* 11:477). Such techniques have been employed in the directed evolution of other proteins (see, for example, Scott et al. (1990) *Science* 249:386-390; Roberts et al. (1992) *PNAS USA* 89:2429-2433; Devlin et al. (1990) *Science* 249: 404-406; Cwirla et al. (1990) *PNAS USA* 87: 6378-6382; as well as U.S. Pat. Nos. 5,223,409, 5,198,346, and 5,096,815).

Alternatively, other forms of mutagenesis may be utilized to generate a combinatorial library. For example, protein homologs (both agonist and antagonist forms) may be generated and isolated from a library by screening using, for example, alanine scanning mutagenesis and the like (Ruf et al. (1994) *Biochemistry* 33:1565-1572; Wang et al. (1994) *J. Biol. Chem.* 269:3095-3099; Balint et al. (1993) *Gene* 137: 109-118; Grodberg et al. (1993) *Eur. J. Biochem.* 218:597-601; Nagashima et al. (1993) *J. Biol. Chem.* 268:2888-2892; Lowman et al. (1991) *Biochemistry* 30:10832-10838; and Cunningham et al., (1989) *Science* 244:1081-1085), by linker scanning mutagenesis (Gustin et al. (1993) *Virology* 193:653-660; Brown et al. (1992) *Mol. Cell Biol.* 12:2644-2652; McKnight et al. (1982) *Science* 232:316); by saturation mutagenesis (Meyers et al. (1986) *Science* 232:613); by PCR mutagenesis (Leung et al. (1989) *Method Cell Mol Biol* 1:11-19); or by random mutagenesis (Miller et al. (1992) A Short Course in Bacterial Genetics, CSHL Press, Cold Spring Harbor, N.Y.; and Greener et al. (1994) *Strategies in Mol Biol* 7:32-34). Linker scanning mutagenesis, particularly in a combinatorial setting, is an attractive method for identifying truncated forms of proteins that are bioactive.

A wide range of techniques are known in the art for screening gene products of combinatorial libraries made by point mutations and truncations, and for screening cDNA libraries for gene products having a certain property. Such techniques will be generally adaptable for rapid screening of the gene libraries generated by the combinatorial mutagenesis of protein homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

In an illustrative embodiment of a screening assay, candidate combinatorial gene products are displayed on the surface of a cell and the ability of particular cells or viral particles to bind to the combinatorial gene product is detected in a "panning assay". For instance, the gene library may be cloned into the gene for a surface membrane protein of a bacterial cell (Ladner et al., WO 88/06630; Fuchs et al., (1991) *Bio/Technology* 9:1370-1371; and Goward et al., (1992) *TIBS* 18:136-140), and the resulting fusion protein detected by panning, e.g. using a fluorescently labeled molecule which binds the cell surface protein, e.g. FITC-substrate, to score for potentially functional homologs. Cells may be visually inspected and separated under a fluorescence microscope, or, when the morphology of the cell permits, separated by a fluorescence-activated cell sorter. This method may be used to identify substrates or other polypeptides that can interact with a polypeptide of the invention.

In similar fashion, the gene library may be expressed as a fusion protein on the surface of a viral particle. For instance, in the filamentous phage system, foreign peptide sequences may be expressed on the surface of infectious phage, thereby conferring two benefits. First, because these phage may be applied to affinity matrices at very high concentrations, a large number of phage may be screened at one time. Second, because each infectious phage displays the combinatorial gene product on its surface, if a particular phage is recovered from an affinity matrix in low yield, the phage may be amplified by another round of infection. The group of almost identical *E. coli* filamentous phages M13, fd, and fl are most often used in phage display libraries, as either of the phage gIII or gVIII coat proteins may be used to generate fusion proteins without disrupting the ultimate packaging of the viral particle (Ladner et al., PCT publication WO 90/02909; Garrard et al., PCT publication WO 92/09690; Marks et al., (1992) *J. Biol. Chem.* 267:16007-16010; Griffiths et al., (1993) *EMBO J.* 12:725-734; Clackson et al., (1991) *Nature* 352:624-628; and Barbas et al., (1992) *PNAS* USA 89:4457-4461). Other phage coat proteins may be used as appropriate.

The polypeptides disclosed herein may be reduced to generate mimetics, e.g. peptide or non-peptide agents, which are able to mimic binding of the authentic protein to another cellular partner. Such mutagenic techniques as described above, as well as the thioredoxin system, are also particularly useful for mapping the determinants of a protein which participates in a protein-protein interaction with another protein. To illustrate, the critical residues of a protein which are involved in molecular recognition of a substrate protein may be determined and used to generate peptidomimetics that may bind to the substrate protein. The peptidomimetic may then be used as an inhibitor of the wild-type protein by binding to the substrate and covering up the critical residues needed for interaction with the wild-type protein, thereby preventing interaction of the protein and the substrate. By employing, for example, scanning mutagenesis to map the amino acid residues of a protein which are involved in binding a substrate polypeptide, peptidomimetic compounds may be generated which mimic those residues in binding to the substrate.

For instance, derivatives of the Sir proteins and FhuC protein described herein may be chemically modified peptides and peptidomimetics. Peptidomimetics are compounds based on, or derived from, peptides and proteins. Peptidomimetics can be obtained by structural modification of known peptide sequences using unnatural amino acids, conformational restraints, isosteric replacement, and the like. The subject peptidomimetics constitute the continum of structural space between peptides and non-peptide synthetic structures; peptidomimetics may be useful, therefore, in delineating pharmacophores and in helping to translate peptides into nonpeptide compounds with the activity of the parent peptides.

Moreover, mimetopes of the subject peptides can be provided. Such peptidomimetics can have such attributes as being non-hydrolyzable (e.g., increased stability against proteases or other physiological conditions which degrade the corresponding peptide), increased specificity and/or potency for stimulating cell differentiation. For illustrative purposes, non-hydrolyzable peptide analogs of such residues may be generated using benzodiazepine (e.g., see Freidinger et al., in *Peptides: Chemistry and Biology*, G. R. Marshall ed., ESCOM Publisher: Leiden, Netherlands, 1988), azepine (e.g., see Huffman et al., in *Peptides: Chemistry and Biology*, G. R. Marshall ed., ESCOM Publisher: Leiden, Netherlands, 1988), substituted gamma lactam rings (Garvey et al., in *Peptides: Chemistry and Biology*, G. R. Marshall ed., ESCOM Publisher: Leiden, Netherlands, 1988), keto-methylene pseudopeptides (Ewenson et al., (1986) *J. Med. Chem.* 29:295; and Ewenson et al., in *Peptides: Structure and Function* (Proceedings of the 9th American Peptide Symposium) Pierce Chemical Co. Rockland, Ill., 1985), 13-turn dipeptide cores (Nagai et al., (1985) *Tetrahedron Lett* 26:647; and Sato et al., (1986) *J Chem Soc Perkin Trans* 1:1231), and β-aminoalcohols (Gordon et al., (1985) *Biochem Biophys Res Commun* 126:419; and Dann et al., (1986) *Biochem Biophys Res Commun* 134:71).

In addition to a variety of sidechain replacements which can be carried out to generate peptidomimetics, the description specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

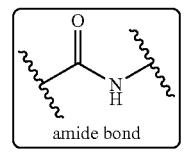 [SMILES: *NC(*)=O]
amide bond

Examples of Surrogates

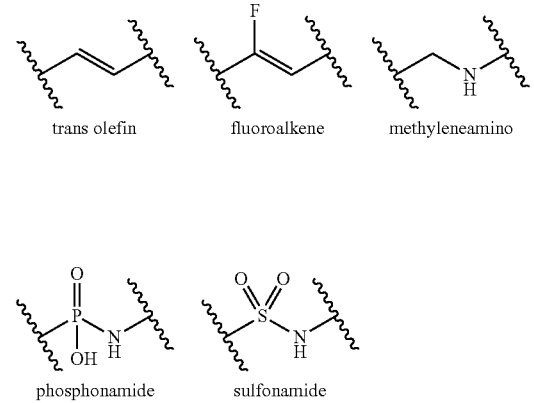

trans olefin    fluoroalkene    methyleneamino phosphonamide    sulfonamide

Additionally, peptidomimietics based on more substantial modifications of the backbone of a peptide can be used. Peptidomimetics which fall in this category include (i) retro-inverso analogs, and (ii) N-alkyl glycine analogs (so-called peptoids).

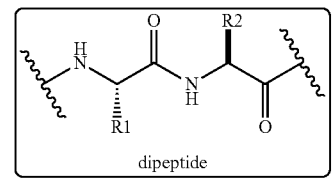
dipeptide

Examples of Analogs

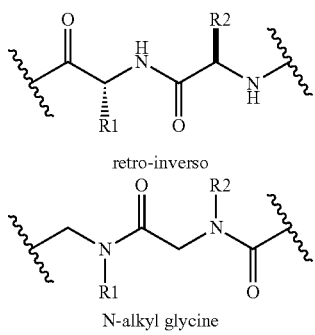

retro-inverso

N-alkyl glycine

Furthermore, the methods of combinatorial chemistry are being brought to bear, on the development of new peptidomimetics. For example, one embodiment of a so-called "peptide morphing" strategy focuses on the random generation of a library of peptide analogs that comprise a wide range of peptide bond substitutes.

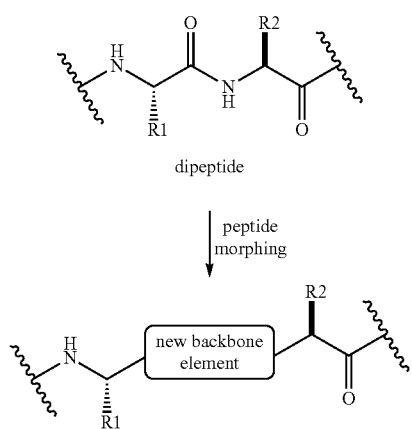

dipeptide peptide morphing

In an exemplary embodiment, the peptidomimetic can be derived as a retro-inverso analog of the peptide. Such retro-inverso analogs can be made according to the methods known in the art, such as that described by the Sisto et al. U.S. Pat. No. 4,522,752. A retro-inverso analog can be generated as described, e.g., in WO 00/01720. It will be understood that a mixed peptide, e.g. including some normal peptide linkages, may be generated. As a general guide, sites which are most susceptible to proteolysis are typically altered, with less susceptible amide linkages being optional for mimetic switching. The final product, or intermediates thereof, can be purified by HPLC.

Peptides may comprise at least one amino acid or every amino acid that is a D stereoisomer. Other peptides may comprise at least one amino acid that is reversed. The amino acid that is reversed may be a D stereoisomer. Every amino acid of a peptide may be reversed and/or every amino acid may be a D stereoisomer.

In another illustrative embodiment, a peptidomimetic can be derived as a retro-enantio analog of a peptide. Retro-enantio analogs such as this can be synthesized with commercially available D-amino acids (or analogs thereof) and standard solid- or solution-phase peptide-synthesis techniques, as described, e.g., in WO 00/01720. The final product may be purified by HPLC to yield the pure retro-enantio analog.

In still another illustrative embodiment, trans-olefin derivatives can be made for the subject peptide. Trans-olefin analogs can be synthesized according to the method of Y. K. Shue et al. (1987) *Tetrahedron Letters* 28:3225 and as described in WO 00/01720. It is further possible to couple pseudodipeptides synthesized by the above method to other pseudodipeptides, to make peptide analogs with several olefinic functionalities in place of amide functionalities.

Still another class of peptidomimetic derivatives include the phosphonate derivatives. The synthesis of such phosphonate derivatives can be adapted from known synthesis schemes. See, for example, Loots et al. in *Peptides: Chemistry and Biology*, (Escom Science Publishers, Leiden, 1988, p. 118); Petrillo et al. in *Peptides: Structure and Function* (Proceedings of the 9th American Peptide Symposium, Pierce Chemical Co. Rockland, Ill., 1985).

Many other peptidomimetic structures are known in the art and can be readily adapted for use in the subject peptidomimetics. To illustrate, a peptidomimetic may incorporate the 1-azabicyclo[4.3.0]nonane surrogate (see Kim et al. (1997) *J. Org. Chem.* 62:2847), or an N-acyl piperazic acid (see Xi et al. (1998) *J. Am. Chem. Soc.* 120:80), or a 2-substituted piperazine moiety as a constrained amino acid analogue (see Williams et al. (1996) *J. Med. Chem.* 39:1345-1348). In still other embodiments, certain amino acid residues can be replaced with aryl and bi-aryl moieties, e.g., monocyclic or bicyclic aromatic or heteroaromatic nucleus, or a biaromatic, aromatic-heteroaromatic, or biheteroaromatic nucleus.

The subject peptidomimetics can be optimized by, e.g., combinatorial synthesis techniques combined with high throughput screening.

Moreover, other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds for compounds capable of inhibiting cell survival and/or tumor growth. A mimetope can also be obtained, for example, from libraries of natural and synthetic compounds, in particular, chemical or combinatorial libraries (i.e., libraries of compounds that differ in sequence or size but that have the same building blocks). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling. The predicted mimetope structures can then be produced by, for example, chemical synthesis, recombinant DNA technology, or by isolating a mimetope from a natural source (e.g., plants, animals, bacteria and fungi).

"Peptides, variants and derivatives thereof" or "peptides and analogs thereof" are included in "peptide therapeutics" and is intended to include any of the peptides or modified forms thereof, e.g., peptidomimetics, described herein. Preferred peptide therapeutics decrease cell survival or increase apoptosis. For example, they may decrease cell survival or increase apoptosis by a factor of at least about 2 fold, 5 fold, 10 fold, 30 fold or 100 fold, as determined, e.g., in an assay described herein.

The activity of a Sir or FhuC protein, fragment, or variant thereof may be assayed using an appropriate substrate or binding partner or other reagent suitable to test for the suspected activity as described below.

In another embodiment, the activity of a polypeptide may be determined by assaying for the level of expression of RNA and/or protein molecules. Transcription levels may be determined, for example, using Northern blots, hybridization to an oligonucleotide array or by assaying for the level of a resulting protein product. Translation levels may be determined, for example, using Western blotting or by identifying a detectable signal produced by a protein product (e.g., fluorescence, luminescence, enzymatic activity, etc.). Depending on the particular situation, it may be desirable to detect the level of transcription and/or translation of a single gene or of multiple genes.

Alternatively, it may be desirable to measure the overall rate of DNA replication, transcription and/or translation in a cell. In general this may be accomplished by growing the cell in the presence of a detectable metabolite which is incorporated into the resultant DNA, RNA, or protein product. For example, the rate of DNA synthesis may be determined by growing cells in the presence of BrdU which is incorporated into the newly synthesized DNA. The amount of BrdU may then be determined histochemically using an anti-BrdU antibody.

In other embodiments, polypeptides of the invention may be immobilized onto a solid surface, including, microtiter plates, slides, beads, films, etc. The polypeptides of the invention may be immobilized onto a "chip" as part of an array. An array, having a plurality of addresses, may comprise one or more polypeptides of the invention in one or more of those addresses. In one embodiment, the chip comprises one or more polypeptides of the invention as part of an array of polypeptide sequences.

In other embodiments, polypeptides of the invention may be immobilized onto a solid surface, including, plates, microtiter plates, slides, beads, particles, spheres, films, strands, precipitates, gels, sheets, tubing, containers, capillaries, pads, slices, etc. The polypeptides of the invention may be immobilized onto a "chip" as part of an array. An array, having a plurality of addresses, may comprise one or more polypeptides of the invention in one or more of those addresses. In one embodiment, the chip comprises one or more polypeptides of the invention as part of an array.

5. Antibodies and Uses Thereof

Antibodies to the polypeptides of the present invention may also be useful to inhibit *S. aureus*, as one of skill in the art will appreciate.

To produce antibodies against the Sir and FhuC polypeptides described herein, host animals may be injected with Sir or FhuC polypeptides or with Sir or FhuC peptides. Hosts may be injected with peptides of different lengths encompassing a desired target sequence. For example, peptide antigens that are at least 5, 10, 15, 20, 25, 30, 35, 40, 45, 50, 55, 60, 65, 70, 75, 80, 85, 90, 95, 100, 105, 110, 115, 120, 125, 130, 135, 140, 145 or 150 amino acids may be used. Alternatively, if a portion of a protein defines an epitope, but is too short to be antigenic, it may be conjugated to a carrier molecule in order to produce antibodies. Some suitable carrier molecules include keyhole limpet hemocyanin, Ig sequences, TrpE, and human or bovine serum albumen. Conjugation may be carried out by methods known in the art. One such method is to combine a cysteine residue of the fragments with a cysteine residue on the carrier molecule.

In addition, antibodies to three-dimensional epitopes, i.e., non-linear epitopes, may also be prepared, based on, e.g., crystallographic data of proteins. Antibodies obtained from that injection may be screened against the short antigens of proteins described herein. Antibodies prepared against a Sir or FhuC peptide may be tested for activity against that peptide as well as the full length Sir or FhuC protein. Antibodies may have affinities of at least about $10^{-6}$M, $10^{-7}$M, $10^{-8}$M, $10^{-9}$M, $10^{-10}$M, $10^{-11}$M or $10^{-12}$M or higher toward the Sir or FhuC peptide and/or the full length Sir or FhuC protein described herein.

Suitable cells for the DNA sequences and host cells for antibody expression and secretion can be obtained from a number of sources, including the American Type Culture Collection ("*Catalogue of Cell Lines and Hybridomas*" 5th edition (1985) Rockville, Md., U.S.A.).

Polyclonal and monoclonal antibodies may be produced by methods known in the art. Monoclonal antibodies may be produced by hybridomas prepared using known procedures including the immunological method described by Kohler and Milstein, *Nature* 1975; 256: 495-7; and Campbell in "Monoclonal Antibody Technology, The Production and Characterization of Rodent and Human Hybridomas" in Burdon et al., Eds. Laboratory Techniques in Biochemistry and Molecular Biology, Volume 13, Elsevier Science Publishers, Amsterdam (1985); as well as by the recombinant DNA method described by Huse et al, *Science* (1989) 246: 1275-81.

Methods of antibody purification are well known in the art. See, for example, Harlow and Lane (1988) *Antibodies: A Laboratory Manual*, Cold Spring Harbor Laboratory, N.Y. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-antibody. Antibodies may also be purified on affinity columns according to methods known in the art.

Other embodiments include functional equivalents of antibodies, and include, for example, chimerized, humanized, and single chain antibodies as well as fragments thereof. Methods of producing functional equivalents are disclosed in PCT Application WO 93/21319; European Patent Application No. 239,400; PCT Application WO 89/09622; European Patent Application 388,745; and European Patent Application EP 332,424.

Functional equivalents include polypeptides with amino acid sequences substantially the same as the amino acid sequence of the variable or hypervariable regions of the antibodies of the invention. "Substantially the same" amino acid sequence is defined herein as a sequence with at least 70%, preferably at least about 80%, and more preferably at least 90% homology to another amino acid sequence as determined by the FASTA search method in accordance with Pearson and Lipman, *Proc Natl Acad Sci USA* (1988) 85: 2444-8.

Chimerized antibodies may have constant regions derived substantially or exclusively from human antibody constant regions and variable regions derived substantially or exclusively from the sequence of the variable region from a mammal other than a human. Humanized antibodies may have constant regions and variable regions other than the complement determining regions (CDRs) derived substantially or exclusively from the corresponding human antibody regions and CDRs derived substantially or exclusively from a mammal other than a human.

Suitable mammals other than a human may include any mammal from which monoclonal antibodies may be made.

Suitable examples of mammals other than a human may include, for example, a rabbit, rat, mouse, horse, goat, or primate.

Antibodies to Sir proteins and FhuC protein as described herein may be prepared as described above. In a further embodiment, the antibodies to the Sir and FhuC proteins described herein (whole antibodies or antibody fragments) may be conjugated to a biocompatible material, such as polyethylene glycol molecules (PEG) according to methods well known to persons of skill in the art to increase the antibody's half-life. See for example, U.S. Pat. No. 6,468,532. Functionalized PEG polymers are available, for example, from Nektar Therapeutics. Commercially available PEG derivatives include, but are not limited to, amino-PEG, PEG amino acid esters, PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG vinylsulfone, PEG-maleimide, PEG-orthopyridyl-disulfide, heterofunctional PEGs, PEG vinyl derivatives, PEG silanes, and PEG phospholides. The reaction conditions for coupling these PEG derivatives will vary depending on the polypeptide, the desired degree of PEGylation, and the PEG derivative utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc.

6. Pharmaceutical Compositions

*S. aureus* SirA, SirB, SirC, or FhuC antibodies, antisense nucleic acids, siRNAs, and other antagonists, may be administered by various means, depending on their intended use, as is well known in the art. For example, if such *S. aureus* antagonists compositions are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

The pharmaceutical compositions described herein may be used to prevent or treat conditions or diseases resulting from *S. aureus* infections including, but not limited to a furuncle, chronic furunculosis, impetigo, acute osteomyelitis, pneumonia, endocarditis, scalded skin syndrome, toxic shock syndrome, and food poisoning.

7. Exemplary Screening Assays for Inhibitors of the SirABC Mediated Iron Transport System of *S. aureus*

In general, agents or compounds capable of inhibiting pathogenic virulence are identified from large libraries of both natural product or synthetic (or semi-synthetic) extracts or chemical libraries according to methods known in the art. Those skilled in the field of drug discovery and development will understand that the precise source of agents (e.g. test extracts or compounds) is not critical to the screening procedure(s) of the invention. Accordingly, virtually any number of chemical extracts or compounds can be screened using the methods described herein. Examples of such agents, extracts, or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmnaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-pathogenic activity should be employed whenever possible.

When a crude extract is found to have an anti-pathogenic or anti-virulence activity, or a binding activity, further fractionation of the positive lead extract is necessary to isolate chemical constituents responsible for the observed effect. Thus, the goal of the extraction, fractionation, and purification process is the careful characterization and identification of a chemical entity within the crude extract having anti-pathogenic activity. Methods of fractionation and purification of such heterogeneous extracts are known in the art. If desired, compounds shown to be useful agents for the treatment of pathogenicity are chemically modified according to methods known in the art.

Potential inhibitors of SirA, SirB, SirC, staphylobactin, or FhuC may include organic molecules, peptides, peptide mimetics, polypeptides, antibodies, antisense RNA, and siRNAs that bind to a nucleic acid sequence or polypeptide of the invention and thereby inhibit its activity. Potential antagonists also include small molecules that bind to and occupy the binding site of the polypeptide thereby preventing binding to cellular binding molecules, such that normal biological activity is prevented. Other potential antagonists include antisense molecules.

7.1. Interaction Assays

Purified and recombinant SirA, SirB, SirC, staphylobactin and FhuC polypeptides may be used to facilitate the development of assays to screen for agents that modulate the interaction between SirA, SirB, and SirC or between SirA, SirB, SirC, staphylobactin, and/or FhuC. Potential inhibitors of SirA, SirB, SirC, staphylobactin, or FhuC may include small organic molecules, peptides, polypeptides, peptide mimetics, and antibodies that bind to either SirA, SirB, SirC, staphylobactin or FhuC and thereby inhibit its activity.

In an exemplary screening assay, a reaction mixture may be generated to include at least a biologically active portion of either SirA, SirB, SirC, staphylobactin or FhuC polypeptide, agent(s) of interest, and an appropriate interacting molecule. As used herein, the "appropriate interacting molecule" may be SirA, SirB, SirC, staphylobactin or FhuC depending on which polypeptide is used in the screening assay. For example, when SirA is used, an appropriate interacting molecule may be staphylobactin, SirB or SirC. Detection and quantification of interaction of a particular Sir polypeptide with the appropriate interacting molecule provides a means for determining an agent's efficacy at inhibiting interaction between for example, SirA and Sir B. The efficacy of the agent can be assessed by generating dose response curves from data obtained using various concentrations of the test agent. Moreover, a control assay can also be performed to provide a baseline for comparison. In the control assay, interaction of SirA, SirB, SirC, staphylobactin or FhuC polypeptide with the appropriate interacting molecule may be quantitated in the absence of the test agent.

Interaction between SirA, SirB, SirC, staphylobactin or FhuC polypeptide and the appropriate interacting molecule may be detected by a variety of techniques. Inhibition of the formation of complexes can be quantitated using, for example, detectably labeled proteins such as radiolabeled, fluorescently labeled, or enzymatically labeled polypeptides, by immunoassay, or by chromatographic detection.

The measurement of the interaction of a particular Sir or FhuC protein with the appropriate interacting molecule may be observed directly using surface plasmon resonance technology in optical biosensor devices. This method is particularly useful for measuring interactions with larger (>5 kDa) polypeptides and can be adapted to screen for inhibitors of the protein-protein interaction.

Alternatively, it will be desirable to immobilize either SirA, SirB, SirC, staphylobactin or FhuC or the appropriate interacting molecule to facilitate separation of complexes from uncomplexed forms of one or both of the proteins, as well as to accommodate automation of the assay. Binding of SirA to the interacting molecule for example, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/SirA (GST/SirA) fusion proteins can be adsorbed onto glutathione sepharose beads (Sigma Chemical, St. Louis, Mo.) or glutathione derivatized microtitre plates, which are then combined with e.g. an $^{35}$S-labeled interacting molecule, and the test agent, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of interacting molecule found in the bead fraction quantitated from the gel using standard electrophoretic techniques.

Other techniques for immobilizing proteins and other molecules on matrices are also available for use in the subject assay. For instance, either SirA, SirB, SirC, staphylobactin, FhuC or the appropriate interacting molecule can be immobilized utilizing conjugation of biotin and streptavidin. For instance, biotinylated SirA, SirB, SirC, staphylobactin or FhuC can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with either SirA, SirB, SirC, staphylobactin or FhuC, but which do not interfere with the interaction between the polypeptides and the interacting molecule, can be derivatized to the wells of the plate, and SirA, SirB, SirC, staphylobactin or FhuC may be trapped in the wells by antibody conjugation. As above, preparations of an interacting molecule and a test compound may be incubated in the polypeptide-presenting wells of the plate, and the amount of complex trapped in the well can be quantitated in the presence or absence of a test agent. Exemplary methods for detecting such complexes, in addition to those described above for the GST-immobilized complexes, include immunodetection of complexes using antibodies reactive with the interacting molecule or enzyme-linked assays which rely on detecting an enzymatic activity associated with the interacting molecule.

For example, an enzyme can be chemically conjugated or provided as a fusion protein with the interacting molecule. To illustrate, the interacting molecule can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al. (1974) *J. Biol. Chem.* 249:7130).

7.2. Iron-Transport Assays

Alternatively, screening assays may be developed to screen for agents that modulate the iron-transport activity of the Sir polypeptides. Appropriate concentrations of test agents for modulating the iron-transport activity of the Sir proteins can be determined by any method known to one skilled in the art.

In one embodiment, the screening assay may include whole *S. aureus* cells expressing wild type SirA, SirB, SirC or FhuC polypeptides. The ability of a compound to alter the iron transport activity of said polypeptides can be detected by analysis of the cells. For example, antagonists of iron-transport can by detected by scoring for alterations in growth or differentiation (phenotype) of the cell in iron-limited or iron-depleted media. The growth of wild-type *S. aureus* strains in the presence of test agent(s) may be compared with the growth of SirA, SirB or FhuC deficient *S. aureus* strains. Each culture may be treated with a test agent from a library of compounds or natural extracts, and monitored for the effect that the particular agent has on the growth on the wild-type and the Sir-deficient strain or FhuC-deficient strain. Bacterial growth may be monitored using a Klett meter. Compounds that specifically interfere with the SirABC iron siderophore transport system will affect only the growth of the wild-type strain.

Alternatively, *S. aureus* cells may be cultured and treated with test agents and then screened for the presence of iron in the cell using atomic absorption spectroscopy techniques (Cox (1994) *Meth. Enzymol.* 235:315).

Alternatively, inhibition of the iron transport activity may be measured by using radioactively labeled iron. Compounds that interfere with the SirABC iron siderophore transport system will result in a lowered uptake of the radioactively labeled iron. A control assay can also be performed to provide a baseline for comparison. In the control assay, the uptake of radioactively labeled iron in a *S. aureus* cell may be quantitated in the absence of the test compound. Examples of radioactively labeled iron may include $^{59}$Fe or $^{55}$Fe.

7.3. Expression Assays

In a further embodiment, antagonists of the iron transport system may affect the expression of sirA, sirB, sirC or fhuC nucleic acid or protein. In this screen, *S. aureus* cells may be treated with a compound(s) of interest, and then assayed for the effect of the compound(s) on sirA, sirB, sirC or fhuC nucleic acid or protein expression.

For example, total RNA can be isolated from *S. aureus* cells cultured in the presence or absence of test agents, using any suitable technique such as the single-step guanidinium-thiocyanate-phenol-chloroform method described in Chomczynski et al. (1987) *Anal. Biochem.* 162:156-159. The expression of sirA, sirB, sirC or fhuC may then be assayed by any appropriate method such as Northern blot analysis, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al. (1990) *Cell* 63:303-312. Briefly, total RNA is prepared from *S. aureus* cells cultured in the presence of a test agent. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. A *S. aureus* sirA, sirB, sirC or fhuC DNA sequence may be labeled according to any appropriate method (such as the $^{32}$P-multiprimed DNA labeling system (Amersham)) and used as probe. After hybridization overnight, the filter is washed and exposed to x-ray film. Moreover, a control can also be performed to provide a baseline for comparison. In the control, the expression of sirA, sirB, sirC or fhuC in *S. aureus* may be quantitated in the absence of the test agent.

Alternatively, the levels of mRNA encoding SirA, SirB, SirC or FhuC polypeptides may also be assayed, for e.g., using the RT-PCR method described in Makino et al. (1990) *Technique* 2:295-301. Briefly, this method involves adding total RNA isolated from *S. aureus* cells cultured in the presence of a test agent, in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands may be quantified using an imaging analyzer. RT and PCR reaction ingredients and conditions, reagent and gel concentrations, and labeling methods are well known in the art. Variations on the RT-PCR method will be apparent to the skilled artisan. Other PCR methods that can detect the nucleic acid of the present invention can be found in *PCR Primer: A Laboratory Manual* (Dieffenbach et al. eds., Cold Spring Harbor Lab Press, 1995). A control can also be performed to provide a baseline for comparison. In the control, the expression of sirA, sirB or sirC in *S. aureus* may be quantitated in the absence of the test agent.

Alternatively, the expression of SirA, SirB, SirC or FhuC polypeptides may be quantitated following the treatment of *S. aureus* cells with a test agent using antibody-based methods such as immunoassays. Any suitable immunoassay can be used, including, without limitation, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

For example, SirA, SirB, SirC, or FhuC polypeptides can be detected in a sample obtained from *S. aureus* cells treated with a test agent, by means of a two-step sandwich assay. In the first step, a capture reagent (e.g., either a SirA, SirB, SirC, or FhuC antibody) is used to capture the specific polypeptide. The capture reagent can optionally be immobilized on a solid phase. In the second step, a directly or indirectly labeled detection reagent is used to detect the captured marker. In one embodiment, the detection reagent is an antibody. The amount of SirA, SirB, SirC, or FhuC polypeptide present in *S. aureus* cells treated with a test agent can be calculated by reference to the amount present in untreated *S. aureus* cells.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^{3}$H).

Examples of suitable fluorescent labels include a fluorescein label, an isothiocyanate label, a rhodamine label, a phycoerythrin label, a phycocyanin label, an allophycocyanin label, an o-phthaldehyde label, and a fluorescamine label.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of chemiluminescent labels include a luminol label, an isoluminol label, an aromatic acridinium ester label, an imidazole label, an acridinium salt label, an oxalate ester label, a luciferin label, a luciferase label, and an aequorin label.

EXEMPLIFICATION

The invention, having been generally described, may be more readily understood by reference to the following examples, which are included merely for purposes of illustration of certain aspects and embodiments of the present invention, and are not intended to limit the invention in any way.

Example 1

Materials and Methods for Examples 2-5

Media and Growth Conditions

Bacterial strains, plasmids and oligonucleotides used in Examples 2-5 are listed in Table 1. For routine cloning and protein expression, E. coli was grown at 37° C. in Luria-Bertani (LB) broth supplemented with erythromycin (300 μg/ml), ampicillin (100 μg/ml), tetracycline (10 μg/ml), chloramphenicol (30 μg/ml) or kanamycin (30 μg/ml), as required. For general manipulations, S. aureus strains were cultured in tryptic soy broth (TSB) (Difco) containing erythromycin (5 μg/ml), tetracycline (4 μg/ml), kanamycin and neomycin (50 μg/ml) or chloramphenicol (5 μg/ml), as required. For iron-restricted bacterial growth experiments, a Tris minimal succinate (TMS) medium was used, the composition of which has been previously described (Sebulsky et al. (2000) J. Bacteriol. 182:4394-4400). TMS was supplemented with 2'2-dipyridyl, at concentrations as described in the following Examples, to further restrict the concentration of free iron in the media.

Plasmid and Strain Constructions

All DNA manipulations and plasmid constructions were performed using standard protocols. The sirABC operon was PCR-amplified from the chromosome of S. aureus 8325-4 using Pwol polymerase (Roche Diagnostics) and primers Sir upper and Sir lower. The resultant 3.8-kb product was cloned into the SmaI site of pBC SK+ to create pSirABC.

To interrupt the sirA coding region, pSirABC was digested with NsiI, filled with T4 DNA polymerase, and ligated to a kanamycin resistance cassette that had been excised as a StuI/SmaI fragment from pDG782. The sirA::Km region was then cloned into BamHI/KpnI-digested pAUL-A, creating plasmid pMTS12.

The sirB coding region was interrupted by insertion of a tetracycline resistance cassette, derived from digesting pDG1513 with ClaI (end-polished with Klenow enzyme), into the StuI site of sirB. The sirB::tet fragment was cloned into BamHI/KpnI-digested pAUL-A, creating plasmid pSirB::Tet3.

To create strains bearing individual mutations in sirA and sirB, pMTS12 and pSirB::Tet3 were introduced into S. aureus RN4220, followed by transduction via phage 80α, into S. aureus RN6390. Transductants were confirmed by restriction analysis. Allelic replacement was accomplished by growing plasmid-containing bacteria at 30° C. for three hours followed by a shift in growth temperature to 43° C. for a further four hours. Double crossover events were screened for by resistance to kanamycin (for sirA::Km mutation) or tetracycline (for sirB::Tet mutation) with a concomitant loss of erythromycin resistance in both cases. PCR and Southern blot analyses were used to verify the insertion of the antibiotic resistance cassettes into sirA and sirB. The resulting mutant strains were designated H306 (RN6390 sirA::Km) and H474 (RN6390 sirB::Tet). Transduction was used to mobilize the mutations into different genetic backgrounds, such as S. aureus Newman.

For complementation of the sirA::Km mutation, the entire sirABC operon was excised from pSirABC (using KpnI and BamHI) and cloned into pAW8 to create plasmid pSED44. For complementation of the sirB::Tet mutation, the sirB coding region was PCR-amplified from the S. aureus RN6390 chromosome using the primers SirB Comp 5' and SirB Comp 3', followed by digestion with KpnI and SacI for directional cloning into pALC2073, to create plasmid pSED43. Complementing vectors were electroporated into S. aureus RN4220 and transduced into mutant strains using bacteriophage 80a using methodologies previously described (Sebulsky et al. (2000) J. Bacteriol. 182:4394-4400).

RT-PCR

Total RNA for use in RT-PCR reactions was isolated from bacterial cultures in late logarithmic phase using TRIzol® Reagent (Invitrogen). RNA samples were treated with DNaseI for 15 minutes at room temperature prior to the RT-PCR reactions. The SuperScript™ One-Step RT-PCR with Platinum® Taq kit (Invitrogen) kit was used according to manufacturer's instructions. 500 ng of total RNA was reverse transcribed using primers SirB Internal 5' and SirB Internal 3' to amplify a 399-bp fragment internal to the sirB coding region. As an internal control, a 483-bp fragment of gap (encodes glyceraldehyde-3-phosphate dehydrogenase) was amplified using the Gapdh 5' and Gapdh3' oligonucleotide primers.

Bacterial Growth Curves

S. aureus cultures were pre-grown overnight in TMS. Cells were washed before approximately $10^7$ colony forming units of each strain were inoculated into fresh TMS media containing 250 μM 2,2'-dipyridyl (Sigma) with, or without, 50 μM $FeCl_3$. Bacterial growth was monitored using a Klett meter until late stationary phase was reached.

Siderophore Plate Bioassays

Siderophore plate bioassays were performed essentially as previously described (Sebulsky et al. (2000) J. Bacteriol. 182:4394-4400) with the following modifications: TMS-agar was cooled to 45° C. before the addition of 105 cfu/ml of each strain to be tested. 2,2'-dipyridyl was added at a concentration of 550 μM for plates containing S. aureus Newman and Newman containing vehicle controls (e.g. pAW8 and pALC2073) or 400 μM 2,2'-dipyridyl for strains H803 (Newman sirA::Km) and H804 (Newman sirB::Tet) (see FIG. 1) with or without plasmids. Staphylobactin siderophore was isolated from RN6390 as previously described (Dale et al. (2004) Infect. Immun. 72:29-37). Briefly, S. aureus strains were vigorously shaken in TMS for 48 hours at 37° C. Culture supernatants were recovered by centrifugation in 100% methanol to 1/10 of the volume of the original culture supernatant and passed through Whatman No. 1 filter paper to remove particulate material. Rotary evaporation was used to reduce the volume before application to an LH-20 column (Amersham Biosciences). Fractions were collected, and those testing positive with chrome azurol S (CAS) shuttle solution and for biological activity in siderophore plate bioassays were dried, resuspended in water, and examined by high-performance liquid chromatography (HPLC). Analytical reversed-phase HPLC was used for final purification of siderophore. The column utilized was a Waters ODS2 SPherisorb column (4.6 by 150 mm). Trifluoroacetic acid (0.1%) in water represented solvent A whereas 0.1% trifluoroacetic acid in acetonitrile was used as solvent B. The chromatographic method used was as follows: at a flow rate of 0.75 ml/min, 6% B for 3.5 min., followed by a gradient of 6 to 60% B over 20 min. Staphylobactin was detected at 210 nm and had a retention time of approximately 17 min. Staphylobactin was collected, dried, and rechromatographed to check for purity. The purity of Staphylobactin siderophore was confirmed by HPLC analysis. Aerobactin was purchased from EMC microcollections and used at a concentration of 1 µg/ml as a control in all bioassays.

$^{55}$Fe Transport Assays

S. aureus strains were grown to late-logarithmic phase in TMS containing 100 µM 2,2'-dipyridyl with, or without, 50 µM FeCl$_3$. Cells were washed twice with TMS over a 0.45 µm filter (Gelman) and normalized to an OD600=1.2. Twenty minutes prior to 160 the assay, $^{55}$FeCl$_3$ (75 µM) was mixed with approximately 220 µM staphylobactin (calculated from DESFERAL® equivalents) in the presence of 2 µM nitrilotriacetic acid (NTA) and allowed to equilibrate at room temperature. Uptake was initiated by adding 10 µl of the $^{55}$Fe-staphylobactin mixture to 1-ml volumes of cells. At various time points, 200 µl of cells were removed and washed twice with 100 mM LiCl2 over a 0.45 µm membrane. Membranes were dried and counted in CYTOSCINT® fluid using the tritium channel of a Beckman LS 6500 scintillation system. In some experiments, S. aureus were treated with 10 mM potassium cyanide (KCN) at room temperature for 20 minutes prior to addition of $^{55}$Fe mixture. Data presented are pmoles of $^{55}$Fe transported normalized to the total protein content of the cells (+/- standard deviation) as determined by Bradford assays.

Transcriptional lacZ Fusions and β-Galactosidase Assays

The creation of lacZ transcriptional fusions to sbnA, sbnF and sbnI has been previously described (Dale et al. (2004) Infect. Immun. 72:29-37). Internal fragments of individual genes were cloned into the multiple cloning site of pMUTIN4 (Vagner et al., (1998) Microbiology 144:3097-3104), a vector that does not replicate in Gram-positive bacteria. These fusions were transduced into H306 and H474 genetic backgrounds and the presence of mutations and gene fusions were confirmed by PCR. The construction of a sbnH::lacZ transcriptional fusion has also been previously described (Dale et al. (2004) Infect. Immun. 72:29-37). This fusion was transduced into Newman, H803 and H804 genetic backgrounds and the presence of the gene fusion was confirmed by PCR.

For quantitation of β-galactosidase expression from S. aureus, cells were grown to an optical density at 600 nm of 0.8 in TMS supplemented with 100 µM 2,2'-dipyridyl and assayed as previously described (Dale et al. (2004) Infect. Immun. 72:29-37). Briefly, cultures were lysed in a solution containing 10 mM potassium phosphate buffer (pH 7.5), 15 mM EDTA, 1% Triton X-100, and 10 µg of lysostaphin at 37 C. After centrifugation of cell debris, 5 µl of supernatant was assayed for β-galactosidase activity using the Galacto-Light Plus Chemiluminescent reporter gene kit (Tropix) in a Berthold luminometer. The background was set at 50 relative light units/s and the data presented are mean relative light units per second for three independent samples±standard error.

Purification of SirA and Generation of Anti-SirA Antisera

We expressed SirA, minus the signal peptide, in E. coli ER2566 by cloning sirA, amplified from the genome of S. aureus using primers pSirA (BamHI) and pSirA (EcoRI), into pGEX-2T-TEV digested with EcoRI and BamHI. This construct, named pSirA, was grown to mid-log phase before being induced with 0.5 mM IPTG for four hours. Cells were lysed using a French Press and the lysate was centrifuged at 40,000 rpm to pellet cell debris. The supernatant was applied to a GSTrap (Amersham Biosciences) column equilibrated with PBS and the GST-SirA fusion protein was eluted with 10 mM reduced glutathione in 50 mM Tris-Cl, pH 8.0. SirA was cleaved from GST by incubation with tobacco etch virus protease for 3 hours at room temperature and dialyzed overnight at 4° C. against 50 mM Tris-Cl, pH 8.0. SirA was further purified using a Mono S column (Amersham Biosciences) equilibrated with sodium phosphate buffer, pH 7.0 and the protein was eluted in sodium phosphate buffer containing 1M NaCl. The purity of SirA was confirmed by SDS-PAGE.

Antibodies recognizing SirA were generated in New Zealand white rabbits (Charles River) inoculated subcutaneously with 500 µg of SirA emulsified in 100 µl Freund's complete adjuvant. On days 14 and 28, rabbits received booster injections of 100 µg of SirA emulsified in Freund's incomplete adjuvant. Rabbits were sacrificed 10 days following the second boost. Antisera were adsorbed against H306 cell lysates and used at a 1:2000 dilution for Western blots.

Example 2

Expression of SirA is Iron-Regulated Via Fur

Figure 2:
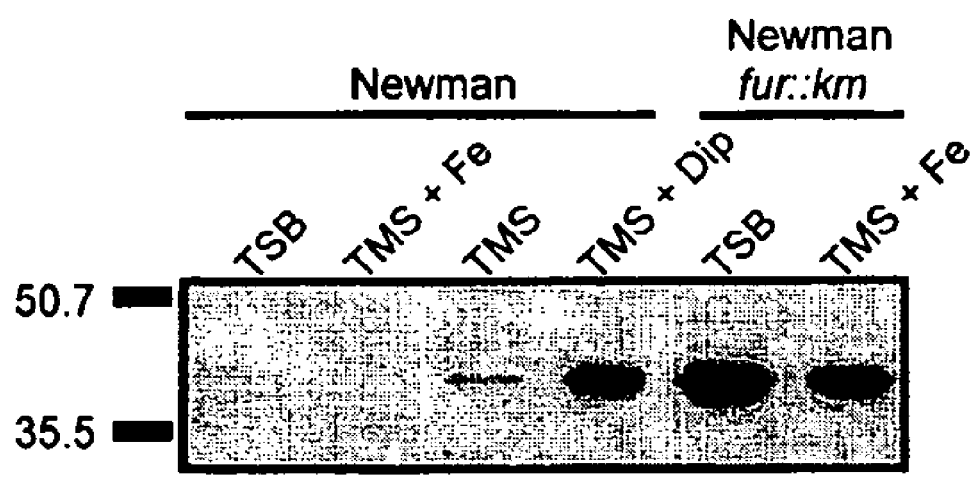
FIG. 2 is an immunoblot showing iron- and Fur-regulated expression of SirA in *S. aureus* Newman and its fur::Km derivative. Cells were grown in either iron rich (TSB, TMS+Fe) or iron-restricted (TMS, TMS+Dip) media, normalized by optical density and lysed. SirA was detected in cell lysates with rabbit polyclonal antisera directed at SirA.

Although SirA expression was undetectable in S. aureus Newman cultured in iron-replete media (either TSB or TMS containing 50 µM FeCl$_3$), its expression was readily detectable during upon growth under conditions of iron restriction (FIG. 2). Expression levels increased as the level of iron restriction increased (i.e. when 2,2'-dipyridyl was added to TMS) (FIG. 2). These findings are in agreement with previous studies which used S. aureus 8325-4 (Heinrichs et al. (1999) J. Bacteriol. 181:1436-1443). We have further demonstrated that SirA expression was controlled by the activity of the Fur protein in S. aureus, since SirA expression was no longer iron-regulated in a Fur-deficient background (FIG. 2). This finding is in agreement with the predicted presence of a consensus Fur box upstream of sirA (Dale et al. (2004) Infect. Immun. 72:29-37; Heinrichs et al. (1999) J. Bacteriol. 181: 1436-1443).

Example 3

In the Absence of sirB and sirC, the sirA Gene Product is Toxic to E. coli

Many unsuccessful attempts, using different vectors and promoter systems (data not shown), were made to clone the sirA coding region for complementation of H803. These unsuccessful results indicated that 'leaky' expression of even small quantities of this lipoprotein was lethal to E. coli. The problems encountered with the cloning of sirA, appear not to be due to the soluble or amphiphilic regions of the protein since, for the generation of anti-SirA antisera, sirA lacking the signal peptide was successfully cloned into an E. coli expression vector and large quantities of soluble SirA was produced. These results lend support to the idea that the problems encountered with cloning sirA may be due to improper processing of the lipoprotein in E. coli.

Interestingly, however, the apparent toxic effect of the SirA lipoprotein on E. coli occurred only when attempts were made to clone the sirA gene on its own and not when sirB and sirC were included in the cloned DNA. Indeed, the sirABC genes were successfully cloned as a unit on plasmid pSirABC (Table 1) and this plasmid expressed large quantities of SirA in E. coli. This result suggests that the transmembrane components of the transporter, components that would presumably interact with SirA at the membrane, may help stabilize the lipoprotein in the membrane.

Example 4

SirA and SirB are Involved in Iron Acquisition

The Sir polypeptides share similarity with the membrane components of ABC transporters (SirB and SirC) and ligand binding proteins (SirA) and, more specifically, with transporters involved in the acquisition of iron. To address the potential role of sirABC in iron acquisition, we used kanamycin and tetracycline resistance cassettes to insertionally-inactivate the coding regions of sirA and sirB, respectively, in S. aureus RN6390. Mutations from each of these strains, designated H306 (S. aureus RN6390 sirA::Km) and H474 (S. aureus RN6390 sirB::Tet), were transduced into S. aureus Newman to create strains H803 (sirA::Km) and H804 (sirB::Tet). While SirA was undetectable in H803 (sirA::Km), the H804 (sirB::Tet) mutant expressed wildtype levels of SirA. A faintly reactive band that migrated faster than SirA is visible in cell extracts of H803. This band is likely due to cross-reactivity with another protein due to the polyclonal antisera that was used. This protein band is likely masked by the high-level expression of the SirA protein in the other samples tested (i.e., SirA expression was detected in E. coli (pSED44) and H686 (sbnE::Km)), since it is visible when S. aureus Newman was grown in iron-replete conditions (FIG. 2).

In previous studies, sensitivity to streptonigrin has been used as a method to demonstrate the loss or perturbation of iron import in S. aureus (Sebulsky et al. (2000) J. Bacteriol. 182:4394-4400). Streptonigrin is toxic to cells in the presence of intracellular iron and, therefore, cells importing iron are generally more sensitive to the toxic affects of this drug versus mutants debilitated in iron import (Yeowell et al. (1982) Antimicrob. Agents Chemother. 22:961-968). The minimum inhibitory concentration (MIC) of streptonigrin was approximately 4-fold lower for S. aureus Newman grown in TMS than for either S. aureus H803 or H804 grown in the same media (see Table 2). Different susceptibilities to streptonigrin were overcome by inclusion of DESFERAL1®, an iron-chelating agent, into the growth media, indicating that this siderophore was used equally well by parent and mutants. These data indicated that SirA and SirB were likely involved in the transport of iron into the cell. As further evidence in this regard, the MIC of 2,2'-dipyridyl (a non-metabolizable iron chelator) for S. aureus Newman was demonstrated to be 4-fold higher than for either H803 or H804 (Table 2).

Figure 3:
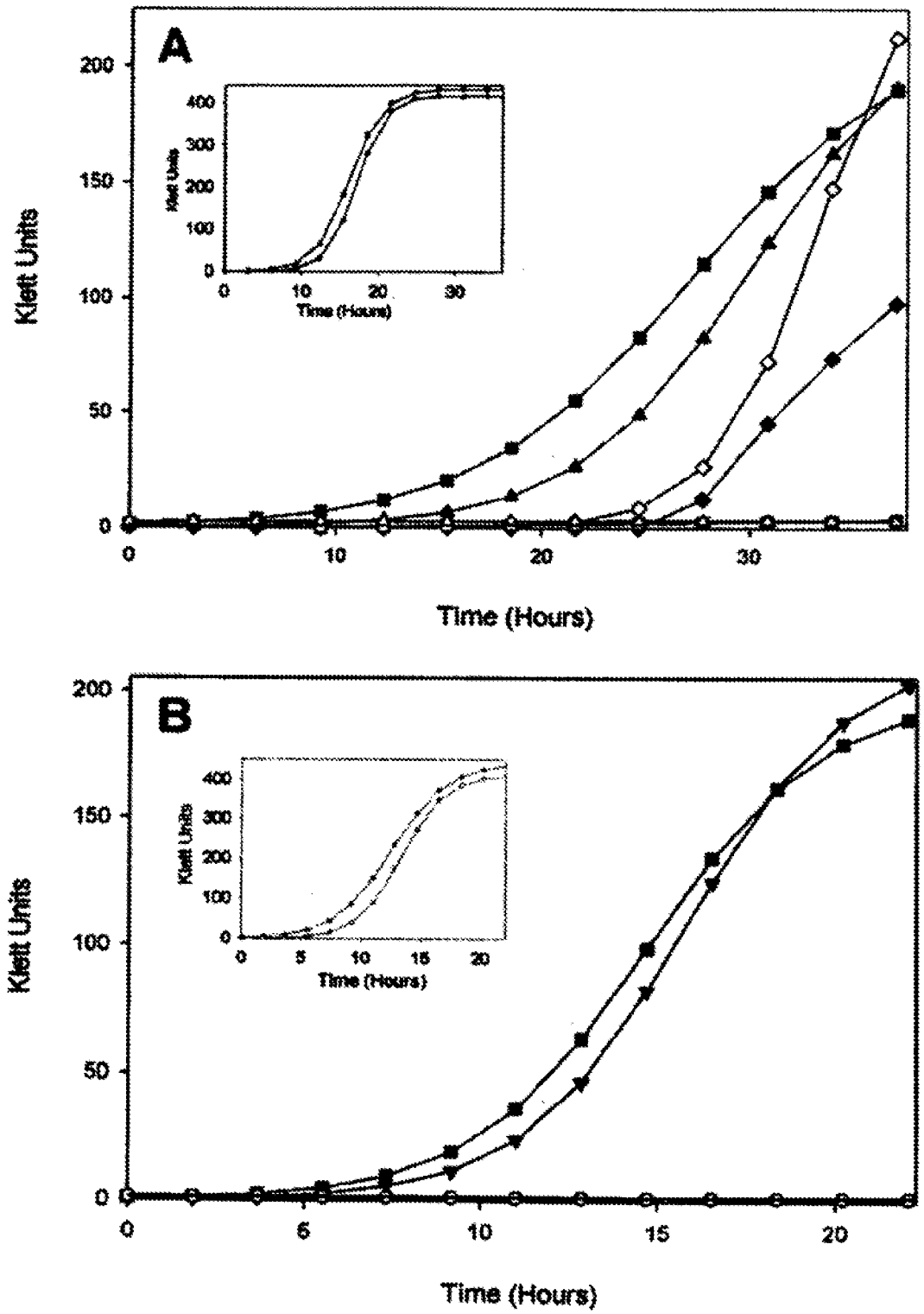
FIG. 3 are graphs comparing the growth of *S. aureus* Newman versus a sirA::Km mutant derivative (A) or a sirB::Tet mutant derivative (B) in TMS broth containing 250 µM 2,2'-dipyridyl and 50 µM FeCl$_3$ (inset) or 250 µM 2,2'-dipyridyl. ■, Newman; □, H803 (sirA::Km); ▲, Newman carrying pAW8 vector; ∆, H803 carrying pAW8; ♦, H803 carrying pSED44 grown without IPTG; 0, H803 carrying pSED44 grown with 1 mM IPTG; o, H804 (sirB::Tet); ▼, H804 carrying pSED43. Data are representative of three experiments.

Growth of wild-type Newman and derivatives was followed over a 24-36 hour time period in order to identify deficiencies in growth rate that would correlate with the loss of either sirA or sirB function. In iron-replete growth media, the growth of H803 (Newman sirA::Km) was unaltered in comparison to Newman (FIG. 3A, inset). H803, however, showed a drastic growth deficiency compared to Newman in iron-restricted growth media (FIG. 3A). Introduction of plasmid pSED44 (contains the sirABC operon expressed from Plac; FIG. 1) into H803 corrected the growth deficiency of this strain in iron-restricted growth media. The Plac promoter in the pAW8 vector expresses large quantities of SirA from the pSED44 construct in E. coli but extremely little SirA in S. aureus, even in the presence of 1 mM IPTG (data not shown), indicating that Plac is functional but extremely inefficient in S. aureus. However, even this small amount of SirA was capable of complementing the mutation in H803. The addition of 1 mM IPTG to the iron-deficient growth media did enhance the complementation (FIG. 3). Introduction of vehicle alone into either Newman or H803 did not affect their growth rate (FIG. 3).

Since we were unable to complement the sirA::Km mutation with the sirA coding region alone (see below), we had to rule out the possibility of polarity of the sirA::Km mutation on expression of downstream sir genes. RT-PCR experiments demonstrated that the sirA::Km mutation had no effect on expression of sirB (data not shown), while also confirming that expression of sirB transcript was regulated by iron concentrations in the growth medium. Further, sirB was not detected in H804, the strain containing the sirB::Tet mutation, grown under iron starvation conditions since the Tet cassette disrupts the region amplified in the PCR. In these experiments, total RNA (500 ng) was reverse transcribed and the cDNA to sirB and gap were amplified as described in Example 1.

Similar to H803, the growth of H804 (Newman sirB::Tet) in iron-replete media was unaltered in comparison to wild-type Newman (FIG. 3B, inset). However, as with H803, the growth of H804 was severely impaired in iron-deficient growth media compared to S. aureus Newman (FIG. 3B). This growth deficiency of H804 was alleviated with the introduction of pSED43 into the strain (FIG. 3B); pSED43 expresses sirB from a xyl/tet promoter (FIG. 1). The xyl/tet promoter was found to be quite leaky in S. aureus (data not shown) and therefore it was unnecessary to incorporate inducer (anhydrotetracycline) into the growth media in these experiments to see full restoration of wildtype phenotype.

Example 5

Mutation of SirA and SirB Results in S. aureus Defective in Staphylobactin Transport but not Staphylobactin Biosynthesis Staphylobactin was isolated from S. aureus RN6390 using previously described techniques (Dale et al. (2004) Infect. Immun. 72:29-37). Purified staphylobactin was used to assess growth promotion in siderophore plate bioassays. While staphylobactin readily promoted the growth of S. aureus Newman, RN6390 and H287 (fhuG::Tn917) in siderophore plate bioassays, no staphylobactin-mediated growth promotion was observed for H306 (RN6390 sirA::Km), H474 (RN6390 sirB::Tet), H803 (Newman sirA::Km) or H804 (Newman sirB::Tet), indicating that both SirA and SirB are essential for staphylobactin-mediated iron transport. To confirm these results, purified staphylobactin was incubated with $^{55}FeCl_3$ and transport assays were performed with S. aureus Newman and H803. While significant transport of $^{55}$Fe-staphylobactin was observed in S. aureus Newman, virtually no transport occurred in Newman pre-grown in TMS containing $FeCl_3$, Newman treated with 10 mM KCN or in H803 (data not shown). Together, these results confirm that staphylobactin transport is an iron-regulated process that requires the function of at least SirA and SirB, and suggest that this transport is an ATP consuming reaction. Growth promotion by aerobactin, DESFERAL® and ferric-citrate was unaffected in sirA and sirB mutants and growth in the presence of staphylobactin was restored in the complemented sirA::Km and sirB::Tet mutants (data not shown).

At least in one instance in S. aureus, more than one gene encoding the lipoprotein (or binding protein) component of a transport system is found in the genome. Indeed, the iron-hydroxamate uptake system in many strains of S. aureus is comprised of single copies of genes encoding the ABC-transporter components but two genes that encode a binding protein component (e.g., fhuD1 and fhuD2) (Sebulsky and Heinrichs (2001) *J. Bacteriol.* 183:4394-4400; Sebulsky et al. (2003) *J. Biol. Chem.* 278:49890-900). In strains containing both fhuD1 and fhuD2, mutation of one of the genes leads to a phenotype that is either wildtype or very close to wildtype for iron-hydroxamate uptake (Sebulsky and Heinrichs (2001) *J. Bacteria* 183:4394-4400). Given that both the sirA::Km and sirB::Tet mutations lead to equivalent phenotypes, we conclude that there is only one gene encoding the binding protein (i.e., SirA) component and one copy of genes (i.e., sirB and sirC) encoding the membrane permease for this transport system.

Given that the functions of proteins expressed from the sbn operon and the sir operon are associated (i.e., biosynthesis and import of staphylobactin), we wished to determine whether there were any effects on their expression as a function of mutations in the operons. Mutation of sbnE results in the loss of staphylobactin synthesis (Dale et al. (2004) *Infect. Immun.* 72:29-37), however, we showed that loss of sbnE function and, therefore, biosynthesis of staphylobactin had no major effect on the expression of SirA (data not shown). In corollary experiments, we investigated whether loss of sirA or sirB resulted in loss of, or decreased, staphylobactin production. We observed that H803, grown in moderately iron-restricted media, produced significant amounts of staphylobactin both by analytical HPLC and ESI-mass spectrometry (data not shown). To investigate this phenomenon further, we transduced a transcriptional lacZ-sbnH fusion into Newman, H803 and H804. We observed a significant increase in transcription of the sbnH gene in the H803 and H804 genetic backgrounds compared to wildtype Newman (Table 3). No transcription of β-galactosidase activity was observed when strains containing the fusion were grown in iron-replete conditions (data not shown). These results suggest that staphylobactin biosynthesis may be enhanced in strains deficient in the ability to transport this siderophore, presumably in response to an elevated iron starvation status.

Example 6

Material and Methods for Examples 7-12

Bacterial strains, plasmids, and growth conditions

Bacterial strains and plasmids used in Examples 7-12 are described in Table 4. *E. coli* was grown in Luria-Bertani broth (Difco). For experiments not directly involved in the analysis of iron uptake, *S. aureus* was grown in tryptic soy broth (Difco). Tris-minimal succinate (TMS) was prepared as described (Sebulsky et al. (2004) *J. Biol. Chem.* 279:53152-9) and used as an iron-limited minimal media. To further restrict the level of free iron in TMS, the iron chelating compounds 2,2'-dipyridyl and ethylene diamine-di(o-hydroxyphenol acetic acid) (EDDHA) were added as indicated in the text. Where necessary, ampicillin (100 µg/ml) or kanamycin (30 µg/ml) was incorporated into the media for the growth of *E. coli* strains. For *S. aureus*, chloramphenicol (5 µg/ml), kanamycin (50 µg/ml), neomycin (50 µg/ml), erythromycin (3 µg/ml), and lincomycin (20 µg/ml) were incorporated into growth media as required. Solid media were obtained by the addition of 1.5% (w/v) Bacto agar (Difco). All bacterial growth was conducted at 37° C. unless otherwise stated. Iron-free water for preparation of growth media and solutions was obtained by passage through a Milli-Q water filtration system (Millipore Corp.).

Recombinant DNA Methodology

Standard DNA manipulations were performed essentially as described by Sambrook et al. (Sambrook et al. (1989) *Molecular cloning: A Laboratory Manual,* 2nd ed. Cold Spring Harbor Laboratory Press, Cold Spring Harbor). Restriction endonucleases and DNA-modifying enzymes were purchased from Roche Diagnostics (Laval, Quebec, Canada), New England Biolabs (Mississauga, Ontario, Canada), Life Technologies Inc. (Burlington, Ontario, Canada) and MBI Fermentas (Flamborough, Ontario, Canada). Plasmid DNA was purified using QIAprep plasmid spin columns (QIAgen Inc., Santa Clarita, Calif.) as described by the manufacturer. For plasmid isolation from *S. aureus*, lysostaphin (50 µg/mL) was added to buffer P1. Chromosomal DNA from *S. aureus* was isolated using the InstaGene™ Matrix (Bio-Rad) as described by the manufacturer. Polymerase chain reactions were performed using either PwoI or Taq DNA polymerase (Roche Diagnostics).

Construction of a ΔfhuCBG::ermB Mutant

To create a deletion of the fhuCBG operon in the chromosome of RN6390, two regions of DNA flanking the operon were amplified from the RN6390 chromosome by PCR. Primers fhuC upstream sense (5'-TTGAATTCAATACCTC-GATGTAAGCACG-3') (SEQ ID NO: 17) and fhuC upstream antisense (5'-TTGGATCCACGATTCATAATTTCCCTAC-3') (SEQ ID NO: 18) were used to amplify a 709-bp fragment upstream of and including the first 9-bp of the fhuC open reading frame, and primers fhuG downstream sense (5'-TTG-GATCCAACGAAAAATGTATAGTGTC-3') (SEQ ID NO: 19) and fhuG downstream antisense (5'-TTTCTAGACG-GCAAGCTTATGAACAAAC-3') (SEQ ID NO: 20) were used to amplify a 718-bp fragment downstream of fhuG including the final 13-bp of the fhuG open reading frame.

The fhuC upstream fragment was digested with EcoRI and BamHI (recognition sites underlined in primer sequences) and the fhuG downstream fragment was digested with BamHI and XbaI (recognition sites underlined in primer sequences) and these two fragments were cloned together into pUC19 digested with EcoRI and XbaI. The resulting construct was digested with BamHI and a 1.6-kb BamHI fragment from pDG646, carrying the ermB gene, was inserted. The resulting plasmid construct was digested with EcoRI and XbaI and a 3027-bp fragment harbouring ermB between the fhuC upstream and fhuG downstream fragments was ligated into pAUL-A Km digested with EcoRI and XbaI to create the plasmid pΔfhuCBG.

Plasmid pΔfhuCBG was introduced into *S. aureus* RN4220 by electroporation and colonies resistant to kanamycin and neomycin were selected after growth at 30° C. Kanamycin resistant clones were subjected to a temperature shift to 42° C. to select for plasmid integration in the chromosome. Bacteria that were resistant to erythromycin and lincomycin but sensitive to kanamycin and neomycin were selected.

The ΔfhuCBG::ermB mutation was confirmed by PCR and the mutation was subsequently transduced to the RN6390 and Newman backgrounds to create strains H1071 and H 1074, respectively.

Construction of Complementing Plasmids

In order to complement the ΔfhuCBG::ermB mutation, pMTS20 (Sebulsky et al. (2000) *J. Bacteriol.* 182:4394-4400) was digested with BamHI and the resulting 3.7-kb fragment harbouring the fhuCBG operon with approximately 400-bp of upstream DNA (encompassing the Fur box and promoter sequences) was ligated into the BamHI site of pLI50 to create pFhuCBG. To create pFhuC, primers fhuCBG2 (5'-TTTGGATCCACAAGTTTCAAAAG-CAAAGC-3') (SEQ ID NO: 21) and fhuC antisense (5'-TTG-GATCCATTTGTCATGTTAATTGTCC-3') (SEQ ID NO: 22) were used to amplify a 1.2-kb region containing the fhuC coding region plus the same 400-bp upstream region as in pFhuCBG, and the resulting PCR product cloned into the BamHI site of pLI50.

Siderophores

Ferrichrome was purchased from Sigma (Mississauga, Ontario, Canada), desferrioxamine B, used as DESFERAL® (Novartis), was obtained from the London Health Sciences Centre (London, Ontario), and enterobactin was purchased from EMC Microcollections GmbH (Tübingen, Germany). Staphylobactin was prepared as previously described (Dale et al. (2004) *J. Bacteriol.* 186:8356-62).

Bioassays

Siderophore plate bioassays were performed essentially as described (Sebulsky et al. (2000) *J. Bacteriol.* 182:4394-4400). Briefly, $10^4$ cells/mL were added to molten TMS agar containing 25 µM EDDHA as an iron chelating agent. Ten microliters of iron sources to be tested (DESFERAL® (50 µM), ferrichrome (50 µM), enterobactin (500 µM), staphylobactin (50 µM DESFERAL® equivalents), hemin (250 µg/mL), hemoglobin (2 mg/mL), $FeCl_3$ (50 mM), or ferric citrate (5 mM)) were added to sterile 6 mm-diameter paper disks and placed on the surface of the plates. Growth promotion, as measured by the diameter of the growth halo around each disk, was determined after 48 h incubation, except for heme and hemoglobin, which were measured after 72 hours.

Determination of Minimal Inhibitory Concentration of 2,2'-dipyridyl for *S. aureus* Strains Strains to be tested were pre-grown in TMS and cells were washed in fresh TMS prior to assay. 2,2'-dipyridyl was added to TMS and serially diluted to give a range from 1 mM to 32 µM. Following serial dilution, $5 \times 10^4$ CFUs were added to each 5-mL culture and growth was recorded after 24 hours incubation.

Bacterial Growth Curves

Strains were pre-grown overnight in TMS. Cells were washed with TMS and $5 \times 10^6$ CFUs were added to 50 mL of fresh TMS or TMS supplemented with 50 µM 2,2'-dipyridyl in acid-washed flasks. Where necessary, 50 µM $FeCl_3$ was added to the media to create iron-replete conditions. Bacterial growth was monitored by measuring the optical density of the culture at 600 nm ($OD_{600}$) until stationary phase was reached.

$^{55}$Fe Transport Assays

Siderophore uptake was measured as previously described (Dale et al. (2004) *J. Bacteriol.* 186:8356-62) with the following modifications: all strains were grown overnight in TMS containing 50 µM 2,2'-dipyridyl and appropriate antibiotics, with the exception of RN6390 ΔfhuCBG::ermB (H1071), which was grown in TMS alone. Cells were washed three times in TMS and normalized to an optical density at 600 nm of 2.0. Siderophores (DESFERAL® and staphylobactin, ~200 µM each) were mixed with $^{55}FeCl_3$ (75 µM) in the presence of 4 µM nitrilotriacetic acid and the mixtures were equilibrated at room temperature for 30 minutes. Iron uptake was initiated by adding 10 µl of each $^{55}$Fe-siderophore mixture to 1 mL of cells. At various time points, 200 µL of cells were removed and washed twice with 100 mM LiCl over a 0.45 µM pore-size membrane (Pall Gelman). Dried membranes were counted in CytoScint® fluid using the tritium channel of a Beckman LS-6500 scintillation system. In some experiments, bacteria were exposed to 10 mM potassium cyanide for 15 minutes at room temperature prior to initiating uptake with the $^{55}$Fe-siderophore mixtures. The data presented are the picomoles of $^{55}$Fe transported normalized to the optical density of the cultures.

Mouse Kidney Abscess Model

Female Swiss-Webster mice (25 g each) were purchased from Charles River Laboratories Canada Inc., and housed in microisolator cages. *S. aureus* Newman and Newman ΔfhuCBG::ermB (H1074), were grown overnight in TSB, washed three times with sterile saline and suspensions of $1 \times 10^8$ cfu/mL were made in sterile saline. One hundred microliters of the cell suspensions were administered intravenously via the tail vein. The number of viable bacteria injected was confirmed by plating serial dilutions of the inocula on TSB-agar. Throughout the course of the experiment, the mice were subjectively scored on their grooming habits and locomotory function. A score of 1 indicated normal function, whereas higher scores indicated altered function (see Results below). On day 7, the mice were euthanized and the kidneys were aseptically removed and homogenized in sterile PBS+0.1% Triton X-100 using a PowerGen 700 Homogenizer. Homogenates were serially diluted and plated on TSB-agar to enumerate recovered bacteria. Data presented are the log CFU recovered per mouse. The significance of the percentage of kidneys exhibiting visible abscesses in each group was determined using the Z and Fisher's Exact tests.

Computer Analyses

DNA sequence analysis and PCR oligonucleotide primer design were performed using the Vector NTI Suite 7 software package (Informax, Inc.). Microsoft Excel and SigmaPlot (SPSS Inc.) were used for data analysis and graphing applications.

Example 7

Construction of *S. aureus* ΔfhuCBG::ermB Mutant

Figure 4:
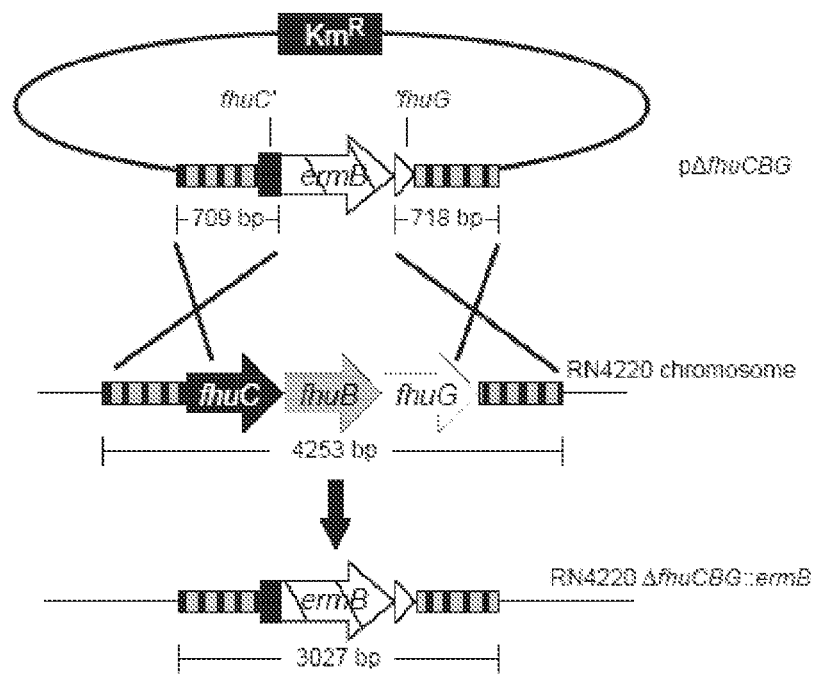
FIG. 4 is a schematic diagram showing the allelic replacement of fhuCBG in the genome of *S. aureus* RN6390. The flanking regions of fhuCBG, fhuC' and 'fhuG, were amplified from the RN6390 chromosome, ligated to either side of ermB, and cloned into the temperature-sensitive shuttle vector pAUL-A-Km. This construct allowed for the replacement of fhuCBG by ermB in the RN4220 genome by homologous recombination. Phage transduction was used to mobilize the mutation into the RN6390 and Newman backgrounds to yield strains H1071 and H1074, respectively. Sizes of relevant DNA fragments are indicated.

The iron-regulated fhuCBG operon was previously identified by our laboratory (Sebulsky et al. (2000) *J. Bacteriol.* 182:4394-4400) and by Xiong et al. (Xiong et al. (2000) *Microbiology* 146:659-668), and was shown to be necessary for transport of iron(III)-hydroxamates in *S. aureus* since mutations in either fhuB or fhuG eliminated transport (Cabrera et al. (2001) *Appl. Environ. Microbiol.* 67:1001-3; Sebulsky et al. (2000) *J. Bacteriol.* 182:4394-4400). The operon is present in all sequenced *S. aureus* genomes (Sebulsky et al. (2004) *J. Biol. Chem.* 279:53152-9). As part of our studies to elucidate the mechanism of iron(III)-siderophore transport in *S. aureus* using the fhu system as a model, we constructed a *S. aureus* strain, in the RN4220 genetic background, H1068, that contained a fhuCBG operon deletion (see FIG. 4). The mutation was mobilized by phage transduction to the RN6390 and Newman genetic backgrounds, creating strains H1071 and H1074, respectively.

Example 8

A ΔfhuCBG Mutant is Unable to Utilize iron(III)-hydroxamates

In agreement with previous results indicating that loss of either fhuG or fhuB result in a complete inability to utilize any iron(III)-hydroxamate complexes for iron-restricted growth, plate bioassays showed that H1071 was unable to utilize DESFERAL®, ferrichrome, coprogen, and aerobactin. H1071 was able to utilize all aforementioned hydroxamate siderophores for iron acquisition in siderophore plate bioassays when the strain was provided with the fhuCBG operon in trans, on plasmid pFhuCBG (data not shown).

Example 9

Mutation of fhuC, but not Other fhu Genes, in *S. aureus*, Yields an Iron-Restricted Growth Defect Previously unpublished results from our laboratory indicated that Jim mutations in *S. aureus*, for example RN6390 fhuG::Tn917 (H287) and RN6390 fhuD1::Km fhuD2::Tet (H431), did not have an obvious growth defect in iron-deficient media, suggesting that hydroxamate siderophores are not produced by *S. aureus* in response to iron starvation; in agreement, *S. aureus* culture supernatants test negative in the Czaky test (Payne (1994) Detection, isolation, and characterization of siderophores, p. 329-344. In V. L. Clark and P. M. Bavoil (ed.), *Methods in Enzymology*, vol. 235. Academic Press, Inc., San Diego, Calif.) for hydroxamates (data not shown). Surprisingly, however, we observed that the growth of H1071 was significantly retarded compared to wildtype RN6390, H287 (RN6390 fhuG) and H431 (RN6390 fhuD1 fhuD2) in iron-deficient TMS media (data not shown) and even more so in TMS containing 50 µM 2,2'-dipyridyl, a non-metabolizable iron chelator (data not shown). Addition of 50 µM ferric chloride to TMS restored growth of H1071 to wild-type levels demonstrating that the impaired growth was due solely to the level of iron available to the bacteria (data not shown). The iron-restricted growth defect demonstrated by H1071 could be complemented by introduction of a plasmid carrying the operon (pFhuCBG). However, more surprising was the observation that fhuC alone in trans, present on plasmid pFhuC, complemented the iron-restricted growth deficiency of strain H1071, indicating that the growth defect of H1071 was as a result of the inability to express fhuC. $^{55}$Fe-DESFERAL® uptake assays were performed and showed that H1071 was incapable of transporting $^{55}$Fe-DESFERAL® (data not shown), corroborating bioassay results (see above). Of note, however, was the observation that although pFhuC could complement the growth deficiency of H1071, it could not restore the ability of H1071 to transport $^{55}$Fe-DESFERAL® (data not shown), corroborating previous results that showed that FhuB and FhuG were also required for iron(III)-hydroxamate uptake (Cabrera et al. (2001) *Appl. Environ. Microbiol.* 67:1001-3; Sebulsky et al. (2000) *J. Bacteriol.* 182:4394-4400), but also indicating that an additional iron(III)-siderophore transport system, one that is required for iron-restricted growth in *S. aureus*, was interrupted in H1071.

As expected, and in agreement with previous results showing that neither a fhuB (Cabrera et al. (2001) *Appl. Environ. Microbiol.* 67:1001-3) nor fhuG (Sebulsky et al. (2000) *J. Bacteriol.* 182:4394-4400) knockout strain could utilize hydroxamate-type siderophores, the ΔfhuCBG::ermB mutant was unable to transport iron(III)-hydroxamates as demonstrated by both siderophore plate bioassay and in transport assays, and this defect was fully complemented by the introduction of fhuCBG in trans. That the ΔfhuCBG::ermB mutant exhibited an iron-dependent growth defect in TMS media alone was surprising, given that strains lacking either fhuG or both of fhuD1 and fhuD2 do not exhibit any measurable growth defect under similar conditions in comparison to wildtype RN6390. Given our observation that introduction of fhuC into H1071 restored the growth defect but did not restore the ability to utilize iron(III)-hydroxamates, suggested that an endogenous iron uptake system was impaired in the mutant.

Example 10

FhuC is Required for iron(III)-staphylobactin Transport in *S. aureus*

Figure 5:
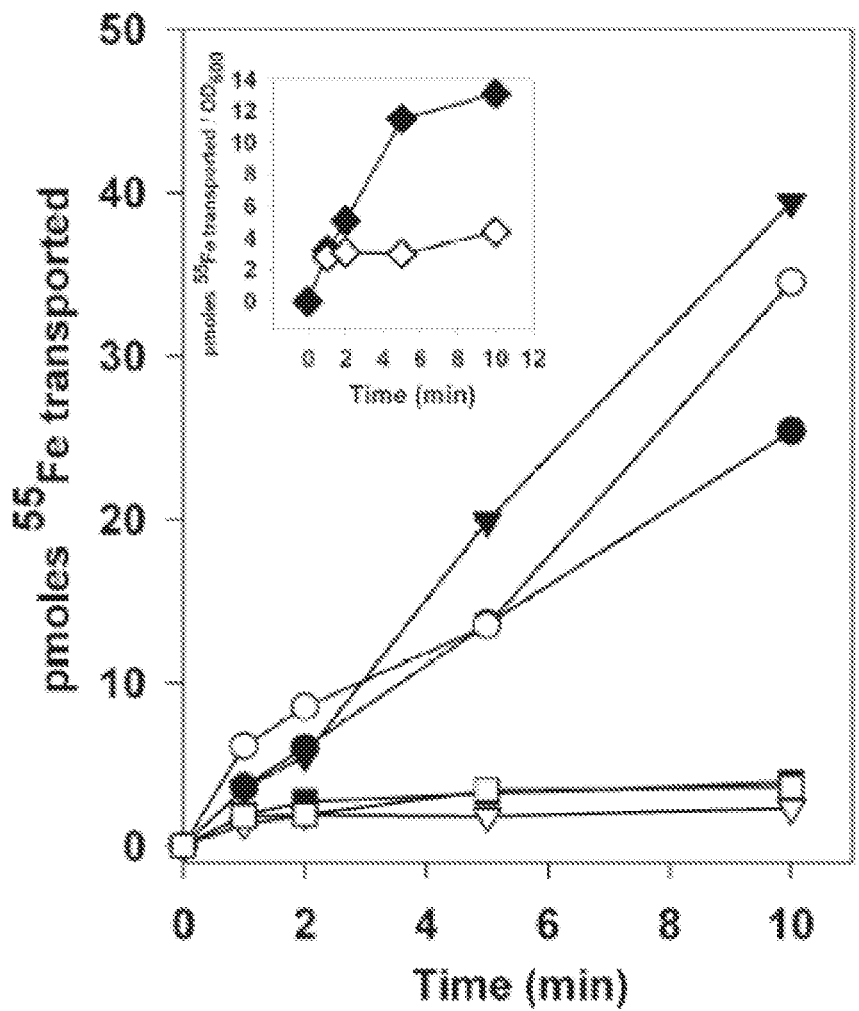
FIG. 5 is a graph showing $^{55}$Fe-staphylobactin-mediated iron transport by *S. aureus* RN6390 and H1071 derivatives grown in TMS containing 50 µM 2,2'dipyridyl. ●, RN6390; ○, H1071+pFhuC; ▼, H1071+pFhuCBG. RN6390 (∇), H1071+pFhuC (■) and H1071+pFhuCBG (□) were all treated with 20 mM KCN 15 minutes prior to assay. Inset: Strains (♦, RN6390; ◊, H1071) grown prior to assay in TMS without 2,2'-dipyridyl, which was performed because strain H1071 without complementing plasmids does not grow well in the presence of 2,2'-dipyridyl, however, RN6390 is not as iron-starved in this experiment as when it is grown in the presence of 50 µM 2,2'-dipyridyl. Each point represents the pmoles of $^{55}$Fe transported by $2\times10^8$ cells from the assay mixture.

FhuC (Sebulsky et al. (2000) *J. Bacteriol.* 182:4394-4400) shares significant similarity with ATPases and has all the hallmarks (signature sequences) of an ATP-binding protein (Holland and Blight (1999) *J. Mol. Biol.* 293:381-99). Analysis of the *S. aureus* genome identified several operons whose predicted products share significant similarity with iron(III)-siderophore ABC-type transporters and iron(III)-siderophore binding proteins. At least three of these putative operons, SirABC, IsdEF and SA1977-SA1979 (using N315 genome designations), however, lack a gene whose predicted product shares similarity with ATPase components of ABC transporters. Thus, it is possible that FhuC interacts with one or more of these other *S. aureus* ABC transporters to transport an iron-complex that is required for growth under iron limitation. Our previous studies characterized the phenotype of SirA and SirB mutants, both of which demonstrate a growth-impaired phenotype under conditions of iron limitation and which we showed were required for the transport of iron(III)-staphylobactin (Dale et al. (2004) *J. Bacteriol.* 186:8356-62). Thus, we tested H1071 for its ability to utilize staphylobactin in $^{55}$Fe-staphylobactin transport assays. These results showed that H1071 could not utilize staphylobactin (FIG. 5, inset). Moreover, complementation of this mutant with pFhuCBG and, most notably, pFhuC alone resulted in significant staphylobactin transport (FIG. 5), indicating that FhuB and FhuG are not involved in staphylobactin transport and that FhuC (as the ATPase), together with SirABC (SirA, binding protein; SirB and SirC, permease) (Dale et al. (2004) *J. Bacteriol.* 186:8356-62; Heinrichs et al. (1999) *J. Bacteriol.* 181: 1436-1443) is involved in staphylobactin transport. Although not observed in the 10-minute timeframe of the transport assays, we observed a reproducibly smaller zone of growth in the 48 hour-duration plate bioassays for staphylobactin utilization by H1071 complemented with pFhuCBG compared with complementation with plasmid pFhuC.

We attribute this observation to the possibility that the expression of the FhuB and FhuG proteins in the former might sequester FhuC into a FhuCBG membrane complex, decreasing the possibility for a potential interaction of FhuC with SirABC and, thus, resulting in a decreased ability to transport iron(III)-staphylobactin. However, we cannot rule out the less likely possibility that the decreased staphylobactin utilization in the strain complemented with pFhuCBG is due to poorer expression of FhuC from this construct compared with the strain complemented with pFhuC. The expression of FhuC from both constructs is governed by identical upstream sequences and, as the strains were grown under identical conditions, it is likely that expression of FhuC was fairly equivalent from both constructs.

Example 11

FhuC Interacts with Additional Iron Transporters

We previously showed that a *S. aureus* sirA mutant was incapable of transporting staphylobactin (Dale et al. (2004) *J. Bacteriol.* 186:8356-62), and that this mutant displayed an iron-deficient growth phenotype. However, the lack of fhuC in H1071 (although H1071 is deleted for fluCBG, recall that plasmid pFhuC complements the growth defect in this strain) results in a more attenuated growth defect in response to iron starvation than a sirA or a sirB mutant (Dale et al. (2004) *J. Bacteriol.* 186:8356-62). Indeed, our use of iron restricted media such as TMS, which contains enough contaminating iron to allow for growth of iron uptake mutants, and the ability to add increasing concentrations of 2,2'-dipyridyl, a non-metabolizable iron chelator, allows us the opportunity to tease apart the contributions of various different iron transporters. Inclusion of 50 µM 2,2'-dipyridyl in TMS strongly attenuates the growth of H1071 compared to wildtype, whereas equivalent growth attenuation is only observed for H306 (RN6390 sirA::Km) and H474 (RN6390 sirB::Tet) when 2,2'-dipyridyl concentrations in TMS are higher than 100 µM (Dale et al. (2004) *J. Bacteriol.* 186:8356-62). Together with previously described results, these observations suggest that not only is FhuC interacting with SirABC to transport staphylobactin, but that FhuC is also interacting with an additional transporter that allows the transport of an as yet undetermined iron chelate. In an attempt to determine what additional iron chelates FhuC may participate in the transport of, we utilized plate bioassays with H1071 using a range of potential iron sources, including enterobactin, ferric citrate, hemin, and hemoglobin. Under these conditions, H1071 was not significantly impaired in the utilization of any of these additional iron sources (data not shown).

Based on these results it is apparent that fhuC is required for the transport of iron(III)-hydroxamate siderophores and the as yet structurally uncharacterized staphylobactin siderophore. The data also support the conclusion that fhuC is likely involved in the transport of an additional iron acquisition system (i.e., in addition to fhu and sir-encoded systems). This is based on the observation that the iron-restricted growth defect displayed by the ΔfhuCBG mutant is more severe than that of either a sirA or sirB mutant during growth in low-iron conditions. At present the identity of the additional pathway(s) affected by the deletion of fhuC is unknown, however, the fhuCBG mutant was still able to utilize hemin, hemoglobin, ferric citrate, and the catechole siderophore enterobactin at levels equivalent to RN6390 in bioassays, demonstrating that the loss of fhuC does not affect the ability of *S. aureus* to obtain iron from these sources. It is tempting to speculate that FhuC interacts with one or both of IsdEF or SA1977-1979 to provide the ATPase component that is genetically unlinked to these transporters. Proteins encoded by the isd locus have been implicated in interactions with host iron complexes (Mack et al. (2004) *Biochem. Biophys. Res. Commun.* 320:781-8; Mazmanian et al. (2003) *Science* 299:906-9; Skaar and Schneewind. (2004) *Microbes Infect.* 6:390-7), complexes that were not present in the TMS laboratory media that was used to demonstrate the iron-restricted growth defect. It was therefore not surprising to find that H1071 was not impaired, compared to wildtype, in heme or hemoglobin uptake. The genetic region surrounding SA1977-1979 contains several open reading frames whose putative products share similarity with siderophore biosynthetic enzymes and it is therefore possible that the lack of FhuC in H1071 abrogates the utilization of another staphylococcal siderophore whose production requires the expression of genes within this locus.

Example 12

The ΔfhuCBG::ermB Mutant Displays an Altered Pathogenicity Profile in a Mouse Kidney Abscess Model We have previously shown that siderophore biosynthesis is important for *S. aureus* virulence in a mouse kidney abscess model (Dale et al. (2004) *Infect. Immun.* 72:29-37). Since we showed that H1071 (RN6390 ΔfhuCBG::ermB) was compromised for staphylobactin uptake, we were interested in determining if this mutant was also attenuated in this model system. Groups of seven Swiss-Webster mice were inoculated with $10^7$ CFU of *S. aureus* Newman or H1074 (Newman ΔfhuCBG::ermB) via the tail vein and the mice were monitored daily for grooming and locomotory function. Each day, the mice were assigned a subjective score that reflected their relative health. For example, mice that received a score of 1 were normal for both grooming and locomotion, whereas mice that received scores of 4 were completely moribund. To account for death prior to the endpoint of the experiment (one mouse infected with Newman died on day 6), we divided clinical scores by the number of days surviving to arrive at a final clinical score. Mice that were injected with H1074 were significantly less moribund than mice injected with *S. aureus* Newman (Table 5; clinical scores of 1.8 vs. 2.7, respectively—a completely healthy mouse would have a clinical score of 1.4.) On day 7, mice were sacrificed and kidneys were removed and evaluated for abscess formation. Eight of fourteen kidneys (57%) removed from mice that were injected with *S. aureus* Newman were abscessed, whereas only 2 of 14 kidneys (14%) removed from mice injected with H1074 showed visible abscess formation. These results were shown to be highly significant (p<0.0001) using the Z-test and Fisher's Exact test. Interestingly, however, when kidney homogenates were plated for enumeration of total bacteria, no significant differences in bacterial load in the kidneys between mice injected with Newman versus H1074 (data not shown).

These results demonstrated that the pathogenicity of a Newman ΔfhuCBG::ermB strain was altered in comparison to the Newman parent strain since, compared to wildtype, the mutant H1074 caused significantly less kidney abscesses and less weight loss without a reduction in bacterial load in the kidneys. These results indicated that the lack of the potential to express FhuCBG (in vivo expression of the fhu genes has not been thus far demonstrated but is inferred based upon their iron-regulated expression profile in vitro) does not affect the ability of the bacteria to persist in vivo, but does seem to lessen their potential to cause more severe infection. These results contrast with previous results showing that a Newman sbnE::Km mutant (unable to produce staphylobactin siderophore) did result in less bacteria in kidneys at 6 days post infection. The fact that expression of FhuCBG, at least in this model system, appears to be required for the full virulence potential of *S. aureus* is in agreement with the conservation of this operon within all *S. aureus* genomes sequenced to date (Sebulsky et al. (2004) *J. Biol. Chem.* 279:53152-9), in contrast to fhuD1 which is absent in the genomes of N315 and MRSA252.

Example 13

Interaction Assays

Assays to screen for agents that disrupt the interaction of Sir polypeptides, staphylobactin, and/or FhuC protein will be conducted as follows. A 96-well microplate with high protein adsorption capacity will be coated with streptavidin overnight at 4° C. at a concentration of 30 µg/ml in 1 times PBS buffer (0.15 M NaCl, pH 6.8). After removal of the solution, the plate will be blocked with 2% BSA in PBS buffer for one or more hours at room temperature. The plate will then be washed and used in the assay. For example, biotinylated SirA and SirB in the absence or presence of a test agent will be incubated for 45 to 60 minutes at room temperature. After three washes with water, an anti-SirB antibody mixed with a secondary antibody conjugated to either alkaline phosphatase (AP) or horseradish peroxidase (HRP) will be added and incubated for one hour. The plate will then be washed to separate the bound from the free antibody complex. A chemiluminescent substrate (alkaline phosphatase or Super Signal luminol solution from Pierce for horseradish peroxidase) will be used to detect bound antibody. A microplate luminometer will be used to detect the chemiluminescent signal. The absence of the signal will indicate that the test agent inhibits or disrupts the binding of sirA to sirB. Similar assays may also be conducted to identify agents that disrupt the interaction of sirA and sirC, sirB and sirC, and/or sirA, sirB, sirC, staphylobactin and/or FhuC.

Example 14

Iron-Transport Assays

Assays to screen for agents that disrupt the iron transport system of *S. aureus* will be conducted as follows. Wild type *S. aureus* cells and SirA deficient *S. aureus* cells will be cultured in tryptic soy broth (TSB) (Difco). Cells will be washed before approximately $10^7$ colony forming units of each strain are inoculated into fresh TMS media in the presence or absence of a test agent. Bacterial growth will be monitored using a Klett meter until late stationary phase was reached. Any other iron-limited media may also be used, e.g., human and animal serum.

A test agent that alters the growth rate of wild type *S. aureus* cells but not SirA deficient cells is likely toxic to cells in the presence of intracellular iron and, therefore, cells importing iron are generally more sensitive to the toxic affects of this drug versus mutants debilitated in iron import.

Similar transport assays may be conducted for SirB, SirC, and FhuC using SirB, SirC, and/or FhuC-deficient cells.

Example 15

Expression Assays

Assays to screen for agents that disrupt the expression of SirA in *S. aureus* will be conducted as follows. Wild type *S. aureus* cells will be cultured overnight in tryptic soy broth (TSB) (Difco) in the presence or absence of a test agent. Following 24 hours of culture, the cells will be washed in 1×PBS (phosphate buffered saline) and then lysed at 37° C. using 10 µg of lysostaphin in STE (0.1M NaCl, 10 mM Tris-HCl [pH 8.0], 1 mM EDTA [pH 8.0]). The cell lysates will then be transferred to anti-SirA antibody precoated plates and incubated for 45 to 60 minutes at room temperature. As a control, cell lysates from untreated *S. aureus* cells will be used. After three washes with water, a secondary antibody conjugated to either alkaline phosphatase (AP) or horseradish peroxidase (HRP) will be added and incubated for one hour. The plate will then be washed to separate the bound from the free antibody complex. A chemiluminescent substrate (alkaline phosphatase or Super Signal luminol solution from Pierce for horseradish peroxidase) will be used to detect bound antibody. A microplate luminometer will be used to detect the chemiluminescent signal. The absence of the signal in samples of cell lysates obtained from cells treated with test agent will indicate that the test agent inhibits the expression of SirA. Similar expression assays may also be conducted for SirB, SirC, staphylobactin, and/or FhuC.

Example 16

Immunogenic Confirmation of SirA in Multiple *S. aureus* Clinical Isolates

This experiment was conducted to confirm the expression of SirA in a panel of clinical isolates of *S. aureus*. Five clinical isolates, representing some of the most pathogenic isolates available, were used in this experiment as identified below:

1. Newman ΔsirA (negative control)
2. Newman Clinical isolate from 1952
3. MN8 (H1878) Toxin-producing clinical isolate
4. Cystic Fibrosis (H1931) Retrieved from a CF patient in Toronto Sick Kids
5. USA300 (H1877) Epidemic CA-MRSA strain
6. USA400 (H1875) Epidemic CA-MRSA strain Whole cells, grown in either iron rich or iron-deplete media, were lysed open and the entire protein content of the cells run on SDS-acrylamide gel to separate proteins. Since *S. aureus* expresses protein A which binds Fc of IgG antibody and therefore results in background bands in *S. aureus* cell lysates, a blot using just the secondary antibody (i.e. no specificity for SirA) was prepared. Reactive bands confirmed expression of protein A by all strains except MN8. When probed with anti-SirA antisera, prepared as described in Example 1, expression of SirA (and therefore reactivity with SirA) was readily observed in all strains, except for the SirA knockout strain (see FIG. 12).

To determine whether the anti-SirA antibody can detect SirA in un-lysed (i.e. whole) *S. aureus* bacterial cells. Whole cells were grown in iron-deplete media only as SirA is not expressed in iron rich media. Cells were then incubated with either secondary antibody alone, or first with anti-SirA antisera followed by secondary. In this example, we used a spa mutant Staph strain (i.e. doesn't express protein A) to eliminate background. The negative control is spa sirA knockout strain. What this shows is that the anti-SirA antisera will bind to SirA expressing cells above the background identified in sirA mutant cells, indicating that the antibody effectively will bind to SirA in whole cells.

Growing cells were incubated with sirA antisera in iron depleted medium. Cells are spun down, washed extensively, and blotted on membrane. Blot is probed with anti-rabbit (IR 800) antibody. SirA antibody bound specifically to Newman protein A mutant, and not to double mutant indicating SirA antibody recognizes at least one epitope in intact cells.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning: A Laboratory Manual*, $2^{nd}$ Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); *Antibodies: A Laboratory Manual*, *and Animal Cell Culture* (R. I. Freshney, ed. (1987)), *Manipulating the Mouse Embryo*, (Cold Spring Harbor Laboratory Press, Cold Spring Harbor, N.Y., 1986).

TABLE 1

Bacterial strains and plasmids used in Examples 2-5

| Bacterial strains, plasmids or oligonucleotides | Description[a] | Source or reference |
|---|---|---|
| *E. coli* | | |
| DH5α | φ80dlacZΔM15 recA1 endA1 gyrA96 thi-1 hsdR17($r_K^-$ $m_K^+$) supE44 relA1 deoR Δ(lacZYA-argF)U169 | Promega |
| ER2566 | Fλ⁻ fhuA2 [lon] ompT lacZ::T7 geneI gal sulA11 Δ(mcrC-mrr)114::IS10 R(mcr-73::miniTn10)2 R(zgb-210::Tn10)1 (Tet$^S$) endA1 [dcm] | New England Biolabs |
| *S. aureus* | | |
| RN4220 | Restriction-deficient; accepts foreign DNA | Lab stock |
| 8325-4 | Prophage-cured wild-type strain | Lab stock |
| RN6390 | Prophage-cured wild-type strain | Lab stock |
| Newman | Clinical isolate; wild-type strain | Lab stock |
| H287 | RN6390fhuG::Tn917; Em$^r$ | Sebulsky[1] |
| H306 | RN6390 sirA::Km; Km$^r$ | This study |
| H474 | RN6390 sirB::Tet; Tet$^r$ | This study |
| H686 | Newman sbnE::Km | Dale[2] |
| H706 | Newmanfur::Km; Km$^r$ | This study |
| H789 | RN6390 sirA::Km, sbnF::pMUTIN4; Km$^r$ Em$^r$ | This study |
| H790 | RN6390 sirA::Km, sbnI::pMUTIN4; Km$^r$ Em$^r$ | This study |
| H791 | RN6390 sirA::Km, sbnA::pMUTIN4; Km$^r$ Emr | This study |
| H796 | RN6390 sirB::Tet sbnF::pMUTIN4; Tet$^r$ Em$^r$ | This study |
| H797 | RN6390 sirB::Tet sbnI::pMUTIN4; Tet$^r$ Em$^r$ | This study |
| H800 | RN6390 sirB::Tet sbnA::pMUTIN4; Tet$^r$ Em$^r$ | This study |
| H803 | Newman sirA::Km: Km$^r$ | This study |
| H804 | Newman sirB::Tet; Tet$^r$ | This study |
| H870 | Newman sbnH::pMUTIN4 | This study |
| H873 | H803 sbnH::pMUTIN4 | This study |
| H876 | H804 sbnH::pMUTIN4 | This study |
| Plasmids | | |
| pGEX-2T-TEV | Expression vector for generating protein fusions with GST that are cleavable with tobacco etch virus protease | Sebulsky[3] |
| pALC2073 | *E. coli* - *S. aureus* shuttle vector, contains $P_{xyl/tet}$; Cm$^r$ | A. Cheung |
| pAUL-A | Temperature sensitive *E. coli* - *S. aureus* shuttle vector; | Chakraborty[4] |
| pAW8 | *E. coli* - *S. aureus* shuttle vector; Tet$^r$ | A. Wada |
| pBC SK+ | *E. coli* phagemid; Cm$^r$ | Stratagene |
| pDG782 | pMLT22 derivative that carries a kanamycin resistance cassette; Ap$^r$ Km$^r$ | Guerout-Fleury[5] |
| pDG1513 | pMLT22 derivative that carries a tetracycline resistance cassette; Cm$^r$ Tet$^r$ | Guerout-Fleury[5] |
| pMTS 12 | pAUL-A derivative carrying sirA::Km; Km$^r$ Em$^r$ | This study |
| pMUTIN4 | lacZ fusion vector; Ap$^r$ (*E. coli*) Em$^r$ (*S. aureus*) | Vaguer[6] |
| pSED43 | pALC2073 derivative carrying the sirB coding region; Cm$^r$ | This study |
| pSED44 | pAW8 derivative carrying sirABC; Tet$^r$ | This study |
| pSirA | pGEX-2T-TEV derivative carrying sirA; Amp$^r$ | This study |
| pSirABC | pBC SK+ carrying sirABC; Cm$^r$ | This study |
| pSirB::Tet3 | pAUL-A derivative carrying sirB::tet; Tet$^r$ Em$^r$ | This study |
| Oligonucleotides[b] | | |
| pSirA (BamHI) | GCAATGGGTACAGGATCCATTAAAGGGAAACCAAAG (SEQ ID NO: 23) | |
| pSirA (EcoRI) | TTGAATTCGTAGCATCGTAAAACTCCTT (SEQ ID NO: 24) | |
| SirB Comp 5' | TTGGTACCGGCGGATATAAATCTTCATT (SEQ ID NO: 25) | |
| SirB Comp 3' | TTGAGCTCTTTCGGTCATAAGCGTTGAC (SEQ ID NO: 26) | |
| Sir Upper | TCACGAAGGAGGCTAATTAG (SEQ ID NO: 27) | |
| Sir Lower | CCTCGCAACGGTTAGTTAAC (SEQ ID NO: 28) | |
| SirB Internal 5' | CAGCTACGGCTACCGAAATA (SEQ ID NO: 29) | |
| SirB Internal 3' | CATTTTTGGGGGCTATTGTTGT (SEQ ID NO: 30) | |
| Gapdh 5' | GGAGGCCATTACCATGGCAG (SEQ ID NO: 31) | |

TABLE 1-continued

Bacterial strains and plasmids used in Examples 2-5

| Bacterial strains, plasmids or oligonucleotides | Description[a] | Source or reference |
|---|---|---|
| Gapdh 3' | TGCTCCCCGCTTACTCATAA (SEQ ID NO: 32) | |

[a] Abbreviations: Cm[r], Tet[r], Em[r], Km[r], Amp[r]: resistance to chloramphenicol, tetracycline, erythromycin, kanamycin and ampicillin, respectively.
[b] Restriction endonuclease recognition sites are underlined.
[1] Sebulsky et al. (2000) J. Bacteriol. 182: 4394-4400
[2] Dale et al. (2004) Infect. Immun. 72: 29-37
[3] Sebulsky et al. (2003) J. Biol. Chem. 278: 49890-900.
[4] Chakraborty et al. (1992) J. Bacteriol. 174: 568-574
[5] Guerout-Fleury et al. (1995) Gene 167: 335-336
[6] Vaguer et al. (1998) Microbiology 144: 3097-3104

TABLE 2

Minimum inhibitory concentrations (MIC) of streptonigrin and 2,2'-dipyridyl against S. aureus Newman and derivatives

| | MIC[a] | |
|---|---|---|
| Bacterial strain | Streptonigrin (ng/ml) | 2,2'-dipyridyl (µM) |
| Newman | 2 | 500 |
| H803 | 8 | 125 |
| H804 | 8 | 125 |
| Newman + 50 µM DESFERAL ® | 2 | nd[b] |
| H803 + 50 µM DESFERAL ® | 2 | nd |
| H804 + 50 µM DESFERAL ® | 2 | nd |

[a] bacteria were grown in TMS
[b] not determined

TABLE 3

β-galactosidase activity from sbn-lacZ fusions in Newman and derivatives grown in iron-restricted media

| Bacterial Strain | Mean (β-galactosidase activity ± SD (RLU/s) |
|---|---|
| Newman | 172 ± 117 |
| H803 | 318 ± 47 |
| H804 | 239 ± 110 |
| H870: Newman sbnH::pMUTIN4 | 825 ± 190 |
| H873: H803 sbnH::pMUTIN4 | 7036 ± 517 |
| H876: H804 sbnH::pMUTIN4 | 3667 ± 1654 |

Values represent the mean values, in triplicate, from assays performed on triplicate cultures

TABLE 4

Bacterial strains and plasmids used in Examples 7-12

| Strain or plasmid | Description[a] | Source or reference |
|---|---|---|
| Strains | | |
| *S. aureus* | | |
| RN4220 | $r_K^- m_K^+$; capable of accepting foreign DNA | Kreiswirth[1] |
| RN6390 | Prophage cured wild-type strain | Peng[2] |
| Newman | Wild-type strain | Duthie[3] |
| H287 | RN6390 fhuG::Tn917; Em[r] | Sebulsky[4] |
| H431 | RN6390 fhuD1::Km fhuD2::Tet; Km[r] Tet[r] | Sebulsky[5] |
| H1068 | RN4220 ΔfhuCBG::ermB; Em[r] | This study |
| H1071 | RN6390 ΔfhuCBG::ermB; Em[r] | This study |
| H1074 | Newman ΔfhuCBG::ermB; Em[r] | This study |
| *E. coli* | | |
| DH5α | φ80dlacZΔM15 recA1 endA1 gyrA96 thi-1 hsdR17($r_k^-$ $m_k^+$) supE44 relA1 deoR Δ(lacZYA-argF)U169 | Promega |
| Plasmids | | |
| pAUL-A | Temperature sensitive S. aureus suicide vector; Em[r] | Chakraborty[6] |
| pAUL-A Km | pAUL-A containing the 1.6-kb kanamycin resistance cassette (inserted as a ClaI fragment) from pDG782; Em[r] Km[r] | This study |
| pDG646 | pSB119 derivative carrying an erythromycin resistance cassette; Ap[r] Em[r] | Guerout-Fluery[7] |
| pDG782 | pMTL22 derivative carrying a kanamycin resistance cassette; Ap[r] Km[r] | Guerout-Fluery[7] |
| pΔFhuCBG | pAULA Km derivative carrying fhuCBG::ermB; Em[r] Km[r] | This study |
| pLI50 | 5.2-kb E. coli/S. aureus shuttle vector; Ap[r] Cm[r] | Lee[8] |
| pUC19 | General purpose E. coli cloning vector; Ap[r] | Sambrook[9] |
| pFhuC | pLI50 containing the S. aureus fhuC gene; Ap[r] Cm[r] | This study |
| pFhuCBG | pLI50 containing the S. aureus fhuCBG operon; Ap[r] Cm[r] | This study |

[a] Abbreviations: Ap[r], Cm[r], Em[r], Km[r], Tet[r] designate resistance to ampicillin, chloramphenicol, erythromycin, kanamycin, and tetracycline, respectively.
[1] Kreiswirth et al. (1983) Nature 305: 680-685.
[2] Peng et al. (1988) J. Bacteriol. 170: 4365-4372.
[3] Duthie and Lorenz (1952) J. Gen. Microbiol. 6: 95-107.
[4] Sebuskly et al. (2000) J. Bacteriol. 182: 4394-4400.
[5] Sebuskly and Heinrichs (2001) J. Bacteriol. 183: 4994-5000.
[6] Chakraborty et al. (1992) J. Bacteriol. 174: 568-574.
[7] Guerout-Fleury et al. (1995) Gene 167: 335-336.
[8] Lee (1992) Mol. Microbiol. 6: 1515-1522.
[9] Sambrook et al. (1989) Molecular Cloning. A laboratory manual, 2nd ed. Cold Spring Harbor Laboratory Press, Cold Spring Harbor.

TABLE 5

Clinical characteristics of mice infected with S. aureus Newman and H1074.

| Mouse Number and Infecting Strain | Abscess Formation* | % Weight Loss (Gain) | Clinical Score[b] |
|---|---|---|---|
| 1-Newman | A/A | 26 | 3.3 |
| 2-Newman | A/A | 33 | 2.9 |
| 3-Newman | A/— | 31 | 2.6 |
| 4-Newman | —/— | 13 | 2.9 |
| 5-Newman[c] | A/A | 43 | 3.8 |
| 6-Newman | —/— | 7 | 1.6 |

TABLE 5-continued

Clinical characteristics of mice infected with *S. aureus* Newman and H1074.

| Mouse Number and Infecting Strain | Abscess Formation* | % Weight Loss (Gain) | Clinical Score[b] |
|---|---|---|---|
| 7-Newman | A/— | 12 | 2.0 |
| Averages:[d] |  | 22.1 ± 4.8 | 2.7 ± 0.3 |
| 1-H1074 | —/— | 8 | 1.4 |
| 2-H1074 | —/— | 19 | 1.7 |
| 3-H1074 | A/A | 33 | 2.7 |
| 4-H1074 | —/— | 26 | 2.4 |
| 5-H1074 | —/— | 15 | 1.9 |
| 6-H1074 | —/— | 4 | 1.4 |
| 7-H1074 | —/— | (1) | 1.4 |
| Averages: |  | 14.8 ± 4.6 | 1.8 ± 0.2 |
| 1-Saline Injection | —/— | (12) | 1.4 |

[a] A/A, both kidneys visibly abscessed; A/—, one kidney visibly abscessed; —/— neither kidney visibly abscessed.
[b] Clinical scores were based on grooming and locomotory ability over the course of the experiment, normalized to the number of days the mice survived.
[c] Mouse was sacrificed on Day 6 due to extreme morbidity.
[d] Averages are ± standard error of the mean.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of inhibiting growth of S. aureus cells comprising the step of exposing the cells to a polynucleotide that includes a portion of SEQ ID No: 14 or SEQ ID No: 15, or about a portion of the first 390 nucleotides of SEQ ID No: 12 or 13, wherein the polynucleotide inhibits expression of FhuC ATPase by hybridizing to an RNA transcript encoding FhuC ATPase, thereby inhibiting growth of S. aureus cells.

2. The method as defined in claim 1, wherein the virulence of the S. aureus cells is decreased.

3. The method as defined in claim 1, additionally comprising the step of exposing said cells to an antimicrobial agent.

4. The method as defined in claim 3, wherein the antimicrobial agent is an iron-chelating antimicrobial agent.

5. The method as defined in claim 1, wherein staphylobactin-mediated iron uptake is inhibited in said cells.

6. The method as defined in claim 1, wherein the polynucleotide is an antisense polynucleotide.

7. The method as defined in claim 1, wherein the polynucleotide includes at least about 15 nucleotides.

8. The method as defined in claim 7, wherein the polynucleotide includes at least about 50 nucleotides.

9. The method as defined in claim 1, wherein the polynucleotide includes a portion of the first 400 nucleotides of SEQ ID NO: 14 or 15.

* * * * *

SEQUENCE LISTING

<160> NUMBER OF SEQ ID NOS: 37

<210> SEQ ID NO 1
<211> LENGTH: 3180
<212> TYPE: DNA
<213> ORGANISM: Staphylococcus aureus

<400> SEQUENCE: 1

```
aaaaaattta attcatacta aatcgtgata atgattctca ttgtcataca tcacgaagga      60
ggctaattag tcaatgaata aagtaattaa aatgcttgtt gttacgcttg ctttcctact     120
tgttttagca ggatgtagtg ggaattcaaa taaacaatca tctgataaca aagataagga    180
aacaacttca attaaacatg caatgggtac aactgaaatt aaagggaaac caaagcgtgt    240
tgttacgcta tatcaaggtg ccactgacgt cgctgtatct ttaggtgtta aacctgtagg    300
tgctgtagaa tcatggacac aaaaaccgaa attcgaatac ataaaaaatg atttaaaaga    360
tactaagatt gtaggtcaag aacctgcacc taacttagag gaaatctcta aattaaaacc    420
ggacttaatt gtcgcgtcaa aagttagaaa tgaaaaagtt tacgatcaat tatctaaaat    480
cgcaccaaca gtttctactg atacagtttt caaattcaaa gatacaacta agttaatggg    540
gaaagcttta gggaaagaaa aagaagctga agatttactt aaaaagtacg atgataaagt    600
agctgcattc caaaaagatg caaagcaaa gtataaagat gcatggccat tgaaagcttc    660
agttgttaac ttccgtgctg atcatacaag aatttatgct ggtggatatg ctggtgaaat    720
cttaaatgat ttaggattca aacgtaataa agacttacaa aaacaagttg ataatggtaa    780
agatattatc caacttacat ctaaagaaag cattccatta atgaacgctg atcatatttt    840
tgtagtaaaa tcagatccaa atgcgaaaga tgctgcatta gttaaaaaga ctgaaagcga    900
atggacttca agtaaagagt ggaaaaattt agacgcagtt aaaaacaacc aagtatctga    960
tgatttagat gaaatcactt ggaacttagc tggcggatat aaatcttcat taaaacttat   1020
tgacgattta tatgaaaagt taaatattga aaaacaatca aataattaa ggagttttac    1080 gatgctactt aaaccaaaat accaaatcgt tattgctggt ttatgtcttg caatagtagc   1140
tatcttaagt ttaatgattg gaaatacgct tgtgtcacca ggtacggtga tacaggcgtt   1200
```

-continued

```
attcaacttt gatagtgaaa acgatttaca tgatgttgtc actggtgcac gggcgtcgag   1260
aacaatcatt gcgttattga ctggtgctgc ccttgctgtc tcaggtttgt tgatgcaagc   1320
acttacacga aacccaatag cctcaccagg gcttttcggt gtcaatgcag gcgcagtatt   1380
ttttgtcatt tttagtatta catttatcca aattcaatct tttaaaatga ttgtagttat   1440 tgcattttg ggggctattg ttgttactgt attagttgtt gcactaggta tgtttagaca   1500
aacactattc tcacctcacc gtgtcatttt ggcaggtgct gcgattgcga tgctatttac   1560
agcctttact caaggcatac ttattatgaa cgaaacagac ttacaaggcc tattattttg   1620
gttaagtggc tccgtttcat tacgtaatat ttgggatatc ccatggatta ttccgcttgt   1680
attgatactt attttaattg catttagcat ggctgcacac atcaacatct tgatgacaag   1740
tgacgacatt gcaaccggcc tcggtcaaaa cataaaatta atcaaatgga tgattattat   1800
gctcatcagt atgttagccg gtatttcggt agccgtagct ggatcaatcg tctttgtggg   1860
tcttatcgta ccgaatatta gcaaacgatt attaccacca aactataagt atttaattcc   1920
ttttactgca ttagctggag caatcctaat gatcatttca gacattgttg ctcgtataat   1980
aattaagcca ctagagttgc ctatcggtgt cgttaccgct gtcattggcg ctattgtctt   2040
aatctatatt atgaagaaag gacgtcaacg cttatgaccg aaaagattaa taaaaaagac   2100
aattaccatc tcatcttcgc gttaatcttt ttagccatcg tttcagtggt aagtatgatg   2160
attggttcaa gctttatacc attacaacgc gtactgatgt actttataaa tccaaatgac   2220
agtatggatc aattcacttt agaagtatta cgcttacctc gcattacact tgcgatttta   2280
gcaggtgccg cactaggaat gagtggttta atgttgcaaa atgtattaaa aaatccaatt   2340
gcctcacctg atattatcgg tatcacaggt ggtgctagct taagtgctgt tgtctttatt   2400 gcattttca gccatttaac aatacattta cttccactat ttgcagtatt aggtggcgca   2460
gttgcaatga tgatactatt agtgtttcaa acgaaaggac aaatacgccc gacaacactc   2520
ataatcatcg gtatttcgat gcaaacgttg tttattgcgc ttgtccaagg attactcatt   2580
acaacgaagc aattatctgc tgccaaagct tatacatggc tagtcggaag tctttacggt   2640
gctacgttta aagatacaat cattttgggt atggttattt tagctgttgt gccgttgtta   2700
tttcttgtta taccaaaaat gaaaatatct atacttgatg accctgtagc gattggctta   2760
ggcttacatg tacaacgtat gaaactaatc caattaatca cttctactat actcgtatct   2820
atggcaatca gtttagtagg taacattggg tttgtcggtt taatcgcacc acatatcgcg   2880
aaaacaatcg ttcgcggaag ttatgctaaa aagttactaa tgtcagcaat gattggtgcc   2940
atatcaattg ttattgcaga cttaattggg cgtaccttat tcttgcctaa agaagtgcca   3000
gcaggtgtat ttattgctgc ttttggtgcc ccattcttca tatacttatt attaccgtg   3060 aaaaagttat aacgatatta ttaaaacaaa atgacctcac aacgaagtta gctaaatgat   3120
tcagttaact aaccgttgcg aggtttttt atacatatag ttgttgttat tgttaacaag   3180
```

<210> SEQ ID NO 2
<211> LENGTH: 3180
<212> TYPE: DNA
<213> ORGANISM: Staphylococcus aureus

<400> SEQUENCE: 2

```
cttgttaaca ataacaacaa ctatatgtat aaaaaaacct cgcaacggtt agttaactga     60
atcatttagc taacttcgtt gtgaggtcat tttgttttaa taatatcgtt ataacttttt    120
cacggttaat aataagtata tgaagaatgg ggcaccaaaa gcagcaataa atacacctgc    180
```

```
tggcacttct ttaggcaaga ataaggtacg cccaattaag tctgcaataa caattgatat    240
ggcaccaatc attgctgaca ttagtaactt tttagcataa cttccgcgaa cgattgtttt    300
cgcgatatgt ggtgcgatta aaccgacaaa cccaatgtta cctactaaac tgattgccat    360
agatacgagt atagtagaag tgattaattg gattagtttc atacgttgta catgtaagcc    420
taagccaatc gctacagggt catcaagtat agatattttc attttggta taacaagaaa    480 taacaacggc acaacagcta aaataaccat acccaaaatg attgtatctt taaacgtagc    540
accgtaaaga cttccgacta gccatgtata agctttggca gcagataatt gcttcgttgt    600
aatgagtaat ccttggacaa gcgcaataaa caacgtttgc atcgaaatac cgatgattat    660
gagtgttgtc gggcgtattt gtcctttcgt ttgaaacact aatagtatca tcattgcaac    720
tgcgccacct aatactgcaa atagtggaag taaatgtatt gttaaatggc tgaaaaatgc    780
aataaagaca acagcactta agctagcacc acctgtgata ccgataatat caggtgaggc    840
aattggattt tttaatacat tttgcaacat taaaccactc attcctagtg cggcacctgc    900
taaaatcgca agtgtaatgc gaggtaagcg taatacttct aaagtgaatt gatccatact    960
gtcatttgga tttataaagt acatcagtac gcgttgtaat ggtataaagc ttgaaccaat   1020
catcatactt accactgaaa cgatggctaa aaagattaac gcgaagatga gatggtaatt   1080 gtcttttta ttaatctttt cggtcataag cgttgacgtc ctttcttcat aatatagatt   1140
aagacaatag cgccaatgac agcggtaacg acaccgatag gcaactctag tggcttaatt   1200
attatacgag caacaatgtc tgaaatgatc attaggattg ctccagctaa tgcagtaaaa   1260
ggaattaaat acttatagtt tggtggtaat aatcgtttgc taatattcgg tacgataaga   1320
cccacaaaga cgattgatcc agctacggct accgaaatac cggctaacat actgatgagc   1380
ataataatca tccatttgat taattttatg ttttgaccga ggccggttgc aatgtcgtca   1440
cttgtcatca agatgttgat gtgtgcagcc atgctaaatg caattaaaat aagtatcaat   1500
acaagcggaa taatccatgg gatatcccaa atattacgta atgaaacgga gccacttaac   1560
caaaataata ggccttgtaa gtctgtttcg ttcataataa gtatgccttg agtaaaggct   1620
gtaaatagca tcgcaatcgc agcacctgcc aaaatgacac ggtgaggtga aatagtgtt   1680 tgtctaaaca tacctagtgc aacaactaat acagtaacaa caatagcccc caaaaatgca   1740
ataactacaa tcattttaaa agattgaatt tggataaatg taatactaaa aatgacaaaa   1800
aatactgcgc ctgcattgac accgaaaagc cctggtgagg ctattgggtt tcgtgtaagt   1860
gcttgcatca caaacctga gacagcaagg gcagcaccag tcaataacgc aatgattgtt   1920
ctcgacgccc gtgcaccagt gacaacatca tgtaaatcgt tttcactatc aaagttgaat   1980
aacgcctgta tcaccgtacc tggtgacaca agcgtatttc caatcattaa acttaagata   2040
gctactattg caagacataa accagcaata acgatttggt attttggttt aagtagcatc   2100
gtaaaactcc ttaattattt tgattgtttt tcaatattta acttttcata taaatcgtca   2160
ataagtttta atgaagattt atatccgcca gctaagttcc aagtgatttc atctaaatca   2220
tcagatactt ggttgttttt aactgcgtct aaatttttcc actctttact tgaagtccat   2280
tcgctttcag tcttttaac taatgcagca tctttcgcat ttggatctga ttttactaca   2340
aaaatatgat cagcgttcat taatggaatg ctttctttag atgtaagttg gataatatct   2400
ttaccattat caacttgttt ttgtaagtct ttattacgtt tgaatcctaa atcatttaag   2460
atttcaccag catatccacc agcataaatt cttgtatgat cagcacggaa gttaacaact   2520
gaagctttca atggccatgc atctttatac tttgcttttg catctttttg gaatgcagct   2580
```

| | | | | |
|---|---|---|---|---|
| actttatcat | cgtacttttt | aagtaaatct | tcagcttctt | tttctttccc | taaagctttc | 2640 |
| cccattaact | tagttgtatc | tttgaatttg | aaaactgtat | cagtagaaac | tgttggtgcg | 2700 |
| attttagata | attgatcgta | aacttttca | tttctaactt | ttgacgcgac | aattaagtcc | 2760 |
| ggttttaatt | tagagatttc | ctctaagtta | ggtgcaggtt | cttgacctac | aatcttagta | 2820 |
| tcttttaaat | cattttttat | gtattcgaat | tcggttttt | gtgtccatga | ttctacagca | 2880 |
| cctacaggtt | taacacctaa | agatacagcg | acgtcagtgg | caccttgata | tagcgtaaca | 2940 |
| acacgctttg | gtttcccttt | aatttcagtt | gtacccattg | catgtttaat | tgaagttgtt | 3000 |
| tccttatctt | tgttatcaga | tgattgttta | tttgaattcc | cactcatcc | tgctaaaaca | 3060 |
| agtaggaaag | caagcgtaac | aacaagcatt | ttaattactt | tattcattga | ctaattagcc | 3120 |
| tccttcgtga | tgtatgacaa | tgagaatcat | tatcacgatt | tagtatgaat | taaatttttt | 3180 |

<210> SEQ ID NO 3
<211> LENGTH: 993
<212> TYPE: DNA
<213> ORGANISM: Staphylococcus aureus

<400> SEQUENCE: 3

| | | | | |
|---|---|---|---|---|
| atgaataaag | taattaaaat | gcttgttgtt | acgcttgctt | tcctacttgt | tttagcagga | 60 |
| tgtagtggga | attcaaataa | acaatcatct | gataacaaag | ataaggaaac | aacttcaatt | 120 |
| aaacatgcaa | tgggtacaac | tgaaattaaa | gggaaaccaa | agcgtgttgt | tacgctatat | 180 |
| caaggtgcca | ctgacgtcgc | tgtatcttta | ggtgttaaac | ctgtaggtgc | tgtagaatca | 240 |
| tggacacaaa | aaccgaaatt | cgaatacata | aaaaatgatt | taaagatac | taagattgta | 300 |
| ggtcaagaac | ctgcacctaa | cttagaggaa | atctctaaat | taaaaccgga | cttaattgtc | 360 |
| gcgtcaaaag | ttagaaatga | aaaagtttac | gatcaattat | ctaaaatcgc | accaacagtt | 420 |
| tctactgata | cagttttcaa | attcaaagat | acaactaagt | taatgggaa | agctttaggg | 480 |
| aaagaaaaag | aagctgaaga | tttacttaaa | aagtacgatg | ataaagtagc | tgcattccaa | 540 |
| aaagatgcaa | aagcaaagta | taagatgca | tggccattga | aagcttcagt | tgttaacttc | 600 |
| cgtgctgatc | atacaagaat | ttatgctggt | ggatatgctg | tgaaatctt | aaatgattta | 660 |
| ggattcaaac | gtaataaaga | cttacaaaaa | caagttgata | atggtaaaga | tattatccaa | 720 |
| cttacatcta | aagaaagcat | tccattaatg | aacgctgatc | atattttgt | agtaaaatca | 780 |
| gatccaaatg | cgaaagatgc | tgcattagtt | aaaaagactg | aaagcgaatg | gacttcaagt | 840 |
| aaaagagtgga | aaaatttaga | cgcagttaaa | aacaaccaag | tatctgatga | tttagatgaa | 900 |
| atcacttgga | acttagctgg | cggatataaa | tcttcattaa | aacttattga | cgatttatat | 960 |
| gaaaagttaa | atattgaaaa | acaatcaaaa | taa | | | 993 |

<210> SEQ ID NO 4
<211> LENGTH: 993
<212> TYPE: DNA
<213> ORGANISM: Staphylococcus aureus

<400> SEQUENCE: 4

| | | | | |
|---|---|---|---|---|
| ttatttgat | tgtttttcaa | tatttaactt | ttcatataaa | tcgtcaataa | gttttaatga | 60 |
| agatttatat | ccgccagcta | agttccaagt | gatttcatct | aaatcatcag | atacttggtt | 120 |
| gttttaact | gcgtctaaat | ttttccactc | tttacttgaa | gtccattcgc | tttcagtctt | 180 |
| tttaactaat | gcagcatctt | tcgcatttgg | atctgatttt | actacaaaaa | tatgatcagc | 240 |
| gttcattaat | ggaatgcttt | ctttagatgt | aagttggata | atatctttac | cattatcaac | 300 |

```
ttgttttgt aagtctttat tacgtttgaa tcctaaatca tttaagattt caccagcata    360
tccaccagca taaattcttg tatgatcagc acgaagtta acaactgaag ctttcaatgg    420
ccatgcatct ttatactttg cttttgcatc ttttggaat gcagctactt tatcatcgta    480 cttttaagt aaatcttcag cttcttttc tttccctaaa gctttcccca ttaacttagt    540
tgtatctttg aatttgaaaa ctgtatcagt agaaactgtt ggtgcgattt tagataattg    600
atcgtaaact ttttcatttc taacttttga cgcgacaatt aagtccggtt ttaatttaga    660
gatttcctct aagttaggtg caggttcttg acctacaatc ttagtatctt ttaaatcatt    720
ttttatgtat tcgaatttcg ttttttgtgt ccatgattct acagcaccta caggtttaac    780
acctaaagat acagcgacgt cagtggcacc ttgatatagc gtaacaacac gctttggttt    840 cccttaatt tcagttgtac ccattgcatg tttaattgaa gttgttcct tatctttgtt    900 atcagatgat tgtttatttg aattcccact acatcctgct aaaacaagta ggaaagcaag    960
cgtaacaaca agcattttaa ttactttatt cat                                993
```

```
<210> SEQ ID NO 5
<211> LENGTH: 330
<212> TYPE: PRT
<213> ORGANISM: Staphylococcus aureus

<400> SEQUENCE: 5

Met Asn Lys Val Ile Lys Met Leu Val Val Thr Leu Ala Phe Leu Leu
1               5                   10                  15

Val Leu Ala Gly Cys Ser Gly Asn Ser Asn Lys Gln Ser Ser Asp Asn
            20                  25                  30

Lys Asp Lys Glu Thr Thr Ser Ile Lys His Ala Met Gly Thr Thr Glu
        35                  40                  45

Ile Lys Gly Lys Pro Lys Arg Val Val Thr Leu Tyr Gln Gly Ala Thr
    50                  55                  60

Asp Val Ala Val Ser Leu Gly Val Lys Pro Val Gly Ala Val Glu Ser
65                  70                  75                  80

Trp Thr Gln Lys Pro Lys Phe Glu Tyr Ile Lys Asn Asp Leu Lys Asp
                85                  90                  95

Thr Lys Ile Val Gly Gln Glu Pro Ala Pro Asn Leu Glu Glu Ile Ser
            100                 105                 110

Lys Leu Lys Pro Asp Leu Ile Val Ala Ser Lys Val Arg Asn Glu Lys
        115                 120                 125

Val Tyr Asp Gln Leu Ser Lys Ile Ala Pro Thr Val Ser Thr Asp Thr
    130                 135                 140

Val Phe Lys Phe Lys Asp Thr Thr Lys Leu Met Gly Lys Ala Leu Gly
145                 150                 155                 160

Lys Glu Lys Glu Ala Glu Asp Leu Leu Lys Lys Tyr Asp Asp Lys Val
                165                 170                 175

Ala Ala Phe Gln Lys Asp Ala Lys Ala Lys Tyr Lys Asp Ala Trp Pro
            180                 185                 190

Leu Lys Ala Ser Val Val Asn Phe Arg Ala Asp His Thr Arg Ile Tyr
        195                 200                 205

Ala Gly Gly Tyr Ala Gly Glu Ile Leu Asn Asp Leu Gly Phe Lys Arg
    210                 215                 220

Asn Lys Asp Leu Gln Lys Gln Val Asp Asn Gly Lys Asp Ile Ile Gln
225                 230                 235                 240

Leu Thr Ser Lys Glu Ser Ile Pro Leu Met Asn Ala Asp His Ile Phe
                245                 250                 255
```

| Val | Val | Lys | Ser | Asp | Pro | Asn | Ala | Lys | Asp | Ala | Ala | Leu | Val | Lys | Lys |
|---|---|---|---|---|---|---|---|---|---|---|---|---|---|---|---|
| | | | 260 | | | | 265 | | | | 270 | | | | |

| Thr | Glu | Ser | Glu | Trp | Thr | Ser | Lys | Glu | Trp | Lys | Asn | Leu | Asp | Ala |
|---|---|---|---|---|---|---|---|---|---|---|---|---|---|---|
| | | | 275 | | | | 280 | | | | | 285 | | |

| Val | Lys | Asn | Asn | Gln | Val | Ser | Asp | Asp | Leu | Asp | Glu | Ile | Thr | Trp | Asn |
|---|---|---|---|---|---|---|---|---|---|---|---|---|---|---|---|
| 290 | | | | | 295 | | | | | 300 | | | | | |

| Leu | Ala | Gly | Gly | Tyr | Lys | Ser | Ser | Leu | Lys | Leu | Ile | Asp | Asp | Leu | Tyr |
|---|---|---|---|---|---|---|---|---|---|---|---|---|---|---|---|
| 305 | | | | 310 | | | | | 315 | | | | | 320 | |

| Glu | Lys | Leu | Asn | Ile | Glu | Lys | Gln | Ser | Lys |
|---|---|---|---|---|---|---|---|---|---|
| | | | | 325 | | | | 330 | |

<210> SEQ ID NO 6
<211> LENGTH: 996
<212> TYPE: DNA
<213> ORGANISM: Staphylococcus aureus

<400> SEQUENCE: 6

```
atgctactta aaccaaaata ccaaatcgtt attgctggtt tatgtcttgc aatagtagct      60
atcttaagtt taatgattgg aaatacgctt gtgtcaccag gtacggtgat acaggcgtta     120
ttcaactttg atagtgaaaa cgatttacat gatgttgtca ctggtgcacg ggcgtcgaga     180
acaatcattg cgttattgac tggtgctgcc cttgctgtct caggtttgtt gatgcaagca     240
cttacacgaa acccaatagc ctcaccaggg cttttcggtg tcaatgcagg cgcagtattt     300
tttgtcattt ttagtattac atttatccaa attcaatctt ttaaaatgat gtagttatt      360
gcatttttgg gggctattgt tgttactgta ttagttgttg cactaggtat gtttagacaa     420
acactattct cacctcaccg tgtcattttg gcaggtgctg cgattgcgat gctatttaca     480
gcctttactc aaggcatact tattatgaac gaaacagact tacaaggcct attattttgg     540
ttaagtggct ccgtttcatt acgtaatatt tgggatatcc catggattat tccgcttgta     600
ttgatactta ttttaattgc atttagcatg gctgcacaca tcaacatctt gatgacaagt     660
gacgacattg caaccggcct cggtcaaaac ataaaattaa tcaaatggat gattattatg     720
ctcatcagta tgttagccgg tatttcggta gccgtagctg atcaatcgt ctttgtgggt     780
cttatcgtac cgaatattag caaacgatta ttaccaccaa actataagta tttaattcct     840
tttactgcat tagctggagc aatcctaatg atcatttcag acattgttgc tcgtataata     900
attaagccac tagagttgcc tatcggtgtc gttaccgctg tcattggcgc tattgtctta     960
atctatatta tgaagaaagg acgtcaacgc ttatga                              996
```

<210> SEQ ID NO 7
<211> LENGTH: 996
<212> TYPE: DNA
<213> ORGANISM: Staphylococcus aureus

<400> SEQUENCE: 7

```
tcataagcgt tgacgtcctt tcttcataat atagattaag acaatagcgc caatgacagc      60
ggtaacgaca ccgataggca actctagtgg cttaattatt atacgagcaa caatgtctga     120
aatgatcatt aggattgctc cagctaatgc agtaaaagga attaaatact tatagtttgg     180
tggtaataat cgtttgctaa tattcggtac gataagaccc acaaagacga ttgatccagc     240
tacggctacc gaaataccgg ctaacatact gatgagcata ataatcatcc atttgattaa     300
ttttatgttt tgaccgaggc cggttgcaat gtcgtcactt gtcatcaaga tgttgatgtg     360
tgcagccatg ctaaatgcaa ttaaaataag tatcaataca agcggaataa tccatgggat     420
atcccaaata ttacgtaatg aaacggagcc acttaaccaa aataataggc cttgtaagtc     480
```

```
tgtttcgttc ataataagta tgccttgagt aaaggctgta aatagcatcg caatcgcagc    540
acctgccaaa atgacacggt gaggtgagaa tagtgtttgt ctaaacatac ctagtgcaac    600
aactaataca gtaacaacaa tagcccccaa aaatgcaata actacaatca ttttaaaaga    660
ttgaatttgg ataaatgtaa tactaaaaat gacaaaaaat actgcgcctg cattgacacc    720
gaaaagccct ggtgaggcta ttgggtttcg tgtaagtgct tgcatcaaca aacctgagac    780
agcaagggca gcaccagtca ataacgcaat gattgttctc gacgcccgtg caccagtgac    840
aacatcatgt aaatcgtttt cactatcaaa gttgaataac gcctgtatca ccgtacctgg    900
tgacacaagc gtatttccaa tcattaaact taagatagct actattgcaa gacataaacc    960
agcaataacg atttggtatt ttggtttaag tagcat                              996
```

<210> SEQ ID NO 8
<211> LENGTH: 331
<212> TYPE: PRT
<213> ORGANISM: Staphylococcus aureus

<400> SEQUENCE: 8

```
Met Leu Leu Lys Pro Lys Tyr Gln Ile Val Ile Ala Gly Leu Cys Leu
1               5                   10                  15

Ala Ile Val Ala Ile Leu Ser Leu Met Ile Gly Asn Thr Leu Val Ser
            20                  25                  30

Pro Gly Thr Val Ile Gln Ala Leu Phe Asn Phe Asp Ser Glu Asn Asp
        35                  40                  45

Leu His Asp Val Val Thr Gly Ala Arg Ala Ser Arg Thr Ile Ile Ala
    50                  55                  60

Leu Leu Thr Gly Ala Ala Leu Ala Val Ser Gly Leu Leu Met Gln Ala
65                  70                  75                  80

Leu Thr Arg Asn Pro Ile Ala Ser Pro Gly Leu Phe Gly Val Asn Ala
                85                  90                  95

Gly Ala Val Phe Phe Val Ile Phe Ser Ile Thr Phe Ile Gln Ile Gln
            100                 105                 110

Ser Phe Lys Met Ile Val Val Ile Ala Phe Leu Gly Ala Ile Val Val
        115                 120                 125

Thr Val Leu Val Val Ala Leu Gly Met Phe Arg Gln Thr Leu Phe Ser
    130                 135                 140

Pro His Arg Val Ile Leu Ala Gly Ala Ala Ile Ala Met Leu Phe Thr
145                 150                 155                 160

Ala Phe Thr Gln Gly Ile Leu Ile Met Asn Glu Thr Asp Leu Gln Gly
                165                 170                 175

Leu Leu Phe Trp Leu Ser Gly Ser Val Ser Leu Arg Asn Ile Trp Asp
            180                 185                 190

Ile Pro Trp Ile Ile Pro Leu Val Leu Ile Leu Ile Leu Ile Ala Phe
        195                 200                 205

Ser Met Ala Ala His Ile Asn Ile Leu Met Thr Ser Asp Asp Ile Ala
    210                 215                 220

Thr Gly Leu Gly Gln Asn Ile Lys Leu Ile Lys Trp Met Ile Ile Met
225                 230                 235                 240

Leu Ile Ser Met Leu Ala Gly Ile Ser Val Ala Val Ala Gly Ser Ile
                245                 250                 255

Val Phe Val Gly Leu Ile Val Pro Asn Ile Ser Lys Arg Leu Leu Pro
            260                 265                 270

Pro Asn Tyr Lys Tyr Leu Ile Pro Phe Thr Ala Leu Ala Gly Ala Ile
        275                 280                 285
```

```
Leu Met Ile Ile Ser Asp Ile Val Ala Arg Ile Ile Lys Pro Leu
    290                 295                 300

Glu Leu Pro Ile Gly Val Val Thr Ala Val Ile Gly Ala Ile Val Leu
305                 310                 315                 320

Ile Tyr Ile Met Lys Lys Gly Arg Gln Arg Leu
                325                 330

<210> SEQ ID NO 9
<211> LENGTH: 999
<212> TYPE: DNA
<213> ORGANISM: Staphylococcus aureus

<400> SEQUENCE: 9
atgaccgaaa agattaataa aaaagacaat taccatctca tcttcgcgtt aatcttttta    60
gccatcgttt cagtggtaag tatgatgatt ggttcaagct ttataccatt acaacgcgta   120
ctgatgtact ttataaatcc aaatgacagt atggatcaat tcactttaga agtattcgc   180 ttacctcgca ttacacttgc gattttagca ggtgccgcac taggaatgag tggtttaatg   240
ttgcaaaatg tattaaaaaa tccaattgcc tcacctgata ttatcggtat cacaggtggt   300
gctagcttaa gtgctgttgt ctttattgca ttttcagcc atttaacaat acatttactt   360
ccactatttg cagtattagg tggcgcagtt gcaatgatga tactattagt gtttcaaacg   420
aaaggacaaa tacgcccgac aacactcata atcatcggta tttcgatgca aacgttgttt   480
attgcgcttg tccaaggatt actcattaca acgaagcaat tatctgctgc aaaagcttat   540
acatggctag tcggaagtct ttacggtgct acgtttaaag atacaatcat tttgggtatg   600
gttattttag ctgttgtgcc gttgttattt cttgttatac caaaaatgaa atatctata   660 cttgatgacc ctgtagcgat tggcttaggc ttacatgtac aacgtatgaa actaatccaa   720
ttaatcactt ctactatact cgtatctatg caatcagtt tagtaggtaa cattgggttt   780
gtcggtttaa tcgcaccaca tatcgcgaaa acaatcgttc gcggaagtta tgctaaaaag   840
ttactaatgt cagcaatgat tggtgccata tcaattgtta ttgcagactt aattgggcgt   900
accttattct tgcctaaaga agtgccagca ggtgtattta ttgctgcttt tggtgcccca   960
ttcttcatat acttattatt aaccgtgaaa aagttataa                          999

<210> SEQ ID NO 10
<211> LENGTH: 999
<212> TYPE: DNA
<213> ORGANISM: Staphylococcus aureus

<400> SEQUENCE: 10
ttataacttt ttcacggtta ataataagta tatgaagaat ggggcaccaa aagcagcaat    60
aaatacacct gctggcactt ctttaggcaa gaataaggta cgcccaatta agtctgcaat   120
aacaattgat atggcaccaa tcattgctga cattagtaac tttttagcat aacttccgcg   180
aacgattgtt ttcgcgatat gtggtgcgat taaaccgaca aacccaatgt tacctactaa   240
actgattgcc atagatacga gtatagtaga agtgattaat tggattagtt tcatacgttg   300
tacatgtaag cctaagccaa tcgctacagg gtcatcaagt atagatattt tcattttgg   360 tataacaaga ataacaacg gcacaacagc taaaataacc atacccaaaa tgattgtatc   420
tttaaacgta gcaccgtaaa gacttccgac tagccatgta taagctttgg cagcagataa   480
ttgcttcgtt gtaatgagta atccttggac aagcgcaata acaacgtttt gcatcgaaat   540
accgatgatt atgagtgttg tcgggcgtat ttgtcctttc gtttgaaaca ctaatagtat   600
```

```
catcattgca actgcgccac ctaatactgc aaatagtgga agtaaatgta ttgttaaatg    660
gctgaaaaat gcaataaaga caacagcact taagctagca ccacctgtga taccgataat    720
atcaggtgag gcaattggat tttttaatac attttgcaac attaaaccac tcattcctag    780
tgcggcacct gctaaaatcg caagtgtaat gcgaggtaag cgtaatactt ctaaagtgaa    840
ttgatccata ctgtcatttg gatttataaa gtacatcagt acgcgttgta atggtataaa    900
gcttgaacca atcatcatac ttaccactga aacgatggct aaaaagatta acgcgaagat    960
gagatggtaa ttgtcttttt tattaatctt ttcggtcat                           999

<210> SEQ ID NO 11
<211> LENGTH: 332
<212> TYPE: PRT
<213> ORGANISM: Staphylococcus aureus

<400> SEQUENCE: 11

Met Thr Glu Lys Ile Asn Lys Lys Asp Asn Tyr His Leu Ile Phe Ala
1               5                   10                  15

Leu Ile Phe Leu Ala Ile Val Ser Val Ser Met Met Ile Gly Ser
            20                  25                  30

Ser Phe Ile Pro Leu Gln Arg Val Leu Met Tyr Phe Ile Asn Pro Asn
        35                  40                  45

Asp Ser Met Asp Gln Phe Thr Leu Glu Val Leu Arg Leu Pro Arg Ile
    50                  55                  60

Thr Leu Ala Ile Leu Ala Gly Ala Ala Leu Gly Met Ser Gly Leu Met
65                  70                  75                  80

Leu Gln Asn Val Leu Lys Asn Pro Ile Ala Ser Pro Asp Ile Ile Gly
                85                  90                  95

Ile Thr Gly Gly Ala Ser Leu Ser Ala Val Val Phe Ile Ala Phe Phe
            100                 105                 110

Ser His Leu Thr Ile His Leu Leu Pro Leu Phe Ala Val Leu Gly Gly
        115                 120                 125

Ala Val Ala Met Met Ile Leu Leu Val Phe Gln Thr Lys Gly Gln Ile
    130                 135                 140

Arg Pro Thr Thr Leu Ile Ile Ile Gly Ile Ser Met Gln Thr Leu Phe
145                 150                 155                 160

Ile Ala Leu Val Gln Gly Leu Leu Ile Thr Thr Lys Gln Leu Ser Ala
                165                 170                 175

Ala Lys Ala Tyr Thr Trp Leu Val Gly Ser Leu Tyr Gly Ala Thr Phe
            180                 185                 190

Lys Asp Thr Ile Ile Leu Gly Met Val Ile Leu Ala Val Val Pro Leu
        195                 200                 205

Leu Phe Leu Val Ile Pro Lys Met Lys Ile Ser Ile Leu Asp Asp Pro
    210                 215                 220

Val Ala Ile Gly Leu Gly Leu His Val Gln Arg Met Lys Leu Ile Gln
225                 230                 235                 240

Leu Ile Thr Ser Thr Ile Leu Val Ser Met Ala Ile Ser Leu Val Gly
                245                 250                 255

Asn Ile Gly Phe Val Gly Leu Ile Ala Pro His Ile Ala Lys Thr Ile
            260                 265                 270

Val Arg Gly Ser Tyr Ala Lys Lys Leu Leu Met Ser Ala Met Ile Gly
        275                 280                 285

Ala Ile Ser Ile Val Ile Ala Asp Leu Ile Gly Arg Thr Leu Phe Leu
    290                 295                 300

Pro Lys Glu Val Pro Ala Gly Val Phe Ile Ala Ala Phe Gly Ala Pro
```

| | | | | |
|---|---|---|---|---|
| 305 | 310 | 315 | 320 | |

Phe Phe Ile Tyr Leu Leu Leu Thr Val Lys Lys Leu
                  325                  330

<210> SEQ ID NO 12
<211> LENGTH: 3728
<212> TYPE: DNA
<213> ORGANISM: Staphylococcus aureus

<400> SEQUENCE: 12

```
tttggatcca caagtttcaa aagcaaagcg attaattaaa caaatcgata aagatgcatt    60
cctcgtaatt catgatgtaa gagatgtcta tggtaatggc tttcttgcag atgaataaat   120
aaatggtatg agcacacata cttaaataga agtccacgga caagttttttg aactatgaag   180
acttatctgt gggcgttttt tattttataa agtaatata caagacatga caaatcgagc   240
tatccaattt aaaaagtaat gttagtcaat aagattgaaa atgttataa tgatgttcat   300
gataatcatt atcaattggg atgtctttga aaattgataa tttaaaaata gaaattattt   360
tttataaaca gaaagaattt tattgaaagt agggaaatta tgaatcgttt gcatggacaa   420
caagttaaaa ttggttacgg ggataacacg attataaata aattagatgt tgaaatacca   480
gatggcaaag tgacgtcaat cattggtcct aacggctgcg ggaaatctac tttgctaaag   540
gcattgtcac gtttattggc agttaaagaa ggcgaagtat ttttagatgg tgaaaatatt   600
catacacaat ctacgaaaga gattgcaaaa aaaatagcca ttttacctca atcacctgaa   660
gtagcagatg gcttaactgt tggggaatta gtttcatatg gtcgttttcc acatcaaaaa   720
ggatttggta gattaactgc tgaggataag aaagaaattg attgggcaat ggaagttaca   780
ggaactgata cattccgaca ccgttcaatc aatgatttaa gtggtggtca agacaacgt   840
gtttggattg caatggcatt agcacaaaga actgatatta tcttttttaga cgaaccaaca   900
acatatttag atatctgtca tcaattagaa atactagaat tagttcagaa gctaaatcag   960
gaacaaggtt gtacaattgt catggttctt catgatatca accaagcgat tcgtttctca  1020
gatcatctta ttgcgatgaa agaaggggat atcatcgcta caggttcaac agaagacgta  1080
ttaacacagg aaatattaga aaaagttttt aatattgatg ttgttttaag taaagatcct  1140
aaaactggaa aacctttact ggtaacttat gacttatgtc gcagagctta ttcttaatta  1200
agtaagttaa tatgataaaa aggacaatta acatgacaaa tagagagaac ccaacgccat  1260
tgaagttttt atcctatatt ataggtttaa gtatgatact actaatcaca ctatttattt  1320
ctacattaat aggtgacgcc aaaattcaag cctctacaat tatagaggct atttttaatt  1380
ataatcctag caatcaacag caaaacatca tcaatgagat taggattccc agaaatatag  1440
cagcagtaat tgtaggtatg gcgcttgcag tttctggtgc gattatacaa ggtgttactc  1500
gtaatggtct tgctgatccg gcgctcatag gtttaaattc aggtgcttca tttgctttag  1560
cattaacata tgcagtttta ccaaacactt cattttttaat attgatgttt gctggatttt  1620
taggtgctat tctaggaggt gctattgtat taatgatagg ccgatctaga cgtgatggat  1680
ttaatccgat gcgtattatt ttagcgggtg cagcagtaag tgctatgtta acagcgctaa  1740
gtcaaggtat tgcattagct tttagactaa atcaaacagt aacattttgg actgctggag  1800
gcgtttcagg cacaacatgg tcacacctta gtgggcaat tccattaatt ggtattgcgt  1860
tattcattat attaacaatt agtaaacaac ttaccatttt aaatcttggt gaatcattag  1920
ctaaaggttt aggtcaaaat gtaacaatga tcagaggcat atgtttaatt attgctatga  1980
ttctagcagg tattgcagtt gctatcgctg acaagttgc atttgtaggt ttgatggtac  2040
```

```
ctcatatagc aagattttta attggaactg attatgctaa aattctacca ttaacagcct   2100
tgttaggtgg gatactcgtg cttgttgccg atgtgatagc acgatattta ggagaagcgc   2160
ctgttggtgc aatcatttca tttatcggtg ttccttactt tttatatttta gttaaaaaag  2220 gaggacgctc aatatgatta gttcaaataa taaacgcaga caattgatag cactggctgt   2280
ttttagcatt ctactatttc taggttgtac ttggagtatt acctcaggtg aatacaacat   2340
acctgttgaa agattttttca aaactttaat tggacaaggt gatgccattg atgagttaat   2400
cttattagat ttcaggttac ctcggatgat gattactatt ttggctggcg cagcgcttag   2460
tattagtggt gcaatagtgc aaagtgtcac aaaaaatcca atagctgaac caggtatatt   2520
aggtattaac gcaggtggcg gatttgcaat cgcattattt attgcaattg gtaaaattaa   2580
tgctgacaac tttgtttatg tactgccgtt aataagtata ctaggtggta tcaccactgc   2640
attgattatt tttattttca gttttaataa aaatgaaggt gttacacctg cgagtatggt   2700
attaataggt gtaggtttac aaacagcatt atatggtggc tcaattacaa ttatgtcaaa   2760
atttgatgat aagcaatctg atttcatcgc tgcttggttt gcaggtaata tttggggtga   2820
cgaatggcca tttgtcattg catttttacc gtgggtgttg attattattc cttacttact   2880
atttaaatcg aatacactaa atattattca tacgggtgat aatattgcac gaggtctagg   2940
tgtaaggtta agcagagaac gtttaatatt attctttatc gcagtgatgt tatcatctgc   3000
tgctgtagca gtagcaggtt caatttcgtt tatcggatta atgggtccgc atattgccaa   3060
acgtatcgtt ggaccacgtc accagttgtt tttaccaatt gccattttag taggggcatg   3120
tttacttgtt atagctgata caattggcaa aattgtatta caaccaggtg gggttccagc   3180
aggtattgtc gtagcaatta ttggtgcacc gtatttctta tatttaatgt acaaaacgaa   3240
aaatgtatag tgtcaatgga cacaacttat tgctatgaaa ggcactttat tataaggctt   3300
ttcatagcat tttttatttta atgagccact caagactatt tattttttca ataatgaacc   3360
attaagttat caagaggatc ttatcaaaaa tatatttgat aacggtatca ggttaattct   3420
ttatgatagc gcattcattt attctgtttt atactatgac tgataatacc aaggaggtac   3480
aacatgatga aaagttaat caataaaaaa gaaacatttt taactgatat gcttgaagga   3540
ttgttaattg cgcacccaga gttagatctg attgctaata cagttattgt aaaaaaagct   3600
aagaaagaac atggtgtagc aatagtctct ggaggtggaa gcggacatga acctgcgcat   3660
gccggttttg ttgcagaagg tatgctagat gcagcggttt gtggcgaagt atttacatcg   3720
gatccaaa                                                            3728
```

<210> SEQ ID NO 13
<211> LENGTH: 3728
<212> TYPE: DNA
<213> ORGANISM: Staphylococcus aureus

<400> SEQUENCE: 13

```
tttggatccg atgtaaatac ttcgccacaa accgctgcat ctagcatacc ttctgcaaca    60
aaaccggcat gcgcaggttc atgtccgctt ccacctccag agactattgc tacaccatgt   120
tctttcttag cttttttttac aataactgta ttagcaatca gatctaactc tgggtgcgca   180
attaacaatc cttcaagcat atcagttaaa atgtttctt ttttattgat taacttttttc    240 atcatgttgt acctccttgg tattatcagt catagtataa aacagaataa atgaatgcgc   300
tatcataaag aattaacctg ataccgttat caaatatatt tttgataaga tcctcttgat   360
aacttaatgg ttcattattg aaaaaataaa tagtcttgag tggctcatta aataaaaaat   420
```

```
gctatgaaaa gccttataat aaagtgcctt tcatagcaat aagttgtgtc cattgacact    480 atacatttt  cgttttgtac attaaatata agaaatacgg tgcaccaata attgctacga    540
caatacctgc tggaacccca cctggttgta atacaatttt gccaattgta tcagctataa    600
caagtaaaca tgcccctact aaaatggcaa ttggtaaaaa caactggtga cgtggtccaa    660
cgatacgttt ggcaatatgc ggacccatta atccgataaa cgaaattgaa cctgctactg    720
ctacagcagc agatgataac atcactgcga taaagaataa tattaaacgt tctctgctta    780
accttacacc tagacctcgt gcaatattat cacccgtatg aataatattt agtgtattcg    840
atttaaatag taagtaagga ataataatca cacccacgg  taaaaatgca atgacaaatg    900
gccattcgtc accccaaata ttacctgcaa accaagcagc gatgaaatca gattgcttat    960
catcaaattt tgacataatt gtaattgagc caccatataa tgctgtttgt aaacctacac   1020
ctattaatac catactcgca ggtgtaacac cttcattttt attaaaactg aaaataaaaa   1080
taatcaatgc agtggtgata ccacctagta tacttattaa cggcagtaca taaacaaagt   1140
tgtcagcatt aattttacca attgcaataa ataatgcgat tgcaaatccg ccacctgcgt   1200
taatacctaa tatacctggt tcagctattg dattttttgt gacactttgc actattgcac   1260
cactaatact aagcgctgcg ccagccaaaa tagtaatcat catccgaggt aacctgaaat   1320
ctaataagat taactcatca atggcatcac cttgtccaat taaagttttg aaaaatcttt   1380
caacaggtat gttgtattca cctgaggtaa tactccaagt acaacctaga aatagtagaa   1440
tgctaaaaac agccagtgct atcaattgtc tgcgtttatt atttgaacta atcatattga   1500
gcgtcctcct ttttaactaa atataaaaa  gtaaggaaca ccgataaatg aaatgattgc   1560
accaacaggc gcttctccta aatatcgtgc tatcacatcg gcaacaagca cgagtatccc   1620
acctaacaag gctgttaatg gtagaatttt agcataatca gttccaatta aaaatcttgc   1680
tatatgaggt accatcaaac ctacaaatgc aacttgtcca gcgatagcaa ctgcaatacc   1740
tgctagaatc atagcaataa ttaaacatat gcctctgatc attgttacat tttgacctaa   1800 accttagct  aatgattcac caagatttaa aatggtaagt tgtttactaa ttgttaatat   1860
aatgaataac gcaataccaa ttaatggaat tgcccactta aggtgtgacc atgttgtgcc   1920
tgaaacgcct ccagcagtcc aaaatgttac tgtttgattt agtctaaaag ctaatgcaat   1980
accttgactt agcgctgtta acatagcact tactgctgca cccgctaaaa taatacgcat   2040
cggattaaat ccatcacgtc tagatcggcc tatcattaat acaatagcac ctcctagaat   2100
agcacctaaa aatccagcaa acatcaatat taaaaatgaa gtgtttggta aaactgcata   2160
tgttaatgct aaagcaaatg aagcacctga atttaaacct atgagcgccg gatcagcaag   2220
accattacga gtaacaccctt gtataatcgc accagaaact gcaagcgcca tacctacaat   2280
tactgctgct atatttctgg gaatcctaat ctcattgatg atgttttgct gttgattgct   2340
aggattataa ttaaaaatag cctctataat tgtagaggct tgaattttgg cgtcacctat   2400
taatgtagaa ataaatagtg tgattagtag tatcatactt aaacctataa tataggataa   2460
aaacttcaat ggcgttgggt tctctctatt tgtcatgtta attgtccttt ttatcatatt   2520
aacttactta attaagaata agctctgcga cataagtcat aagttaccag taaaggtttt   2580
ccagttttag gatctttact taaaacaaca tcaatattaa aaacttttc  taatatttcc   2640 tgtgttaata cgtcttctgt tgaacctgta gcgatgatat cccccttctttt catcgcaata   2700 agatgatctg agaaacgaat cgcttggttg atatcatgaa gaaccatgac aattgtacaa   2760
ccttgttcct gatttagctt ctgaactaat tctagtattt ctaattgatg acagatatct   2820
```

```
aaatatgttg ttggttcgtc taaaaagata atatcagttc tttgtgctaa tgccattgca    2880
atccaaacac gttgtctttg accaccactt aaatcattga ttgaacggtg tcggaatgta    2940
tcagttcctg taacttccat tgcccaatca atttctttct tatcctcagc agttaatcta    3000
ccaaatcctt tttgatgtgg aaaacgacca tatgaaacta attccccaac agttaagcca    3060
tctgctactt caggtgattg aggtaaaatg gctattttt ttgcaatctc tttcgtagat     3120
tgtgtatgaa tattttcacc atctaaaaat acttcgcctt ctttaactgc caataaacgt    3180
gacaatgcct ttagcaaagt agatttcccg cagccgttag gaccaatgat tgacgtcact    3240
ttgccatctg gtatttcaac atctaattta tttataatcg tgttatcccc gtaaccaatt    3300
ttaacttgtt gtccatgcaa acgattcata atttccctac tttcaataaa attctttctg    3360
tttataaaaa ataatttcta tttttaaatt atcaattttc aaagacatcc caattgataa    3420
tgattatcat gaacatcatt ataacatttt tcaatcttat tgactaacat acttttttaa    3480
attggatagc tcgatttgtc atgtcttgta tattacttt ataaaataaa aaacgcccac     3540
agataagtct tcatagttca aaacttgtc cgtggacttc tatttaagta tgtgtgctca     3600
taccatttat ttattcatct gcaagaaagc cattaccata gacatctctt acatcatgaa    3660
ttacgaggaa tgcatcttta tcgatttgtt taattaatcg ctttgctttt gaaacttgtg    3720
gatccaaa                                                            3728

<210> SEQ ID NO 14
<211> LENGTH: 798
<212> TYPE: DNA
<213> ORGANISM: Staphylococcus aureus

<400> SEQUENCE: 14
atgaatcgtt tgcatggaca acaagttaaa attggttacg gggataacac gattataaat      60
aaattagatg ttgaaatacc agatggcaaa gtgacgtcaa tcattggtcc taacggctgc     120
gggaaatcta ctttgctaaa ggcattgtca cgtttattgg cagttaaaga aggcgaagta     180
tttttagatg gtgaaaatat tcatacacaa tctacgaaag agattgcaaa aaaaatagcc     240
attttacctc aatcacctga agtagcagat ggcttaactg ttggggaatt agtttcatat     300
ggtcgttttc cacatcaaaa aggatttggt agattaactg ctgaggataa gaagaaaatt     360
gattgggcaa tggaagttac aggaactgat acattccgac accgttcaat caatgattta     420
agtggtggtc aaagacaacg tgtttggatt gcaatggcat tagcacaaag aactgatatt     480
atctttttag acgaaccaac aacatatttta gatatctgtc atcaattaga aatactagaa     540
ttagttcaga agctaaatca ggaacaaggt tgtacaattg tcatggttct tcatgatatc     600
aaccaagcga ttcgtttctc agatcatctt attgcgatga agaaggggaa tatcatcgct     660
acaggttcaa cagaagacgt attaacacag gaaatattag aaaaagtttt taatattgat     720
gttgttttaa gtaaagatcc taaaactgga aaaccttac tggtaactta tgacttatgt      780
cgcagagctt attcttaa                                                  798

<210> SEQ ID NO 15
<211> LENGTH: 798
<212> TYPE: DNA
<213> ORGANISM: Staphylococcus aureus

<400> SEQUENCE: 15
ttaagaataa gctctgcgac ataagtcata agttaccagt aaaggttttc cagttttagg      60
atctttactt aaaacaacat caatattaaa aacttttct aatatttcct gtgttaatac      120
```

```
gtcttctgtt gaacctgtag cgatgatatc cccttctttc atcgcaataa gatgatctga    180
gaaacgaatc gcttggttga tatcatgaag aaccatgaca attgtacaac cttgttcctg    240
atttagcttc tgaactaatt ctagtatttc taattgatga cagatatcta aatatgttgt    300
tggttcgtct aaaaagataa tatcagttct ttgtgctaat gccattgcaa tccaaacacg    360
ttgtctttga ccaccactta aatcattgat tgaacggtgt cggaatgtat cagttcctgt    420
aacttccatt gcccaatcaa tttctttctt atcctcagca gttaatctac caaatccttt    480
ttgatgtgga aaacgaccat atgaaactaa ttccccaaca gttaagccat ctgctacttc    540
aggtgattga ggtaaaatgg ctattttttt tgcaatctct ttcgtagatt gtgtatgaat    600
attttcacca tctaaaaata cttcgccttc tttaactgcc aataaacgtg acaatgcctt    660
tagcaaagta gatttcccgc agccgttagg accaatgatt gacgtcactt tgccatctgg    720
tatttcaaca tctaatttat ttataatcgt gttatccccg taaccaattt taacttgttg    780
tccatgcaaa cgattcat                                                  798

<210> SEQ ID NO 16
<211> LENGTH: 265
<212> TYPE: PRT
<213> ORGANISM: Staphylococcus aureus

<400> SEQUENCE: 16

Met Asn Arg Leu His Gly Gln Gln Val Lys Ile Gly Tyr Gly Asp Asn
1               5                   10                  15

Thr Ile Ile Asn Lys Leu Asp Val Glu Ile Pro Asp Gly Lys Val Thr
            20                  25                  30

Ser Ile Ile Gly Pro Asn Gly Cys Gly Lys Ser Thr Leu Leu Lys Ala
        35                  40                  45

Leu Ser Arg Leu Leu Ala Val Lys Glu Gly Glu Val Phe Leu Asp Gly
    50                  55                  60

Glu Asn Ile His Thr Gln Ser Thr Lys Glu Ile Ala Lys Lys Ile Ala
65                  70                  75                  80

Ile Leu Pro Gln Ser Pro Glu Val Ala Asp Gly Leu Thr Val Gly Glu
                85                  90                  95

Leu Val Ser Tyr Gly Arg Phe Pro His Gln Lys Gly Phe Gly Arg Leu
            100                 105                 110

Thr Ala Glu Asp Lys Lys Glu Ile Asp Trp Ala Met Glu Val Thr Gly
        115                 120                 125

Thr Asp Thr Phe Arg His Arg Ser Ile Asn Asp Leu Ser Gly Gly Gln
    130                 135                 140

Arg Gln Arg Val Trp Ile Ala Met Ala Leu Ala Gln Arg Thr Asp Ile
145                 150                 155                 160

Ile Phe Leu Asp Glu Pro Thr Thr Tyr Leu Asp Ile Cys His Gln Leu
                165                 170                 175

Glu Ile Leu Glu Leu Val Gln Lys Leu Asn Gln Glu Gln Gly Cys Thr
            180                 185                 190

Ile Val Met Val Leu His Asp Ile Asn Gln Ala Ile Arg Phe Ser Asp
        195                 200                 205

His Leu Ile Ala Met Lys Glu Gly Asp Ile Ile Ala Thr Gly Ser Thr
    210                 215                 220

Glu Asp Val Leu Thr Gln Glu Ile Leu Glu Lys Val Phe Asn Ile Asp
225                 230                 235                 240

Val Val Leu Ser Lys Asp Pro Lys Thr Gly Lys Pro Leu Leu Val Thr
                245                 250                 255
```

Tyr Asp Leu Cys Arg Arg Ala Tyr Ser
        260                265

<210> SEQ ID NO 17
<211> LENGTH: 28
<212> TYPE: DNA
<213> ORGANISM: Artificial Sequence
<220> FEATURE:
<223> OTHER INFORMATION: Synthetic primer

<400> SEQUENCE: 17
ttgaattcaa tacctcgatg taagcacg                                  28

<210> SEQ ID NO 18
<211> LENGTH: 28
<212> TYPE: DNA
<213> ORGANISM: Artificial Sequence
<220> FEATURE:
<223> OTHER INFORMATION: Synthetic primer

<400> SEQUENCE: 18
ttggatccac gattcataat ttccctac                                  28

<210> SEQ ID NO 19
<211> LENGTH: 28
<212> TYPE: DNA
<213> ORGANISM: Artificial Sequence
<220> FEATURE:
<223> OTHER INFORMATION: Synthetic primer

<400> SEQUENCE: 19
ttggatccaa cgaaaaatgt atagtgtc                                  28

<210> SEQ ID NO 20
<211> LENGTH: 28
<212> TYPE: DNA
<213> ORGANISM: Artificial Sequence
<220> FEATURE:
<223> OTHER INFORMATION: Synthetic primer

<400> SEQUENCE: 20
tttctagacg gcaagcttat gaacaaac                                  28

<210> SEQ ID NO 21
<211> LENGTH: 29
<212> TYPE: DNA
<213> ORGANISM: Artificial Sequence
<220> FEATURE:
<223> OTHER INFORMATION: Synthetic primer

<400> SEQUENCE: 21
tttggatcca caagtttcaa aagcaaagc                                29

<210> SEQ ID NO 22
<211> LENGTH: 28
<212> TYPE: DNA
<213> ORGANISM: Artificial Sequence
<220> FEATURE:
<223> OTHER INFORMATION: Synthetic primer

<400> SEQUENCE: 22
ttggatccat ttgtcatgtt aattgtcc                                  28

<210> SEQ ID NO 23
<211> LENGTH: 36
<212> TYPE: DNA

```
<213> ORGANISM: Artificial Sequence
<220> FEATURE:
<223> OTHER INFORMATION: Synthetic oligonucleotide

<400> SEQUENCE: 23
gcaatgggta caggatccat taaagggaaa ccaaag                              36

<210> SEQ ID NO 24
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 24
ttgaattcgt agcatcgtaa aactccctt                                      28

<210> SEQ ID NO 25
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 25
ttggtaccgg cggatataaa tcttcatt                                       28

<210> SEQ ID NO 26
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 26
ttgagctctt tcggtcataa gcgttgac                                       28

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
tcacgaagga ggctaattag                                                20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
cctcgcaacg gttagttaac                                                20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
cagctacggc taccgaaata                                                20
```

```
<210> SEQ ID NO 30
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 30
cattttgggg ggctattgtt gt                                              22

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
ggaggccatt accatggcag                                                 20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
tgctccccgc ttactcataa                                                 20

<210> SEQ ID NO 33
<211> LENGTH: 4
<212> TYPE: PRT
<213> ORGANISM: Artificial Sequence
<220> FEATURE:
<223> OTHER INFORMATION: Illustrative endoplasmic reticulum retention
      signal

<400> SEQUENCE: 33

Lys Asp Glu Leu
1

<210> SEQ ID NO 34
<211> LENGTH: 109
<212> TYPE: DNA
<213> ORGANISM: Artificial Sequence
<220> FEATURE:
<223> OTHER INFORMATION: primer

<400> SEQUENCE: 34
taaccaattt taacttgttg tccatgcaaa cgattcataa tttccctact ttcaataaaa      60
ttctttctgt ttataaaaaa taatttctat ttttaaatta tcaattttc                 109

<210> SEQ ID NO 35
<211> LENGTH: 147
<212> TYPE: DNA
<213> ORGANISM: Artificial Sequence
<220> FEATURE:
<223> OTHER INFORMATION: primer

<400> SEQUENCE: 35
tttcaacatc taatttattt ataatcgtgt tatccccgta accaatttta acttgttgtc      60
catgcaaacg attcataatt tccctactt caataaaatt ctttctgttt ataaaaaata     120
atttctattt taaattatc aatttc                                           147
```

```
<210> SEQ ID NO 36
<211> LENGTH: 205
<212> TYPE: DNA
<213> ORGANISM: Artificial Sequence
<220> FEATURE:
<223> OTHER INFORMATION: primer

<400> SEQUENCE: 36
aaagtagatt tcccgcagcc gttaggacca atgattgacg tcactttgcc atctggtatt        60
tcaacatcta atttatttat aatcgtgtta tccccgtaac caattttaac ttgttgtcca       120
tgcaaacgat tcataatttc cctactttca ataaaattct ttctgtttat aaaaaataat       180
ttctattttt aaattatcaa ttttc                                             205

<210> SEQ ID NO 37
<211> LENGTH: 251
<212> TYPE: DNA
<213> ORGANISM: Artificial Sequence
<220> FEATURE:
<223> OTHER INFORMATION: primer

<400> SEQUENCE: 37
tacttcgcct tctttaactg ccaataaacg tgacaatgcc tttagcaaag tagatttccc        60
gcagccgtta ggaccaatga ttgacgtcac tttgccatct ggtatttcaa catctaattt       120
atttataatc gtgttatccc cgtaaccaat tttaacttgt tgtccatgca aacgattcat       180
aatttcccta ctttcaataa aattctttct gtttataaaa ataatttct atttttaaat       240 tatcaatttt c                                                            251
```